(12) United States Patent
Dimitrov et al.

(10) Patent No.: US 10,287,340 B2
(45) Date of Patent: *May 14, 2019

(54) ANTI-HIV DOMAIN ANTIBODIES AND METHOD OF MAKING AND USING SAME

(71) Applicant: The United States of America, as represented by the Secretary, Department of Health and Human Services, Washington, DC (US)

(72) Inventors: Dimiter S. Dimitrov, Frederick, MD (US); Weizao Chen, Frederick, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 23 days.

This patent is subject to a terminal disclaimer.

(21) Appl. No.: 14/867,793

(22) Filed: Sep. 28, 2015

(65) Prior Publication Data

US 2016/0207985 A1 Jul. 21, 2016

Related U.S. Application Data

(62) Division of application No. 12/811,998, filed as application No. PCT/US2009/030351 on Jan. 7, 2009, now Pat. No. 9,181,327.

(60) Provisional application No. 61/019,426, filed on Jan. 7, 2008.

(51) Int. Cl.
| | | |
|---|---|---|
| C07K 16/10 | (2006.01) |
| C07K 16/00 | (2006.01) |
| C07K 16/28 | (2006.01) |
| A61K 38/17 | (2006.01) |
| A61K 39/42 | (2006.01) |
| C07K 14/73 | (2006.01) |
| A61K 47/68 | (2017.01) |

(52) U.S. Cl.
CPC ...... *C07K 16/1045* (2013.01); *A61K 38/1774* (2013.01); *A61K 39/42* (2013.01); *A61K 47/6841* (2017.08); *C07K 14/70514* (2013.01); *C07K 16/005* (2013.01); *C07K 16/1063* (2013.01); *C07K 16/2812* (2013.01); *C07K 2317/21* (2013.01); *C07K 2317/32* (2013.01); *C07K 2317/53* (2013.01); *C07K 2317/55* (2013.01); *C07K 2317/565* (2013.01); *C07K 2317/567* (2013.01); *C07K 2317/569* (2013.01); *C07K 2317/76* (2013.01); *C07K 2317/94* (2013.01); *C07K 2319/35* (2013.01)

(58) Field of Classification Search
CPC ............ C07K 16/1063; C07K 16/1045; C07K 2317/32; C07K 2317/565; C07K 2317/567; C07K 2317/569; C07K 2317/76; A61K 47/6841

USPC .......... 424/134.1, 160.1; 530/387.3
See application file for complete search history.

(56) References Cited

U.S. PATENT DOCUMENTS

| | | | |
|---|---|---|---|
| 4,002,531 A | 1/1977 | Royer | |
| 5,349,052 A | 9/1994 | Delgado et al. | |
| 5,612,460 A | 3/1997 | Zalipsky | |
| 7,196,187 B2 | 3/2007 | Frenken et al. | |
| 8,580,927 B2* | 11/2013 | Dimitrov | C07K 16/005 424/130.1 |
| 9,181,327 B2* | 11/2015 | Dimitrov | C07K 16/005 |
| 9,527,903 B2* | 12/2016 | Dimitrov | C07K 16/005 |
| 2005/0199076 A1 | 9/2005 | Tidare et al. | |
| 2006/0014232 A1 | 1/2006 | Inagawa et al. | |
| 2006/0019313 A1 | 1/2006 | Andersson et al. | |
| 2006/0072115 A1 | 4/2006 | Ivarsson et al. | |
| 2006/0073576 A1 | 4/2006 | Barnett et al. | |
| 2006/0094060 A1 | 5/2006 | Jarhede et al. | |
| 2006/0134800 A1 | 6/2006 | Malmqvist et al. | |
| 2006/0223113 A1 | 10/2006 | Sjobom et al. | |
| 2007/0202105 A1 | 8/2007 | Doyle et al. | |
| 2007/0269422 A1 | 11/2007 | Beirnaert et al. | |
| 2008/0096187 A1 | 4/2008 | Shaw et al. | |
| 2010/0316641 A1* | 12/2010 | Dimitrov | C07K 16/005 424/133.1 |
| 2014/0023645 A1* | 1/2014 | Dimitrov | C07K 16/005 424/133.1 |
| 2016/0039904 A1* | 2/2016 | Dimitrov | A61K 38/162 424/134.1 |
| 2018/0086812 A1 | 3/2018 | Dimitrov et al. | |

FOREIGN PATENT DOCUMENTS

| | | |
|---|---|---|
| EP | 09700209-1 | 2/2011 |
| WO | WO 1987/005330 | 9/1987 |
| WO | WO 1994/011026 | 5/1994 |

(Continued)

OTHER PUBLICATIONS

Chen et al. Curr Opin HIV AIDS. Mar. 2009 ; 4(2): 112-117.*

(Continued)

*Primary Examiner* — Lynn A Bristol

(74) *Attorney, Agent, or Firm* — Leydig, Voit & Mayer, Ltd.

(57) ABSTRACT

The invention provides single domain antibodies and derivatives thereof that bind antigens of interest, which are stable, soluble, and do not tend to aggregate. The invention also provides methods for constructing a dAb library and methods for screening dAb libraries to identify the dAb of the invention. The invention also provide methods of treating or preventing conditions by antigen neutralization by administering the dAbs of the invention.

9 Claims, 35 Drawing Sheets

Specification includes a Sequence Listing.

(56) References Cited

FOREIGN PATENT DOCUMENTS

| WO | WO 1995/006058 | 3/1995 |
|----|----------------|--------|
| WO | WO 2004/003019 | 1/2004 |
| WO | WO 2004/058821 | 7/2004 |
| WO | WO 2007/049017 | 5/2007 |
| WO | WO 2007/063311 | 6/2007 |
| WO | WO 2007/065027 | 6/2007 |
| WO | WO-2007/065027 | 6/2007 |
| WO | WO 2007/085815 | 8/2007 |
| WO | WO 2007/134037 | 11/2007 |
| WO | PCT/US11/60357 | 11/2011 |
| WO | PCT/US2011/60357 | 11/2011 |
| WO | WO 2014/150748 A2 | 9/2014 |

OTHER PUBLICATIONS

Chen et al. Proc Natl Acad Sci U S A. Nov. 4, 2008; 105(44): 17121-17126.*
Chen et al. Antiviral Res. Oct. 2010;88(1):107-15. doi: 10.1016/j.antiviral.2010.08.004. Epub Aug. 13, 2010.*
Ying et al.J Biol Chem. Aug. 30, 2013;288(35):25154-64. doi: 10.1074/jbc.M113.484154. Epub Jul. 18, 2013.*
Chen et al. J Virol. Jan. 2014;88(2):1125-39. doi: 10.1128/JVI.02566-13. Epub Nov. 6, 2013.*
Chen et al. Antiviral Res. Apr. 2015;116:62-6. doi: 10.1016/j.antiviral.2015.02.001. Epub Feb. 9, 2015.*
Chen et al. MAbs. May-Jun. 2016;8(4):761-74. doi: 10.1080/19420862.2016.1160180. Epub Mar. 10, 2016 (Abstract only).*
Shen et al. (The Journal of Biological Chemistry vol. 281, No. 16, pp. 10706-10714, Apr. 21, 2006).*
Amgen vs Sanofi and Regeneron Case: 17-1480 Document: 176 Filed: Feb. 6, 2018.*
Dufner (Trends Biotechnol. 24(11):523-29 (2006)).*
Hsu et al. (J Med Primatol. Aug. 2003;32(4-5):211-7; Abstract only).*
Information Disclosure Statement, filed Jul. 7, 2010 in U.S. Appl. No. 12/811,998.
Information Disclosure Statement, filed Mar. 25, 2011 in U.S. Appl. No. 12/811,998.
Information Disclosure Statement, filed Mar. 28, 2011 in U.S. Appl. No. 12/811,998.
Ward et al. (Nature 341: 544-546 (1989)).
Smith-Gill et al. (J. Immunol. 139: 4135-4144 (1987)).
Kumar et al. (J. Biol. Chem. 275: 35129-35136 (2000)).
Song et al. (Biochem Biophys Res Comm 268: 390-394 (2000)).
Brummerll et al. (Biochemistry 32: 1180-1187 (1993)).
Kobayashi et al. (Protein Engineering 12: 879-844 (1999)).
Burks et al. (PNAS 94: 412-417 (1997)).
Jang et al. (Molec. Immunol. 35: 1207-1217 (1998)).
Brorson et al. (J. Immunol. 163: 6694-6701 (1999)).
Coleman (Research in Immunol. 145: 33-36 (1994)).
Ibragimova and Eade (Biophysical Journal, Oct. 1999, vol. 77, pp. 2191-2198).
Office Action—EP09700209.1 (corr. EP Application), dated Feb. 2011, Dimitrov, et al.
Labrijn, Aran, et al., "Access of antibody molecultes to the conserved coreceptor bliding site on glycoprotein gp120 is sterically restricted on primary human immunodeficiency virus type 1", Journal of Virology, The American Society for Microbiology, vol. 77, No. 19, Oct. 1, 2003, pp. 10557-10559.
Dey, Barna, et al., "Neutralization of human immunodeficiency virus type 1 by sCD4-17b, a single-chain chimeric protein, based on sequential interaction of gp120 with CD4 and coreceptor", Journal of Virology, The American Society for Microbiology, vol. 77, No. 5, Mar. 1, 2003, pp. 2859-2865.
Zhang, Mei-Yun, et al., "A unique cross-reactive HIV-1 neutralizing CD4i human monoclonal antibody containing only a heavy chain: engineering a domain anti-body and improvement of its potency and solubility", Retrovirology, Biomed Central Ltd., London, GB, vol. 2, No. Supp 1., Nov. 4, 2005, p. 22.
Zhang, Mei-Yun, et al., "Novel approaches for identification of broadly cross-reactive HIV-1 neutralizing human monoclonal antibodies and improvement of their potency", Current Pharmaceutical Design, Bentham Science Publishers, Schiphol, NL, vol. 13, No. 2, Jan. 1, 2007, pp. 203-212.
Chen, W., et al., "Construction of a large phage-displayed human antibody domain library with a scaffold based on a newly identified highly soluable, stable heavy chain variable domain", Journal of Molecular Biology, London GB, vol. 382, No. 3, Oct. 10, 2008, pp. 779-789.
Chen, W., et al., "Human domain antibodies to conserved sterically restricted regions on gp120 as exceptionally potent cross-reactive HIV-1 neutralizers", Proceedings of the National Academy of Sciences of the USA, vol. 105, No. 44, Nov. 4, 2008, pp. 17121-17126.
Holt, L.J., et al., "domain antibodies: proteins for therapy", Trends in Biotechnology, Elsevier Publications, Cambridge, GB, vol. 21, No. 11, Nov. 1, 2003, pp. 484-490.
Abergel, et al., "A strong propensity toward loop formation characterizes the expressed reading frames of the D segments at the Ig H and T cell receptor loci", Eur J Immunol. Dec. 1991;21(12):3021-3025.
Alkhatib, et al., "CC CKR5: A RANTES, MIP-1alpha, MIP-1beta receptor as a fusion cofactor for macrophage-tropic HIV-1", 1996, Science 272:1955-1958.
Altschul & Gish, 1996, "Local alignment statistics", Doolittle ed., Methods in Enzymology 266: 460-480.
Altschul, et al., "Basic local alignment search tool", Journal of Molecular Biology 1990;215: 403-410.
Aplin, et al., "Preparation, properties, and applications of carbohydrate conjugates of proteins and lipids", CRC Crt. Rev. Biochem., pp. 259-306 (1981).
Bond, et al., "Contributions of CDR3 to Vhh domain stability and the design of monobody scaffolds for naive antibody libraries", J Mol Biol. Sep. 19, 2003;332(3):643-55.
Bradbury, et al., "Antibodies from phage antibody libraries", Journal of Immunological Methods 290 (2004) 29-49.
Brooks, et al., "Requirement of vascular integrin alphavbeta3 for angiogenesis", 1994, Science 264:569-571.
Chan, et al., "Core structure of gp41 from the HIV envelope glycoprotein", Cell 89:263-273 (1997).
Choe, et al., "The beta-chemokine receptors CCR3 and CCR5 facilitate infection by primary HIV-1 isolates", 1996, Cell 85:1135-1148.
Crowley, et al., "Prevention of metastasis by inhibition of the urokinase receptor". 1993, Proc Natl Acad. Sci. USA 90:5021-5025.
De Haard, et al., "A large non-immunized human fab fragment phage library that permits rapid isolation and kinetic analysis of high affinity antibodies". J Biol Chem. 1999, 274(26):18218-18230.
Decker, JM et al. ,(2005) "Antigenic conservation and immunogenicity of the HIV coreceptor binding site". J Exp Med 201:1407-1419.
Delgado, et al., "The Uses and Properties of PEG-Linked Proteins", (1992), Crit. Rev. Thera. Drug Carrier Sys. 9:249-304.
Deng, et al., "Identification of a major co-receptor for primary isolates of HIV-1", 1996, Nature 381:661-666.
Dimitrov, DS, "Fusin: a place for HIV-1 and T4 cells to meet", 1996, Nat. Med., 2:640-641.
Dimitrov, DS, "Virus entry: molecular mechanisms and biomedical applications", Nat. Rev. Microbiol., Feb. 2004;2(2):109-122.
Doranz, et al., "A dual-tropic primary HIV-1 isolate that uses fusin and the beta-chemokine receptors CKR-5, CKR-3, and CKR-2b as fusion cofactors", 1996, Cell 85:1149-1158.
Dragic, et al., "HIV-1 entry into CD4+ cells is mediated by the chemokine receptor CC-CKR-5", 1996, Nature 381:667-673.
Edge, et al., "Deglycosylation of glycoproteins by trifluoromethanesulfonic acid", Anal. Biochem., 118:131-137 (1981).
Ewert, et al., "Biophysical properties of camelid $V_{HH}$ domains compared to those of human $V_H3$ domains", Biochemistry, 41, 3628-3636 (2002).
Fauci, "25 years of HIV", Nature 453:289-290 (2008).

(56) References Cited

OTHER PUBLICATIONS

Fellouse, et al., "Synthetic antibodies from a four-amino-acid code: a dominant role for tyrosine in antigen recognition", Proc Natl Acad Sci U S A. Aug. 24, 2004;101(34):12467-12472. Epub Aug. 11, 2004.
Feng, et al., "HIV-1 entry cofactor: functional cDNA cloning of a seven-transmembrane, G protein-coupled receptor", 1996, Science 272:872-876.
Ferrantelli, et al., 2002 "Neutralizing antibodies against HIV—back in the major leagues?", Curr Opin Immunol. Aug. 2002;14(4):495-502. Review.
Ferrantelli, TR., "Do not underestimate the power of antibodies-lessons from adoptive transfer of antibodies against HIV", Vaccine. Dec. 19, 2002;20 Suppl 4:A61-A65. (Joe Found).
Fouts, TR et al., "Expression and characterization of a single-chain polypeptide analogue of the human immunodeficiency virus type 1 gp120-CD4 receptor complex". J Virol 74:11427-11436 (2000).
Francis, et al., (1998), Intern. J. Hematol. 68:1-18.
Gish, et al., "Identification of protein coding regions by database similarity search", 1993, Nature Genetics 3: 266-272.
Glaser, et al., "Dissection of the combining site in a humanized anti-tac antibody", J. Immunol. 149:2606-2614, 1992.
Hammes, et al., "Subcutaneous injection of a cyclic peptide antagonist of vitronectin receptor-type integrins inhibits retinal neovascularization", 1996, Nature Medicine 2:529-533.
Hoogenboom, "Designing and optimizing library selection strategies for generating high-affinity antibodies", Tibtech, 1997 (15), 62-70.
Huang, CC et al., "Structure of a V3-containing HIV-1 gp120 core". Science 310:1025-1028 (2005).
Huang, et al., "Structural basis of tyrosine sulfation and $V_H$-gene usage in antibodies that recognize the HIV type 1 coreceptor-binding site on gp120", Proc Natl Acad Sci U S A 101:2706-2711 (2004).
International Search Report dated Jul. 9, 2009, corresponding to PCT/US2009/030351.
Jain, et al., "Mechanisms of heterogeneous distribution of monoclonal antibodies and other macromolecules in tumors: significance of elevated interstitial pressure", Cancer Res. 48, 7022-7032 (1988).
Jirholt, et al., " Exploiting sequence space: shuffling in vivo formed complementarity determining regions into a master framework", Gene. Jul. 30, 1998;215(2):471-476.
Jones, et al., "Conformational changes in cell surface HIV-1 envelope glycoproteins are triggered by cooperation between cell surface CD4 and co-receptors", 1998, J. Biol. Chem., 273:404-409.
Karlin, et al., "Applications and statistics for multiple high-scoring segments in molecular sequences", Proc. Natl. Acad. Sci. USA 1993;90: 5873-5877.
Karlin, et al., "Methods for assessing the statistical significance of molecular sequence features by using general scoring schemes", Proc. Natl. Acad. Sci. USA 1990;87: 2264-2268.
Kohler, et al., "Continuous cultures of fused cells secreting antibody of predefined specificity", Nature 256, 495-497 (1975).
Kortt, et al., (1995). "Solution properties of *Escherichia coli*-expressed $V_H$ domain of anti-neuraminidase antibody NC41". J. Protein Chem. 14, 167-178.
Kostelny, et al., "Humanization and characterization of the ANTI-HLA-DR antibody 1D10". (Int. J. Cancer 93;556-565, 2001.
Kozlowski, et al., "Improvements in protein PEGylation: pegylated interferons for treatment of hepatitis C", (2001) Journal of Controlled Release 72:217-224.
Kwong, et al., "HIV-1 evades antibody-mediated neutralization through conformational masking of receptor-binding sites", Nature, 2002, 420:678-682.
Kwong, PD et al., (1998) "Structure of an HIV gp120 envelope glycoprotein in complex with the CD4 receptor and a neutralizing human antibody", Nature 393:648-659.
Labrijn, et al., "Access of antibody molecules to the conserved coreceptor binding site on glycoprotein gp120 is sterically restricted on primary human immunodeficiency virus type 1", Journal of Virology, Oct. 2003, 77: 10557-10565.
Lee, CV, et al., "High-affinity human antibodies from phage-displayed synthetic fab libraries with a single framework scaffold", J. Mol. Biol. (2004) 340, 1073-1093.
Liu, S et al., "Different from the HIV fusion inhibitor C34, the anti-HIV drug Fuzeon (T-20) inhibits HIV-1 entry by targeting multiple sites in gp41 and gp120", J Biol Chem 280:11259-11273 (2005).
Luo, et al., "Humanization of an anti-ICAM-1 antibody with over 50-fold affinity and functional improvement", J. Immunol Meth., 275:31-40, 2002.
Maione, et al., "Inhibition of tumor growth in mice by an analogue of platelet factor 4 that lacks affinity for heparin and retains potent angiostatic activity", 1990, Cancer Res. 51:2077-2083.
McCafferty, J., et al., "Phage antibodies: filamentous phage displaying antibody variable domains", Nature, 348 (1990) 552-554.
McKnight, A. et al., "Inhibition of human immunodeficiency virus fusion by a monoclonal antibody to a coreceptor (CXCR4) is both cell type and virus strain dependent", J Virol. Feb. 1997;71(2):1692-1696.
Merrifield, J., "Solid phase peptide synthesis. I. The synthesis of a tetrapeptide", Am. Chem. Soc. 85:2149-2154, 1963.
Min, et al., 1996, "Urokinase receptor antagonists inhibit angiogenesis and primary tumor growth in syngeneic mice", Cancer Res. 56:2428-2433.
Moulard, et al., "Broadly cross-reactive HIV-1-neutralizing human monoclonal Fab selected for binding to gp120-CD4-CCR5 complexes", Proc. Natl. Acad. Sci., 2002, 99:6913-6918.
Muyldermans, et al., "Recognition of antigens by single-domain antibody fragments: the superfluous luxury of paired domains", TRENDS in Biochemical Sciences vol. 26 No. 4, 230-235 Apr. 2001.
Myers, et al., "Optimal alignments in linear space", CABIOS 1988;4: pp. 11-17.
Myszka, et al., "Energetics of the HIV gp120-CD4 binding reaction", Proc. Natl. Acad. Sci. USA, 97:9026-9031 (2000).
Nicaise, et al., "Affinity transfer by CDR grafting on a nonimmunoglobulin scaffold", Protein Science, 2004, 13:1882-1891.
Pankow, R et al., "The HTLV-I tax protein transcriptionally modulates OX40 antigen expression", J. Immunol. Jul. 1, 2000;165(1):263-270.
Parren, et al., "The neutralizing antibody response to HIV-1: viral evasion and escape from humoral immunity", AIDS, 1999, 13:S137-S162.
Pearson, et al., "Improved tools for biological sequence comparison", Proc. Natl. Acad. Sci. USA 1988;85: 2444-2448.
Perno, CF et al. , "Overcoming resistance to existing therapies in HIV-infected patients: the role of new antiretroviral drugs", J Med Virol 80:565-576 (2008).
Poignard, et al., "GP120: biologic aspects of structural features", Annu. Rev. (2001). Immunol., 2001, 19:253-274.
Potter, et al., "Staphylococcal protein A simultaneously interacts with framework region 1, complementarity-determining region 2, and framework region 3 on human VH3-encoded Igs", J Immunol. Oct. 1, 1996;157(7):2982-2988.
Prabakaran, et al., "Structure and function of the HIV envelope glycoprotein as entry mediator, vaccine immunogen, and target forinhibitors", Adv Pharmacol 55:33-97 (2007).
Quinnan, et al., "Expression and characterization of HIV type 1 envelope protein associated with a broadly reactive neutralizing antibody response", AIDS Res Hum Retroviruses 15:561-570 (1999).
Randen, et al., "Complementarity-determining region 2 is implicated in the binding of staphylococcal protein A to human immunoglobulin $V_H$III variable regions", Eur J Immunol. Oct. 1993;23(10):2682-2686.
Ray, et al., "HIV-1 coreceptors and their inhibitors". Curr Top Microbiol Immunol 303:97-120 (2006).
Roberge, et al., "A strategy for a convergent synthesis of N-linked glycopeptides on a solid support", Science 269:202-204, 1995.
Sage, et al., "Inhibition of endothelial cell proliferation by SPARC is mediated through a $Ca^{2+}$-Binding EF-hand sequence", 1995, J. Cell. Biochem. 57:127-140.

(56) References Cited

OTHER PUBLICATIONS

Sage, et al., "SPARC mediates focal adhesion disassembly in endothelial cells through a follistatin-like region and the Ca(2+)-binding EF-hand", J Cell Biochem. Feb. 1995;57(2):341-50.
Sattentau, et al., "Conformational changes induced in the envelope glycoproteins of the human and simian immunodeficiency viruses by soluble receptor binding", 1993, J. Virol., 67:7383-7393.
Sattentau, et al., "Conformational changes induced in the human immunodeficiency virus envelope glycoprotein by soluble CD4 binding", 1991, J. Exp. Med., 174:407-415.
Schellekens, H. "Immunogenicity of therapeutic proteins: clinical implications and future prospects", Clin. Ther. 24, 1720-1740 (2002).
Shalaby, et al., "Development of humanized bispecific antibodies reactive with cytotoxic lymphocytes and tumor cells overexpressing the HER2 protooncogene", J. Exp. Med. 17: 217-225, 1992.
Sheets, et al., "Efficient construction of a large nonimmune phage antibody library: the production of high-affinity human single-chain antibodies to protein antigens", Proc Natl Acad Sci U S A. May 26, 1998;95(11):6157-62 (1998).
Singer, et al., "Optimal humanization of 1B4, an anti-CD18 murine monoclonal antibody, is achieved by a correct choice of human V-region framework sequences", J. Immunol, 150:2844-2857, (1993).
Sjolander, et al., "Integrated fluid handling system for biomolecular interaction analysis", Anal. Chem. 63:2338 2345, 1991.
Söderlind, et al. "Recombining germline-derived CDR sequences for creating diverse single-framework antibody libraries", Nature Biotechnol. 18, 852-856 (2000).
Sojar, HT., et al., "A chemical method for the deglycosylation of proteins", Arch Biochem Biophys. Nov. 15, 1987;259(1):52-57.
Szabo, et al., "Surface plasmon resonance and its use in biomolecular interaction analysis (BIA)", Curr. Opin. Struct. Biol. 5:699-705, 1995.
Tempest, et al., "Reshaping a human monoclonal antibody to inhibit human respiratory syncytial virus infection in vivi", Biotechnology 9:266-271, 1992.
Thotakura, et al., "Enzymatic deglycosylation of glycoproteins", Meth. Enzymol. 138:350-359 (1987).
Tolsma, et al., "Peptides derived from two separate domains of the matrix protein thrombospondin-1 have anti-angiogenic activity", 1993, J. Cell Biol. 122:497-511.
Veazey, et al., "Prevention of virus transmission to macaque monkeys by a vaginally applied monoclonal antibody to HIV-1 gp120", Nat Med. Mar. 2003;9(3):343-6. Epub Feb. 10, 2003.
Ward, et al., "Binding activities of a repertoire of single immunoglobulin variable domains secreted from *Escherichia coli*", Nature 341,544-546 (1989).
Wilbur, et al., "Rapid similarity searches of nucleic acid and protein data banks", Proc Natl Acad Sci USA 1983;80:726-730.
Wu, et al., "Attempts to locate complementarity-determining residues in the variable positions of light and heavy chains", Ann. NY Acad. Sci. 190:382-393 (1971).
Wu, et al., "Length distribution of CDRH3 in antibodies", Proteins. May 1993;16(1):1-7.
Wyatt, et al., "Involvement of the V1/V2 variable loop structure in the exposure of human immunodeficiency virus type 1 gp120 epitopes induced by receptor binding", Science, 1995, 69:5723-5733.
Zhang, et al. "Improved breadth and potency of an HIV-1-neutralizing human single-chain antibody by random mutagenesis and sequential antigen panning", J Mol Biol 335:209-219 (2004).
Zhang, et al., "Broadly cross-reactive HIV neutralizing human monoclonal antibody Fab selected by sequential antigen panning of a phage display library", J. Immunol. Methods 283:17-25 (2003).
Zhang, et al., "Monoclonal antibodies as therapeutic agents in oncology and antibody gene therapy", Cell Res. 17, 89-99 (2007).
Zhu, et al., "Potent neutralization of Hendra and Nipah viruses by human monoclonal antibodies", J Virol. Jan. 2006;80(2):891-899.
U.S. Appl. No. 12/811,998, filed Jan. 20, 2011, U.S. Pat. No. 9,181,327.
U.S. Appl. No. 14/777,245, filed Sep. 15, 2015.
U.S. Appl. No. 15/784,988, filed Oct. 16, 2017.
U.S. Appl. No. 61/791,885, filed Mar. 15, 2013, Dimotrov et al.

* cited by examiner

Figure 5A

```
              1           5              10                15             20
m0            Q  V  Q  L  V  Q  S  G  G  ... G  L  V  Q  P  G  G  S  L  R
              cag gtg cag ctg gtg cagtct ggggga... ggcttg gta cagcct ggagggtcc ctg aga
VH3-23*04     E                 E
              g-- --- --- --- --- g-- --- --- --- --- --- --- --- --- --g --- --- --- ---

--------- CDR1 - IMGT ---------
                       25              30                 35                   40
m0            L  S  C  A  A  S  G  F  S  F  S  T  Y  E  ... ... ... ... M  S
              ctc tcc tgt gca gcctct ggattc agcttc agt act tat gaa... ... ... ... atg agc
VH3-23*04                              T       S       A
              --- --- --- --- --- --- -c- --t --c -gc --- -cc--- --- --- --- --- ---

------ CDR2 - IMGT
                         45                50               55           60
m0            W  V  R  Q  A  P  G  K  G  L  E  W  V  S  P  I  S  G  S  G
              tgg gtc cgc cag gct cca gggaag gggctg gagtgg gtc tca cct att agt ggt agt ggt
VH3-23*04                                                          A
              --- --- --- --- --- --- --- --- --- --- --- --- --- g-- --- --- --- --- ---

──────────────────
                          65              70              75            80
m0            G  N  S  ... ... Y  Y  A  D  S  V  K  ... G  R  F  T  I  S  R
              ggt aac tca ... ... tac tac gca gac tcc gtg aag... ggccggttc acc atc tcc aga
VH3-23*04          S  T
              --- -g- a-- --- --- --- --- --- --- --- --- --- --- --- --- --- --- ---

85               90              95             100
m0            D  N  S  K  N  T  L  Y  L  Q  M  N  T  L  R  A  E  D  T  A
              gacaat tcc aagaac acg ctg tat ctg caa atg aac acc ctg agagcc gaggac acg gcc
VH3-23*04                                              S
              --- --- --- --- --- --- --- --- --- --- -g- --- --- --- --- --- --- ---

--------- CDR3 - IMGT ---------
                        104
m0            V  Y  Y  C  A  K  G  P  P  V  W  S  G  Y  Y  F  A  D  G  F
              gta tat tac tgt gcgaaa ggcccc ccg gtt tgg agt ggt tat tat ttc gct gat ggt ttt
VH3-23*04
              --- --- --- --- --- --- -a ──────────
m0            D  I  W  G  Q  G  T  M  V  T  V  S  S        (SEQ ID NO: 94)
              gat atc tgg ggccaa gggacaatg gtc accgtc tct tca    (SEQ ID NO: 95)
VH3-23*04
```

Figure 5B

Amino acid sequence of m0 framework region

QVQLVQSGGGLVQPGGSLRLSCAAS<CDR1>MSWVRQAPGKG

LEWVSP<CDR2>YYADSVKGRFTISRDNSKNTLYLQMNTLRA

EDTAVYYC<CDR3>WGQGTMVTVSS    (SEQ ID NO: 94)

Nucleotide sequence of m0 framework region

CAGGTGCAGCTGGTGCAGTCTGGGGGAGGCTTGGTACAGCCTGGAGGGTCCCTGAGA

CTCTCCTGTGCAGCCTCT<CDR1>ATGAGCTGGGTCCGCCAGGCTCCAGGGAAGGGGCT

GGAGTGGGTCTCACCT<CDR2>TACTACGCAGACTCCGTGAAGGGCCGGTTCACCATCT

CCAGAGACAATTCCAAGAACACGCTGTATCTGCAAATGAACACCCTGAGAGCCGAGGAC

ACGGCCGTATATTACTGT<CDR3>TGGGGCCAAGGGACAATGGTCACCGTCTCTTCA
(SEQ ID NO: 95)

Figure 8 contd.
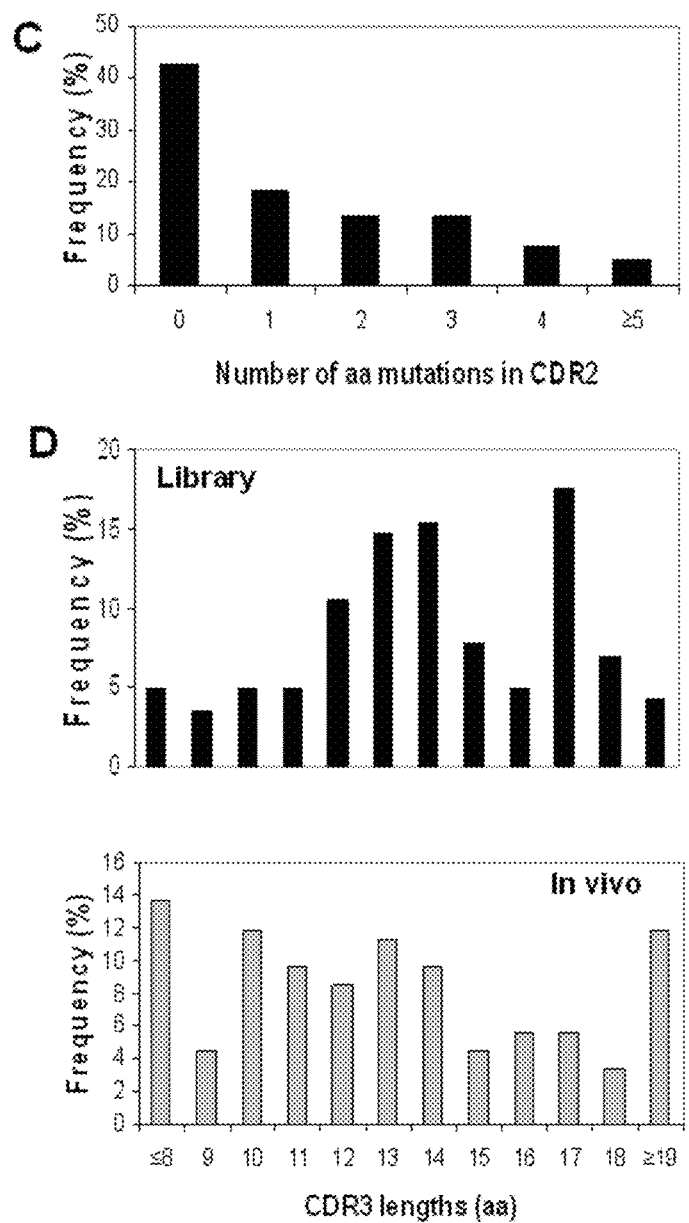

Figure 10

| aa | Frequency (%) | | | | | |
|----|------|------|------|------|------|------|
|    | 27 | 28 | 29 | 30 | 31 | 32 |
|    | -  | F  | -  | F  | -  | -  |
| A  | 16.5 |    | 11.4 |    | 31.6 | 11.4 |
| D  | 62.0 |    | 53.2 |    | 20.3 | 65.8 |
| S  | 10.1 |    | 13.9 |    | 31.6 | 11.4 |
| Y  | 11.4 |    | 21.5 |    | 16.5 | 11.4 |

After selection

| aa | Frequency (%) | | | | | |
|----|------|------|------|------|------|------|
|    | 27 | 28 | 29 | 30 | 31 | 32 |
|    | -  | F  | -  | F  | -  | -  |
| A  | 11.1 |    | 22.2 |    | 29.6 | 22.2 |
| D  | 33.3 |    | 18.5 |    | 18.5 | 40.0 |
| S  | 18.5 |    | 11.1 |    | 7.4  | 11.1 |
| Y  | 37.0 |    | 48.1 |    | 44.4 | 25.9 |

Before selection

Figure 17

| Virus | clade | m36 | | | scFv m9 | | | c34 | | |
|---|---|---|---|---|---|---|---|---|---|---|
| | | IC$_{50}$ | IC$_{90}$ | %In.[a] | IC$_{50}$ | IC$_{90}$ | %In. | IC$_{50}$ | IC$_{90}$ | %In. |
| 92UG | A | 2.2 | >10 | 74 | 6.7 | >20 | 81 | 1.1 | >4.0 | 75 |
| Bal | B | 0.12 | 1.1 | 100 | 2.2 | 8.9 | 98 | 1.0 | >4.0 | 85 |
| JR-FL | B | 0.37 | 3.3 | 96 | 2.3 | 15 | 95 | 1.0 | >4.0 | 62 |
| JRCSF | B | 0.37 | 1.1 | 100 | 2.2 | 6.6 | 100 | 1.3 | >4.0 | 68 |
| IIIB | B | 0.12 | 0.85 | 100 | 0.61 | 2.0 | 100 | 0.44 | 3.5 | 94 |
| 89.6 | B | 2.6 | >10 | 77 | 0.25 | >20 | 86 | 0.044 | >4.0 | 79 |
| R2 | B | 0.31 | 10 | 91 | 1.1 | 20 | 90 | 0.044 | >4.0 | 84 |
| NL4-3 | B | <0.12 | <0.12 | 100 | 0.57 | 2.1 | 100 | 3.4 | >4.0 | 57 |
| GXC | C | 0.24 | 1.1 | 100 | 1.9 | 20 | 90 | 1.3 | >4.0 | 63 |
| Z2Z6 | D | 10 | >10 | 50 | 0.66 | 5.2 | 97 | 0.72 | >4.0 | 67 |
| GXE | E | >10 | >10 | 0 | >20 | >20 | 0 | 3.1 | >4.0 | 64 |

[a]Percentage inhibition for the highest concentration (m36: 10 µg/ml; scFv m9: 20 µg/ml; c34: 4 µg/ml)

Figure 18

```
            1           5              10              15              20
m36         Q  V  Q  L  V  Q  S  G  G  .. G  L  V  Q  P  G  G  S  L  R
            cag gtg cag ctg gtg cagtct ggggga... ggcttg gta cagcct ggagggtcc ctg aga
VH3-48*03   E              E
            g-- --- --- --- --- g-- --- --- --- --- --- --- --- --- --- --- --- --- ---

─────────── CDR1 - IMGT ───────────
                            25              30              35              40
m36         L  S  C  A  A  S  A  F  D  F  S  D  Y  E  .. .. .. .. M  S
            ctc tcc tgt gcagcctct gct ttc gat ttc tct gat tat gaa... ... ... ... atg agc
VH3-48*03                        G        T        S                          N
            --- --- --- --- --- --- -ga --- acc --- ag- ag- --- --- --- --- --- --- -a-

────── CDR2 - IMGT
                            45              50              55              60
m36         W  V  R  Q  A  P  G  K  G  L  E  W  I  G  E  I  N  D  S  G
            tgg gtc cgc cag gct cca gggaaggggctg gagtgg att gggaaatc aat gat agt gga
VH3-48*03                                                 V  S  Y     S  S
            --- --- --- --- --- --- --- --- --- --- --- g-- tca t-c --t -g- ag- --- --t ─────────────────
                    65              70              75              80
m36         N  T  .. .. .. I  Y  N  P  S  L  K  .. S  R  V  T  I  S  R
            aacacc... ... ... att tac aat ccgtcc ctc aag... agt cgagtc accatc tcc aga
VH3-48*03   S  I           Y     A  D     V        G     F
            -gt --- ata --- --- tac --- gcagac--t g-g --- --- g-c --- t-- --- --- --- ---

85              90              95              100
m36         D  N  S  K  N  T  L  Y  L  Q  M  N  T  L  R  A  E  D  T  A
            gacaat tcc aagaacacg ctg tat ctg caaatg aacacc ctg agagccgaggacaca gcc
VH3-48*03         A                                      S
            --- --c g-- --- --- t-a --- --- --- --- --- -g- --- --- --- --- --- -g -t ─────────── CDR3 - IMGT ───────────
                    104
m36         I  Y  Y  C  A  I  Y  G  G  N  S  G  G  E  Y  W  G  Q  G  T
            ata tat tac tgt gcgata tat ggt ggt aactcc ggggagagtac tgg ggccagggcacc
VH3-48*03   V              R
            g-t --- --- --- --- -g- m36         L  V  T  V  S  S      (SEQ ID NO: 96)
            ctg gtc acc gtc tcc tca (SEQ ID NO: 97)
```

Figure 19

Nucleotide sequence of m36 caggtgcagctggtgcagtctgggggaggcttggtacagcctggagggtccctgagact ctcctgtgcagcctctgctttcgatttctctgattatgaaatgagctgggtccgccagg ctccagggaagggctggagtggattggggaaatcaatgatagtggaaacaccatttac aatccgtccctcaagagtcgagtcaccatctccagagacaattccaagaacacgctgta tctgcaaatgaacaccctgagagccgaggacacagccatatattactgtgcgatatatg gtggtaactccggggggagagtactggggccagggcacctggtcaccgtctcctca (SEQ ID NO: 97)

Amino acid sequence of m36

FR1 ———————————————————— |CDR1———|FR2———————————|CDR2———|FR3-
QVQLVQSGGGLVQPGGSLRLSCAASAFDFSDYEMSWVRQAPGKGLEWIGEINDSGNTIY

————————————————————————————————————|CDR3————|FR4————————|
NPSLKSRVTISRDNSKNTLYLQMNTLRAEDTAIYYCAIYGGNSGGEYWGQGTLVTVSS (SEQ ID NO: 96)

```
<----------------------------------- FR1 - IMGT -----------------------------------
1           5              10              15              20
Q   V   Q   L   V   Q   S   G   G       G   L   V   Q   P   G   G   S   L   R   L   S   C
cag gtg cag ctg gtg cag tct ggg gga ... ggc ttg gta cag cct gga ggg tcc ctg aga ctc tcc tg --------------->                    CDR1 - IMGT                <---------------
         25              30              35              40              45
    A   A   S   G   F   S   F   S   T   Y   E               M   S   W   V   R   Q   A
t gca gcc tct gga ttc agc ttc agt act tat gaa ... ... ... ... atg agc tgg gtc cgc cag gct FR2 - IMGT ----------------------->            CDR2 - IMGT            <---------
              50              55              60              65
P   G   K   G   L   E   W   V   S   P   I   S   G   S   G   G   N   S           Y   Y   A
cca ggg aag ggg ctg gag tgg gtc tca cct att agt ggt agt ggt ggt aac tca ... ... tac tac gc ------------------------------------------- FR3 - IMGT -------------------------------
         70              75              80              85              90
    D   S   V   K   G   R   F   T   I   S   R   D   N   S   K   N   T   L   Y   L   Q
a gac tcc gtg aag ... ggc cgg ttc acc atc tcc aga gac aat tcc aag aac acg ctg tat ctg caa --------------------------------------------->                            CD
              95              100             104
M   N   T   L   R   A   E   D   T   A   V   Y   Y   C   A   K   G   P   P   V   W   S   G
atg aac acc ctg aga gcc gag gac acg gcc gta tat tac tgt gcg aaa ggc ccc ccg gtt tgg agt gg

R3 - IMGT _____

Y   Y   F   A   D   G   F   D   I   W   G   Q   G   T   M   V   T   V   S   S       (SEQ ID NO: 96)
t tat tat ttc gct gat ggt ttt gat atc tgg ggc caa ggg aca atg gtc acc gtc tct tca           (SEQ ID NO: 97)
```

B
```
        SD
caggaggaatttaaaatgaaaagacagctatcgcgattgcagtggcactggctggttttc
              M  K  K  T  A  I  A  I  A  V  A  L  A  G  F
                                OmpA leader peptide SfiI
gctaccgtggcccaggcggcc ------------------------------------------
 A  T  V  A  Q  A  A SfiI
-------------------------- ggccaggccggccagcaccatcaccatcaccatggcgca
                            G  Q  A  G  Q  H  H  H  H  H  H  G  A
                                            Hexahistidine tag tacccgtacgacgttccggactacgcttcttaggagggtggtggctctgaggg           (SEQ ID NO: 98)
 Y  P  Y  D  V  P  D  Y  A  S  -  E  G  G  G  S  E              (SEQ ID NO: 99)
       HA tag                Amber    Gene III (aa 230-406)
                             stop
                             codon
```

Figure 24 m36 (SEQ ID NO: 100)
40d (SEQ ID NO: 101)
411g (SEQ ID NO: 102)
16c (SEQ ID NO: 103)
17b (SEQ ID NO: 104)
23e (SEQ ID NO: 105)
47e (SEQ ID NO: 106)
412d (SEQ ID NO: 107)
m16 (SEQ ID NO: 108)
Sb1 (SEQ ID NO: 109)
C12 (SEQ ID NO: 110)
X5 (SEQ ID NO: 111)
E51 (SEQ ID NO: 112)

Figure 25

| Virus | Clade | m36 | scFv m9 | C34 | m36SAbp | m36CH3 | m36b0Fc | m36h1Fc | m36c2Fc | m36h3Fc |
|---|---|---|---|---|---|---|---|---|---|---|
| 92UG037.8 | A | 147 ± 20* | 223 ± 7 | 297 ± 27 | 111 ± 44 | —† | — | — | — | — |
| Ba-L | B | 8 ± 0.7 | 73 ± 7 | 270 ± 27 | 13 ± 3 | — | — | — | — | — |
| JRFL | B | 25 ± 5 | 77 ± 17 | 270 ± 54 | 61 ± 6 | — | — | — | — | — |
| JR-CSF | B | 25 ± 11 | 73 ± 3 | 351 ± 81 | 24 ± 4 | — | — | — | — | — |
| IIIB | B | 8 ± 0.7 | 20 ± 2 | 119 ± 14 | 12 ± 3 | 167 ± 10 | — | 28 ± 0.9 | 28 ± 2 | 57 ± 2 |
| 89.6 | B | 173 ± 13 | 8 ± 0.7 | 12 ± 6 | 94 ± 22 | 102 ± 32 | >150 | 7 ± 0.5 | 5 ± 1 | 11 ± 6 |
| R2 | B | 21 ± 7 | 37 ± 3 | 13 ± 4 | 24 ± 8 | — | — | 364 ± 51 | >348 | >348 |
| NL4-3 | B | <8 | 29 ± 1 | 939 ± 135 | <8 | 75 ± 12 | >150 | <1 | <1 | <1 |
| GXC-44 | C | 16 ± 1 | 63 ± 10 | 351 ± 27 | 12 ± 4 | — | — | 25 ± 4 | 26 ± 10 | 28 ± 7 |
| Z2Z6 | D | 667 ± 60 | 22 ± 5 | 195 ± 35 | 667 ± 111 | — | — | — | — | — |
| GXE | E | — | — | 838 ± 27 | — | — | — | — | — | — |

*Antibody concentration (nM) resulting in 50% inhibition of virus infection (IC$_{50}$).
†No significant neutralization at the highest antibody concentration (667, 667, 1000, 667, 167, 150, 364, 348, and 348 nM for m36, scFv m9, C34, m36SAbp, m36CH3, m36b0Fc, m36h1Fc, m36c2Fc, and m36h3Fc, respectively).

Figure 32

| Virus | Clade | Antibodies | | | | | | | | |
|---|---|---|---|---|---|---|---|---|---|---|
| | | m36 | scFv m9 | C34 | m36SAbp | m36CH3 | m36b0Fc | m36h1Fc | m36c2Fc | m36h3Fc |
| 92UG037.8 | A | >667* | >667 | >1000 | >667 | –† | -- | -- | -- | -- |
| Bal | B | 73 ± 7 | 297 ± 37 | >1000 | 144 ± 6 | -- | -- | -- | -- | -- |
| JRFL | B | 220 ± 40 | 500 ± 20 | >1000 | 222 ± 17 | -- | -- | -- | -- | -- |
| JR-CSF | B | 73 ± 7 | 220 ± 19 | >1000 | 222 ± 67 | -- | -- | -- | -- | -- |
| IIIB | B | 57 ± 1 | 67 ± 3 | 946 ± 81 | 56 ± 6 | >167 | -- | 100 ± 23 | 287 ± 9 | 330 ± 17 |
| 89.6 | B | >667 | >667 | >1000 | >667 | >167 | >150 | 236 ± 36 | 321 ± 3 | 330 ± 17 |
| R2 | B | 667 ± 93 | 667 ± 70 | >1000 | 556 ± 50 | -- | -- | >364 | >348 | >348 |
| NL4-3 | B | <8 | 79 ± 7 | >1000 | 24 ± 0.6 | >167 | >150 | 12 ± 2 | 4 ± 0.8 | 13 ± 0.9 |
| GXC-44 | C | 73 ± 20 | >667 | >1000 | 211 ± 28 | -- | -- | >364 | >348 | >348 |
| ZZ6 | D | >667 | 173 ± 3 | >1000 | >667 | -- | -- | -- | -- | -- |
| GXE | E | -- | -- | >1000 | -- | -- | -- | -- | -- | -- |

*Antibody concentration (nM) resulting in 90% inhibition of virus infection (IC$_{90}$).
†No significant neutralization at the highest antibody concentration (667, 667, 1000, 667, 167, 150, 364, 348, and 348 nM for m36, scFv m9, C34, m36SAbp, m36CH3, m36b0Fc, m36h1Fc, m36c2Fc, and m36h3Fc, respectively).

ANTI-HIV DOMAIN ANTIBODIES AND METHOD OF MAKING AND USING SAME

INCORPORATION BY REFERENCE

This application described herein is a Divisional Application of U.S. Non-provisional application Ser. No. 12/811,998, filed Jan. 20, 2011, and issued as U.S. Pat. No. 9,181,327 on Nov. 10, 2015, which claims priority to PCT Application Serial No. PCT/US2009/030351, filed Jan. 7, 2009, which claims priority to U.S. Provisional Application Ser. No. 61/019,426, filed Jan. 7, 2008, all of which are hereby incorporated by reference in their entirety.

All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

STATEMENT REGARDING FEDERALLY SPONSORED RESEARCH AND DEVELOPMENT

This invention was made with Government support under project number ZIA BC 011155 by the National Institutes of Health, National Cancer Institute. The Government has certain rights in the invention.

INCORPORATION BY REFERENCE

In compliance with 37 C.F.R. § 1.52(e)(5), the sequence information contained in electronic file name: 69806US5_47992_Sequence_Listing.txt; size 57 KB; created on: Sep. 28, 2015; using Patent-In 3.5, and Checker 4.4.0 is hereby incorporated herein by reference in its entirety.

FIELD OF THE INVENTION

The present invention relates to domain antibodies, including derivatives, fusions and/or fragments thereof, having specificity for HIV and to their identification and manufacture. The invention further relates to the use of the domain antibodies of the invention in treating, preventing, and/or diagnosing various conditions, and particularly, HIV infections.

BACKGROUND OF THE INVENTION

The life-cycle of the human immunodeficiency virus (both HIV-1 and HIV-2) is well known. HIV primarily infects cells of the human immune system, such as helper T cells (specifically CD4+ T cells), macrophages and dendritic cells. Entry to cells of the immune system is mediated through interaction of the virion envelope glycoproteins (gp120 and gp41) with the receptor CD4 on the target cells. In addition, viral entry is modulated through at least two co-receptors known as CXCR4 and CCR5, which are members of the chemokine receptor family of proteins, and have been shown to function with CD4 as coreceptors for HIV-1 isolates that are tropic for T-cell lines or macrophages, respectively (Feng et al., 1996, Science 272:872-876; Alkhatib et al., 1996, Science 272:1955-1958; Deng et al., 1996, Nature 381:661-666; Dragic et al., 1996, Nature 381:667-673). Other molecules in this family including CCR3 and CCR2b, also appear to function as cofactors for some HIV-1 isolates (Doranz et al., 1996, Cell 85:1149-1158; Berson et al., 1997, J. Virol. 71: 1692-1696; Choe et al., 1996, Cell 85:1135-1148).

Current anti-HIV therapy includes the use of compounds which inhibit various aspects of the HIV life-cycle, including entry, fusion and replication in a target cell. While these therapies, particularly when used in combination with one another, are effective, they are frequently short-lived in that the viral strains rapidly develop resistance to one or more of the compounds used—a widespread and major problem in the current approaches in treating HIV infections.

Antibodies represent yet another promising approach in the treatment of HIV infections. Human monoclonal antibodies (mAbs) currently represent an important and growing technology in the development of inhibitors, vaccines, diagnostic and research tools. In fact, 22 mAbs have been approved by the US Food and Drug Administration against various disease in the past several decades for various disease indications, including rheumatoid arthritis (Centacor's REMICADE and Abbott Laboratories' HUMIRA), non-Hodgkin's lymphoma (Genentech's RITUXAN and IDEC's ZEVALIN) and respiratory syncytial virus infection (Medimmune's SYNAGIS). Many other antibody drug candidates are in the late stages of clinical trials and, as such, antibodies are now well established as both highly potent and well tolerated therapeutics.

However, no mAbs have yet been approved for clinical use against HIV-1. A fundamental problem in the development of HIV-1-neutralizing antibodies is the virus's innate ability to escape human immune surveillance during the long chronic infection. Several known mAbs, however, have been shown to exhibit potent and broad HIV-1 neutralizing activity in vitro, and can prevent HIV-1 infection in animal models (reviewed in Burton, 2002, Ferrantelli et al., 2002, and Veazey et al., 2003). A recent clinical trial suggested that two of these broadly HIV-1 neutralizing human mAbs, 2F5 and 2G12, lack side effects in humans (Armbruster et al., 2002; Stiegler et al., 2002). However, the potency of 2F5 and 2G12 used in combination in this clinical trial was significantly lower than currently available treatments and relapses occurred (Stiegler et al., 2002). Further increase in the potency of anti-HIV antibodies and/or new, more effective anti-HIV antibodies would be a significant advancement in the art.

Another fundamental problem in the development of effective therapeutic antibodies against HIV is the problem of epitope accessibility. It has been reported that some epitopes are sterically inaccessible to full size antibodies. For example, a study relating to HIV CD4-inducible (CD4i) epitopes by one of the present inventors has suggested that the size of the CD4i-specific neutralizing antibodies inversely correlates with neutralization efficiency and that perhaps antibody fragments might be more effective than whole antibodies in neutralizing the virus at such epitopes. See Labrijn et al., J. Virol., 2003. The study suggests that HIV's ability to evade the host's immune system may be linked in part to its having found a way to sterically hinder full-sized antibodies from accessing the CD4i epitopes. This study was limited, however, to exploring the effectiveness of scFv and Fab antibody fragments.

In the late 1980s, domain antibodies were identified as the smallest known antigen-binding fragments (Holt et al., 2003). Structurally, domain antibodies comprise the single chain variable heavy (VH) or variable light (VL) polypeptides, and due to their single-chain nature, range in size of only 11 kDa to 15 kDa. Domain antibodies, however, have a number of acknowledged problems to overcome to be suitable as potential therapeutics. Domain antibodies, particularly those derived from human antibodies, suffer from poor stability and solubility, and have a tendency to aggregate due to exposed regions of hydrophobicity in the absence of the paired VH or VL.

New and effective domain antibodies which would overcome the problems in the art, and an effective means of identifying and obtaining such domain antibodies, would be a valuable advance in the art. Such antibodies could be the basis of new methods and approaches for treating and/or prophylaxis of a variety of infections and conditions, such as HIV or cancer, in particular, infections and conditions which are capable of evading the immune system or therapeutic compounds and antibodies because certain epitope targets are sterically restricted.

SUMMARY OF THE INVENTION

The present invention relates to single domain antibodies that overcome the known problems in the art relating to domain antibodies and other anti-HIV antibodies, particularly poor stability, solubility and effectiveness. The domain antibodies of the invention show high affinity for their target epitopes, are highly expressed, are stable, and are capable of potent neutralization of a broad range of HIV isolates. The invention also relates to a novel VH framework identified by the present inventors that can be used as the basis of a highly diverse dAb library from which the inventive domain antibodies having potent neutralization activity against a broad range of HIV isolates can be obtained. The novel VH framework of the invention unexpectedly showed a high degree of compatibility with a wide diversity of CDR sequences, displayed properly folded dAbs, and expressed dAbs at high levels. The present invention also relates to novel fusion proteins containing the domain antibodies of the invention fused to agents (e.g., proteins) which function to enhance the stability of the dAbs of the invention and/or to enhance the effectiveness of the domain antibodies against their targets. In addition, the present invention provides therapeutic methods employing the domain antibodies and fusion proteins comprising the domain antibodies of the invention for treating and/or preventing HIV infections. Methods for preparing and screening domain antibody libraries are also provided herein.

In one embodiment, the present invention provides an isolated domain antibody or fragment thereof according to the amino acid sequence of m36, or an amino acid molecule having at least 60%, 80%, 85%, 90%, 95%, 96%, 97%, 98% or 99% sequence identity with the amino acid sequence of m36. In one aspect, the domain antibody or fragment can be immunoconjugated to one or more cytotoxic agents, chemotherapeutic agents, natural or synthetic toxins, radioactive isotopes, or antiviral agents. In another aspect, the antiviral agent can be zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, adefovir, clevadine, entecavir, or pleconaril.

In another embodiment, the present invention provides an isolated domain antibody or fragment thereof comprising (a) the m0 framework amino acid sequence or an amino acid sequence having at least 60%, 80%, 85%, 90%, 95%, 96%, 97%, 98% or 99% sequence identity thereto and (b) the CDR3 amino sequence of m36 or an amino acid sequence having at least 60%, 80%, 85%, 90%, 95%, 96%, 97%, 98% or 99% sequence identity thereto. In another aspect, the domain antibody or fragment thereof can be immunoconjugated to one or more cytotoxic agents, chemotherapeutic agents, natural or synthetic toxins, radioactive isotopes, or antiviral agents. In a further aspect, the antiviral agent can be zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, adefovir, clevadine, entecavir, or pleconaril.

In yet another embodiment, the present invention provides an isolated domain antibody or fragment thereof comprising (a) the m0 framework amino acid sequence or an amino acid sequence having at least 60%, 80%, 85%, 90%, 95%, 96%, 97%, 98% or 99% sequence identity thereto and (b) at least one of CDR1, CDR2 or CDR3 of m36 or an amino acid sequence having at least 60%, 80%, 85%, 90%, 95%, 96%, 97%, 98% or 99% sequence identity thereto. In one aspect, the domain antibody or fragment thereof can be immunoconjugated to one or more cytotoxic agents, chemotherapeutic agents, natural or synthetic toxins, radioactive isotopes, or antiviral agents. In another aspect, the antiviral agent can be zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, adefovir, clevadine, entecavir, or pleconaril.

In still another embodiment, the present invention relates to a domain antibody framework for the construction of a domain antibody library, said domain antibody framework comprising the framework sequence of m0 or an amino acid sequence having at least 60%, 80%, 85%, 90%, 95%, 96%, 97%, 98% or 99% sequence identity thereto.

In yet another embodiment, the present invention provides a fusion protein comprising a domain antibody or fragment thereof and a fusion partner, wherein the domain antibody or fragment thereof is the amino acid sequence of m36, or an amino acid molecule having at least 60%, 80%, 85%, 90%, 95%, 96%, 97%, 98% or 99% sequence identity with the amino acid sequence of m36. In yet another embodiment, the present invention relates to a fusion protein comprising a domain antibody or fragment thereof and a fusion partner, wherein the domain antibody or fragment thereof comprises (a) the m0 framework amino acid sequence or an amino acid sequence having at least 60%, 80%, 85%, 90%, 95%, 96%, 97%, 98% or 99% sequence identity thereto and (b) at least one of CDR1, CDR2 or CDR3 of m36 or an amino acid sequence having at least 60%, 80%, 85%, 90%, 95%, 96%, 97%, 98% or 99% sequence identity thereto.

In certain aspects, the fusion protein can be immunoconjugated to one or more cytotoxic agents, chemotherapeutic agents, natural or synthetic toxins, radioactive isotopes, or antiviral agents. The antiviral agent can be zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, adefovir, clevadine, entecavir, or pleconaril.

In yet another aspect, the fusion partner of the fusion proteins of the invention can be fused to the m36 or fragment thereof via a linker, such as, for example, a human IgG hinge region.

In certain other aspects, the fusion partner of the fusion proteins of the invention increases the stability of m36 or fragment thereof as compared to the m36 or fragment thereof alone. In certain other aspects, the fusion partner of the fusion proteins of the invention induces a CD4i epitope on Env thereby synergistically increases the effectiveness of the domain antibodies of the invention.

In one aspect, the fusion partner of the fusion proteins of the invention can be serum albumin-binding protein.

In certain other aspects, the fusion partner of the fusion proteins of the invention can be CD4 or a fragment or mimic thereof.

The fusion protein of claim 21, wherein the fusion partner is fused to the domain antibody or fragment thereof via a linker. In a further aspect, the linker can be an IgG hinge region.

In still another embodiment, the present invention provides a pharmaceutical composition comprising a therapeutically effective amount of a domain antibody or a fusion protein in accordance with the invention and a pharmaceutically acceptable salt.

In another embodiment, the invention relates to a method of treating and/or preventing an HIV infection in a patient in need thereof comprising, administering a therapeutically effective amount of (a) a domain antibody of the invention (b) a fusion protein of the invention, or (c) a pharmaceutical composition comprising a domain antibody or a fusion protein of the invention. In one aspect, the treatment method can further include co-administering a cytokine, anti-angiogenic agent, immunotherapeuic agent, anti-cancer agent, anti-bacterial agent, or anti-viral agent. In still another aspect, the treatment method further comprises co-administering a therapeutically effective amount of soluble CD4 (sCD4) or functional fragment or mimic thereof.

In yet another embodiment, the present invention provides a domain antibody library comprising a plurality of unique clones wherein each unique clone comprises the framework sequence of m0 or an amino acid sequence having at least 60%, 80%, 85%, 90%, 95%, 96%, 97%, 98% or 99% sequence identity thereto. In one aspect, the domain antibody library comprises at least $10^8$ or $10^9$ or $10^{10}$ unique clones.

In still another embodiment, the present invention provides a method of constructing a dAb library comprising the steps of (a) obtaining an isolated VH framework nucleotide sequence and (b) introducing a CDR1, CDR2 and CDR3 repertoire into the isolated VH framework nucleotide sequence, thereby forming a dAb library. In one aspect, the step of introducing the CDR1, CDR2 and CDR3 repertoire is achieved by graft replacement of the corresponding CDR sequences of the VH framework with the CDR1, CDR2 and CDR3 repertoire. In another aspect, the CDR1, CDR2 and CDR3 repertoire sequences can be obtained by PCR amplification using the primers of Table 1 and a non-immunized or immunized human antibody library template. In still another aspect, the graft replacement can be achieved by extension reactions between the PCR CDR products and the VH framework. In another aspect one, two or all CDRs could be mutagenized. The dAb library of the invention can be a phage-display library.

In still another embodiment, the present invention provides a method of identifying a dAb that binds to an antigen of interest, comprising panning the dAb phage-display library of the invention with an antigen of interest. In one aspect, the antigen of interest is HIV-1 CD4i antigen. In another aspect, the panning can be sequential panning using at least two antigens. The at least two antigens can be two HIV-1 CD4i antigens from different HIV-1 isolates.

In still another embodiment, the present invention provides a method for treating or preventing an HIV infection comprising administering in a therapeutically effective amount a composition comprising a dAb that binds to HIV-1 CD4i with a dissociation constant ($K_d$) of about 1 nM to about 500 nM.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 5A and 5B depict the m0 VH framework. FIG. 5A compares the m0 gene and the deduced amino acid sequence to human VH germline sequences from IMGT (ImMuno-GeneTics) database (imgt.cines.fr/textes/IMGTrepertoire/Proteins/protein/human/IGH/IGHV/Hu_IGHVallgenes.htm 1). The alignments to the known human VH germline sequences indicated VH3-23*04 as having the closest sequence identity with m0 although there are still significant differences. The figure displays the m0 amino acid sequence on the top row, followed below by its corresponding nucleotide sequence, and followed below the aligned VH3-23*04 sequences showing only those amino acid residues and nucleotide residues differing from the m0 sequences. The CDR (complementary determining region) and FR (framework) regions are shown according to IMGT numbering system. The italized regions flanking the CDR2 and CDR3 regions at their 5' and 3' ends correspond to the target sites for the primers used herein to amplify CDR2 and CDR3 segments from other sources in accordance with the invention, e.g. as described in Example 2. FIG. 5B provides separate amino acid and nucleotide sequences for m0, indicating the locations of the CDR sequences.

FIG. 8A shows the frequency of A/D/S/Y usage in each mutated position. Regarding the diversity of CDR2, FIG. 8B provides two bar graphs that show the number of VH germline subgroups of 1-7 as compared to the frequency of the appearance of the corresponding CDR2 in the library. FIG. 8C is a bar graph showing the frequency of mutations in CDR2. Regarding CDR3 sequence diversity, FIG. 8D provides bar graphs comparing the frequency of CDR3 lengths in vivo against the frequency of library clones having the same lengths.

FIG. 10 shows the frequency of A/D/S/Y residues at positions 27, 28, 29, 30, 31 and 32 in CDR1 before selection against Protein A versus after selection against Protein A in accordance with Example 2. Selection against Protein A was carried out, as explained in Example 2, to evaluate the extent to which correct folding occurred in the VH library of phagemid clones.

FIG. 17 shows the results of testing the $IC_{50}$ (the minimum inhibitory concentration needed to inhibit or neutralize 50% of the total virus), $IC_{90}$ (the minimum inhibitory concentration needed to inhibit or neutralize 90% of the total virus) and % In (percentage inhibition for the highest concentration of antibody—m36: 10 µg/ml; scFv m9: 20 µg/ml; c34: 4 g/ml) of m36 antibody, scFv m9 antibody, and c34 antibody against 11 different HIV-1 isolates from a total of 5 clades, A, B, C, D and E.

FIG. 18 shows the amino acid and nucleotide sequences for m36. The CDR1, CDR2 and CDR3 sequences are indicated. Also presented are the amino acid and nucleotide sequences of the human germline gene VH3-48*03. Only those amino acid and nucleotide residues that differ from the m36 sequences are indicated in the figure.

FIG. 19 provides the nucleotide and amino acid sequences of m36.

FIG. 20 provides a schematic representations of the m0 master framework and the cloning region of phagemid vector. (A) m0 master framework is analyzed using IMGT/V-QUEST tool provided by IMGT immunoglobulin database (imgt.cines.fr/IMGT_vquest/vquest?livret=0&Option=humanIg). The FRs and CDRs regions of the master gene are indicated according to the database. (B) Brief description of the cloning region of the phagemid vector phagemid vector. SfiI restriction sites are frequently used for cloning of genes. Hexahistidine tag and HA tag are included for purification and detection of protein products.

FIG. 24 shows an alignment of CD4i antibody VH sequences. The amino acid sequences of 12 known CD4i antibody VHs were obtained from a previous report (Huang et al. (2004), Proc. Natl. Acad. Sci. USA, 101:2706-2711, the contents of which are incorporated herein by reference). A multiple sequence alignment of these antibodies in addition to m36 is shown with CDRs indicated. Sequences are ordered based on the CDR3 lengths; IMGT numbering system is used. The acidic CDR residues are underlined with red. The gene usage with the FR and CDR regions and their CDR3 lengths are shown on the right.

FIG. 25 provides a table showing pseudotyped virus neutralization by m36 and its fusion proteins, as described below in Example 3. The table provides the antibody concentration (nM) resulting in 50% inhibition of virus infection ($IC_{50}$).

FIG. 32 provides a table showing pseudotyped virus neutralization by m36 and its fusion proteins, as described below in Example 3. The table provides the antibody concentration (nM) resulting in 90% inhibition of virus infection ($IC_{90}$).

DETAILED DESCRIPTION OF THE INVENTION

Figure 1:
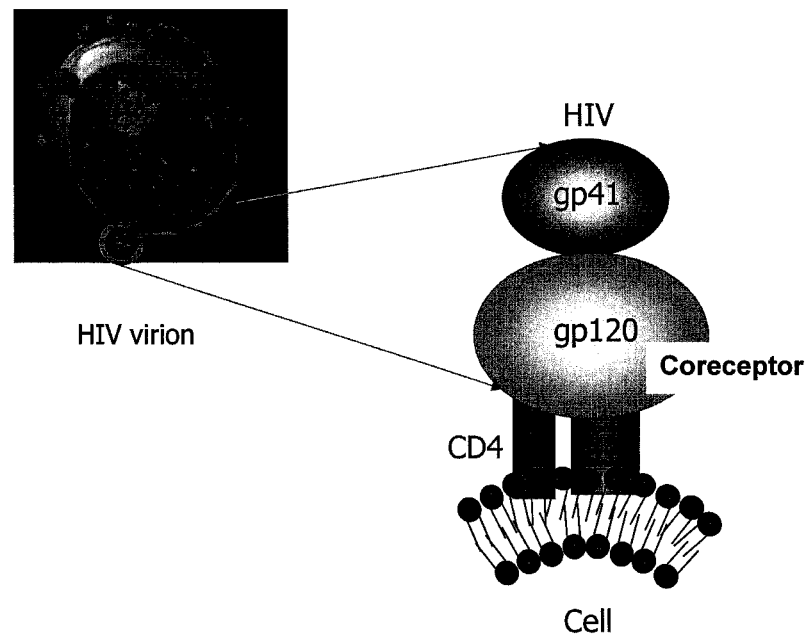
FIG. 1 is a simplified depiction of the general structure of the HIV envelope glycoprotein (Env) bound to CD4 and a coreceptor at the surface of a target cell. The HIV Env complex is embedded in the HIV envelope and consists of three (3) molecules of gp120 and a stem consisting of three (3) molecules gp41 of which only one is shown. The coreceptor can include chemokine receptors, CCR5 or CXCR4.
Figure 2:
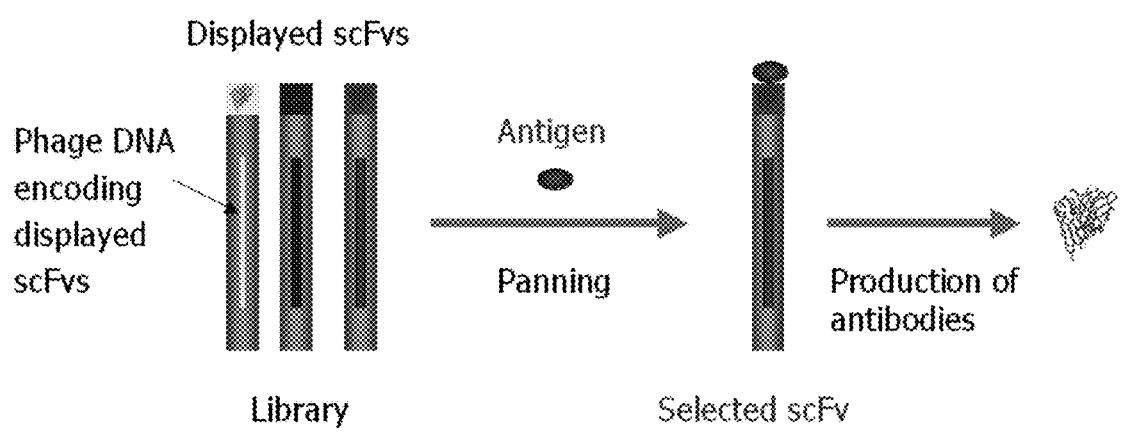
FIG. 2 depicts a general overview of a phage display antigen panning process that can be used to identify the antibodies of the invention.

The present inventors have developed new and useful single domain antibodies that overcome the known problems in the art relating to domain antibodies, particularly those problems associated with domain antibodies derived from human antibodies. Unlike the domain antibodies of the art, the antibodies of the invention are stable, highly soluble, and do not tend to form aggregates or polymerization products in solution. In addition, the domain antibodies of the invention have high affinity for their target epitopes and are highly expressed. The advantageous features of the inventive antibodies of the invention stem at least in part to the novel VH framework identified by the present inventors that is used as the basis of a highly diverse dAb library from which the inventive antibodies can be obtained. The novel VH framework of the invention unexpectedly and surprisingly showed a high degree of compatibility with a wide diversity of CDR sequences, maintains proper folding, expresses dAbs at high levels and which are highly soluble.

It is to be understood that present invention as described herein is not to be limited to the particular details set forth herein regarding any aspect of the present invention, including, the anti-HIV domain antibodies and variants and/or fragments thereof, VH framework, method of preparing diverse dAb library, methods of treatment, protocols, cell lines, animal species or genera, constructs, immunoconjugates and reagents described and, as such, may vary. It is also to be understood that the terminology used herein is for the purpose of describing particular embodiments only, and is not intended to limit the scope of the present invention.

Definitions

Unless defined otherwise, all technical and scientific terms used herein have the meaning commonly understood by one of ordinary skill in the art to which this invention belongs.

As used herein, the term "antibody" refers to immunoglobulin molecules (e.g., any type, including IgG, IgE, IgM, IgD, IgA and IgY, and/or any class, including, IgG1, IgG2, IgG3, IgG4, IgA1 and IgA2) isolated from nature or prepared by recombinant means or chemically synthesized. The terms "antibody" and "immunoglobulin" can be used synonymously throughout the specification, unless indicated otherwise.

As used herein, the term "antibody fragment" refers to a portion of a whole antibody which retains the ability to exhibit antigen binding activity. Examples include, but are not limited to, Fv, disulphide-linked Fv, single-chain Fv, Fab, variable heavy region ($V_H$), variable light region ($V_L$), and fragments of any of the above antibody fragments which retain the ability to exhibit antigen binding activity, e.g., a fragment of the variable heavy region $V_H$ retains its ability to bind its antigen.

As used herein, the term "antibody framework" is intended to mean the portion of an antibody variable domain which serves as a scaffold for the antigen binding loops of the variable domain, i.e., the CDR sequences, which is the same definition proffered by Kabat et al. 1991, which is incorporated herein by reference).

As used herein, the term "complementarity determining regions" (CDRs), or synonymously, antibody CDR, refers to the amino acid segments of an antibody that function as the antigen binding loops, as defined by Kabat et al. (1991). Each of the two variable domains of an antibody Fv fragment each contain three CDRs. The CDRs for the antigen binding loops, or synonymously, the "antigenic binding site".

As used herein, the term "domain antibody" (dAb) refers to an antibody whose complementary determining regions (CDRs) are part of a single domain polypeptide. Examples include, but are not limited to, variable heavy region ($V_H$) or fragment thereof, variable light region ($V_L$) or fragment thereof, heavy chain antibody (i.e. antibody devoid of light chain), single domain antibodies derived or engineered from conventional 4-chain antibodies, engineered antibodies and single domain scaffolds, wherein the scaffolds can be derived from any natural or synthetic source of antibody. The CDRs can be from any natural or synthetic source, and can be modified by any known or suitable means, e.g. site-directed mutagenesis.

As used herein, the term "framework region" refers to the nucleic acid sequence regions of an antibody gene that encode the structural elements of the molecule. In a domain antibody, e.g. the VH or VL of a human IgG, the framework region represents the sequences surrounding each of the three CDR sequences of the fragment polypeptides.

As used herein, the term "library" refers to a collection of nucleic acid sequences, wherein the individual nucleic acid molecules are carried or contained in a suitable vector, e.g. a DNA vector, expression vector, phagemid vector.

As used herein, the term "naive library" refers to a collection of nucleic acid sequences encoding the naturally occurring $V_H$ or $V_L$ repertoire from a non-immunized source.

As used herein, the term "repertoire" refers to the genetic diversity of a collection of molecules, e.g. a collection of CDR sequences.

As used herein, the terms "biological sample" or "patient sample" as used herein, refers to a sample obtained from an organism or from components (e.g., cells) of an organism. The sample may be of any biological tissue or fluid. The sample may be a clinical sample which is a sample derived from a patient. Such samples include, but are not limited to, sputum, blood, serum, plasma, blood cells (e.g., white cells), tissue samples, biopsy samples, urine, peritoneal fluid, and pleural fluid, saliva, semen, breast exudate, cerebrospinal fluid, tears, mucous, lymph, cytosols, ascites, amniotic fluid, bladder washes, and bronchioalveolar lavages or cells therefrom, among other body fluid samples. The patient samples may be fresh or frozen, and may be treated, e.g. with heparin, citrate, or EDTA. Biological samples may also include sections of tissues such as frozen sections taken for histological purposes.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

As used in this invention, the term "epitope" means any antigenic determinant on an antigen, e.g. a gp120 protein, to which an antibody binds through an antigenic binding site. Determinants or antigenic determinants on an antigen usually consist of chemically active surface groupings of molecules such as amino acids or sugar side chains and usually have specific three dimensional structural characteristics, as well as specific charge characteristics. In one embodiment of the invention, the HIV-1 epitope is the CD4-inducible epitope ("CD4i"), which becomes exposed on gp120 only after gp120 binds to the CD4 receptor.

As used herein, the term antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. Alternatively, an antibody that specifically binds to an antigen, in accordance with this invention, refers to the binding of an antigen by an antibody or fragment thereof with a dissociation constant ($K_d$) of 1 µM or lower, as measured by surface plasmon resonance analysis using, for example, a BIACORE® surface plasmon resonance system and BIACORE® kinetic evaluation software (eg. version 2.1). The affinity or dissociation constant ($K_d$) for a specific binding interaction is preferably about 500 nM or lower, more preferably about 300 nM or lower and preferably at least 300 nM to 50 pM, 200 nM to 50 pM, and more preferably at least 100 nM to 50 pM, 75 nM to 50 pM, 10 nM to 50 pM.

As used herein, the term "fusion protein" refers to two or more polypeptides coupled together which are not naturally found in a coupled arrangement. This can include translational fusions of two polypeptides, e.g., an antibody of the invention translationally fused via recombinant means to a fusion partner, such as an adduct molecule to enhance the stability of the antibody. Fusion proteins can also include proteins, e.g., an antibody of the invention, which have been physically coupled to another polypeptide. The two polypeptides in either case can be joined via a linker molecule.

As use herein, the term "fusion partner" refers to each of the polypeptides of a fusion protein.

As used herein, the term "linker" refers to a flexible molecular connection between two or more proteins, e.g., the linker between two m36 molecules. The molecular connection can be obtained from any suitable natural or synthetic source. The linker can be obtained, for example, from an antibody hinge region, e.g., IgG hinge region or from another natural or synthetic polypeptide source. The linker can be encoded, as in translational fusions. The linker can also be used to join or couple two already existing proteins.

As used herein, the term "mimic" refers to a second molecule, compound or substance which has the same or similar function or characteristics as a first molecule, compound or substance, while at the same time having a different structure.

VH Framework

In one embodiment, the present invention provides a novel and advantageous VH framework, which the present inventors have used as the starting point for generating a highly diversified phage-displayed domain antibody library which, in turn, can be used as convenient source of domain antibodies which are unexpectedly highly soluble and stable and possess good folding fidelity (despite a wide diversity of CDR molecules) and high affinity for their cognate antigenic targets.

In a preferred embodiment of the invention, the present invention provides a VH framework having the amino acid and nucleotide sequence of FIGS. 5A and 5B (indicated as m0, herein as "the m0 framework"). The construction of the m0 framework is described in Example 2 herein. Essentially, the m0 framework is the VH region of the Fab antibody, R3H1, which was identified by screening a large non-immune human Fab library (containing ~1.5×10$^{10}$ members) derived from the lymph nodes, spleen and peripheral blood lymphocytes of 50 human donors. As shown in Example 2, the m0 framework was found to have high levels of expression and high solubility. This completely natural VH domain antibody, belonging to the VH3 germline family, was then used as a framework to construct a large human VH domain library (with ~2.5×10$^{10}$ members) by grafting in a diverse repertoire of CDRs and/or mutating existing framework CDRs.

In another embodiment, the present invention provides a VH framework derived from m0, wherein the m0 contains certain advantageous amino acid modifications to enhance the properties of the framework antibody, including its solubility, stability, and lack of tendency to aggregate. Recombinant DNA techniques for modifying and/or changing the nucleic acid sequence and/or amino acid sequence of antibodies, including m0, are well known to those having ordinary skill in the art. For example, techniques for introducing genetic changes include site-directed mutagenesis, random mutagenesis, insertions, deletions, and PCR mutagenesis methods. All of these techniques are well known to those skilled in the art. See Ausubel et al., Current Protocols in Molecular Biology, John Wiley & Sons, New York, 2000, incorporated herein by reference.

Accordingly, the present invention relates to VH framework polypeptides that are at least 60%, preferably at least 80% identical, more preferably at least 90%, 95%, 96%, 97%, 98% or 99% identical to the amino acid sequence of the m0 framework.

The invention also relates to the nucleic acid encoding the VH framework m0 as shown in FIGS. 5A and 5B, or a VH framework nucleic acid sequence that is at least 90%, 95%, 96%, 97%, 98% or 99% identical to the nucleotide sequence of the m0 framework.

As used herein, the terms percent (%) sequence identity or percent (%) homology are used synonymously as a measure of the similarity of two or more amino acid sequences, or alternatively, between two or more nucleotide sequences. Methods for determining percent (%) sequence identity or percent (%) homology are well known in the art.

For the purposes of the present invention, percent (%) sequence identity or homology can be determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877. Another example of a mathematical algorithm used for comparison of sequences is the algorithm of Myers & Miller, CABIOS 1988; 4: pp 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448. Advantageous for use according to the present invention is the WU-BLAST (Washington University BLAST) version 2.0 software. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein). In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized. Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/-N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being-considered equal to uracil (U) in RNA sequences. And, without undue experimentation, the skilled artisan can consult with many other programs or references for determining percent homology.

The modifications to the amino acid sequence of the m0 framework to form variants that are at least 60%, preferably at least 80% identical, more preferably at least 90%, 95%, 96%, 97%, 98% or 99% identical to the amino acid sequence of the m0 framework, can be made using conservative amino acid substitutions. A conservative substitution is one in which the substituted amino acid has similar structural or chemical properties with the corresponding amino acid in the reference sequence. By way of example, conservative amino acid substitutions involve substitution of one aliphatic or hydrophobic amino acid, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Domain Antibody Library Construction and Screening Methods

In yet another embodiment, the present invention provides a domain antibody library prepared by introducing CDR diversity into the m0 framework (or derivative thereof having various amino acid substitutions as described above). Any suitable method for introducing CDR diversity is contemplated, including mutagenesis of one or more of the existing m0 CDR1, CDR2 or CDR3 sequences and the grafting in or replacement of one or more of the existing m0 CDR1, CDR2 or CDR3 sequences with a diverse repertoire of synthetically-prepared or naturally-obtained CDR sequences. The naturally-obtained CDR sequences can comprise a naive repertoire (not exposed to antigen) or an immunized repertoire (exposed to antigen).

The CDR sequences may be obtained from several sources, for example, databases such as the National Centre for Biotechnology Information protein and nucleotide databases www.ncbi.nlm.nih.gov, The Kabat Database of Sequences of Proteins of Immunological Interest www.kabatdatabase.com, or the IMGT database www.imgt.cines.fr. Alternatively, the CDR regions can be predicted from the VH and VL domain repertoire (see for example Kabat E A and Wu T T Attempts to locate complementarity determining residues in the variable positions of light and heavy chains. Ann. NY Acad. Sci. 190:382-393 (1971)). The CDR sequence may be a genomic DNA or a cDNA.

PCR amplification using primers that amplify the CDR1, CDR2 and CDR3 sequences, which may include framework sequence at the 5' and 3' ends of the CDR sequences, can be used to obtain the CDR repertoire for grafting into the framework sequence of the invention. Such PCR methods will be known to those of ordinary skill in the art. CDR sequences can also be obtained by any known nucleotide sequence synthesis methods, or by obtaining DNA fragments (e.g. restriction fragments) carrying the CDR sequences of interest. Any suitable method for obtaining the CDR sequences of the invention for use in grafting into the framework sequence is contemplated.

In a particular embodiment, diversity can be introduced into the m0 framework by grafting in a natural repertoire of one or more human CDR1, CDR2 or CDR3 sequences, obtained from known and available human antibody libraries, while synthetically modifying at least one existing CDR sequence of the m0 framework. Alternatively, diversity can be introduced by either only grafting in a CDR1, CDR2 and CDR3 repertoire, or by synthetically modifying each existing CDR sequence of the framework, without simultaneous grafting. Human antibody libraries can be obtained from any suitable source (e.g. commercial, university laboratories, public repositories of antibody libraries) and can include, for example, both immunized and non-immunized type libraries. As used herein, a non-immunized antibody library is one in which the patient(s) from which the antibodies were derived has not been exposed to the antigen against which the domain antibody library will ultimately be screened. An immunized antibody library is one in which the patient(s) from which the antibodies were derived have been exposed to the antigen against which the domain antibody library will ultimately be screened. As an example, where the goal is to pan or screen the domain antibody library for domain antibodies that neutralize an HIV antigen, an immune antibody library would be one whereby the patient from which the antibodies were sampled was infected with HIV.

Alternatively, the source libraries can comprise a synthetically prepared CDR repertoire.

Conveniently, the mutagenesis and/or grafting of the CDRs may be achieved by the method of overlap extension using primers which contain at each end sequences that are complementary or homologous to the anchor regions that form the basis of the framework region of m0 (or a variant thereof) and, in between, the CDR sequences. In one aspect, the primers of Table 1 can be used to obtain CDR products from any human antibody library and/or introduce mutations in CDR1 (with the H1R primer, which contains four triplet regions of degenerate sequences (underlined regions). Similarly mutations can be introduced in CDR2 and CDR3.

Regarding CDR mutagenesis, it is important when designing the CDR primers also to take into account sequence homology within the CDR regions which was observed in the sequence data from the naive clones, as the amino acids concerned are thought to play a structural role in the VH. It is desirable that highly conserved sequences within the CDRs, that is, residues that are conserved amongst a substantial proportion of the VH domains in the naive repertoire, should be retained in the synthetically modified primers, and excluded as targets for mutagenesis.

Splicing by overlap extension is a modification of the polymerase chain reaction, which has been used to generate gene fusions at very specific positions. It is based on the ability to fuse and amplify two DNA fragments containing homologous sequences i.e. 'anchors' around the fusion point.

For example, for the preparation of a 'synthetic' expression library, CDR primers incubated with framework region fragments will anneal at their complementary ends and fuse to generate randomised framework-CDR encoding fragments. This process yields CDR-1/FR-2, CDR-2/FR-3 and CDR-3/FR-4 fusion fragments. Two of these fragments are then fused, and so forth.

There then follows a denaturation step after which the fragments can be further annealed at the 'anchor-regions' and extended yielding the fused, double stranded gene product. If required this reaction can be followed by the PCR reaction amplifying the quantity of fused gene material. This method can easily be extended to fuse three or more fragments. Such or similar methods are disclosed in U.S. Pat. No. 7,196,187, and U.S. published application No. 2007/0202105, each of which are incorporated herein by reference.

Splicing by overlap extension allows the linking of the fusion fragments at specific positions to produce a fully assembled VH gene which can be cloned into a suitable phage display vector, such as the vector pHEN.5, using restriction enzymes such as SfiI/NotI.

It will be appreciated that other methods of introducing mutations, preferably including random or partially random sequences, into the CDRs would also be applicable. Such methods include, for example, cassette mutagenesis or the use of error-prone 'mutator' strains as bacterial hosts.

Any suitable methods can then be used to evaluate the size and sequence diversity of the domain antibody library. It will be appreciated that size and sequence diversity are key features of high-quality libraries. A finding consistent with theoretical considerations is that the affinity of antibodies selected is proportional to the size of the library, with $K_d$s ranging from $10^{6-7}$ for the smaller libraries to $10^9$ for the larger ones, and antibodies with affinity comparable to those obtained from immune libraries can be selected from naïve libraries that are large enough (Andrew et al., J. Immunol. Methods, 2004). For example, random nucleotide sequencing can be performed on a random selection of clones of the library to evaluate the source and extent of sequence diversity of the CDRs of the library. Diverse antibody libraries contain a high number of uniquely arranged VH sequences, i.e. a diverse assemblage of CDR1, CDR2 and CDR3 with unique combinations and sequences. Preferably, the domain antibody library of the invention comprises preferably at least about $10^8$, preferably at least about $10^9$, $10^{10}$, more preferably about $10^{11}$ or $10^{12}$ unique whole VH sequences.

In addition, the expressed VH products of the library clones can be evaluated for physical properties, such as solubility, stability and tendency to aggregate. Such methods would require expression of individual clones in a suitable vector in a host cell, e.g. *E. coli*, followed by the isolation of the expressed product, followed then by an analysis of the solubility, stability and tendency to aggregate, or any other desire trait.

Once a domain antibody library has been constructed, the present invention contemplates the screening of the library for antibodies that bind to or which are specifically immunoreactive against an antigen of interest, e.g. CD4i antigen.

The host cell used to express the VH products of the domain antibody library (e.g. phagemid library) may be prokaryotic or eukaryotic but is preferably bacterial, particularly *E. coli*.

The domain antibody library (e.g. phagemid library) according to the invention may be screened for antigen binding activity using conventional techniques well known in the art as described, for example, in Hoogenboom, Tibtech, 1997 (15), 62 70. By way of illustration, bacteriophage displaying a repertoire of nucleic acid sequences according to the invention on the surface of the phage may be screened against different antigens by a 'panning' process (see McCafferty, J., Griffiths, A D, Winter, G. and Chiswell, D J, Nature, 348 (1990) 552-554, which is incorporated herein by reference in its entirety) whereby the VH domains are screened for binding to an immobilized antigen (e.g. antigen on magnetic bead or bottom of microtiter well). Non-binding phage are removed. Binding phage are retained, eluted and amplified in bacterial or other suitable host (depending on the vector used). The panning cycle is repeated until enrichment of phage or antigen is observed and individual phage clones are then assayed for binding to the panning antigen and to uncoated polystyrene by phage ELISA.

As an indication of the binding affinities of antibodies that result from the screening described in the invention, dissociation constants for the VHs recognizing a protein antigen will typically be less than 100 nM, preferably less than 75 nM, more preferred less than 50 nM, still more preferred at less than 40 nM, most preferred less than 25 nM.

In one particular embodiment, a sequential panning technique is employed to obtain antibodies that bind to antigens from the same, but genetically distinct viruses or organisms. This approach is advantageous in identifying antibodies that might be more cross-reactive between different genetically distinct isolates of the same virus or other organisms, e.g. different isolates of HIV-1 or HIV-1 viruses from different clades. Antibodies with broader cross reactivity against different isolates of the same target would be advantageous. It is commonly known that in certain situations, e.g. HIV-1, it is difficult to obtain antibodies that will effective against HIV-1 isolates too genetically distinct from the isolate against which the antibody was prepared. That is, with some anti-HIV antibodies, the antibodies can suffer from having too narrow of an effectiveness.

In the context of phage display technology, this can be done by sequentially changing the antigen during the panning of a phage display library of the invention. By sequentially changing the antigen during panning of phage display libraries and screening the panned libraries using different antigens, the selected phage will display dAbs against conserved epitopes shared among all antigens used during the entire selection process. In one embodiment, gp120 antigens or gp120/CD4 complex antigens from two or more different HIV-1 isolates can be sequentially changed during the panning of phage display libraries of the invention, which will result in the enrichment of phages that display dAbs having affinity to shared epitopes of both or each of the gp120 antigens used during panning. Sequential panning of HIV antigens is discussed further in Zhang et al., 2004 and Zhang et al., 2003, each of which are incorporated herein by reference. The herein Example 2 employs a seqential panning approach.

As an example, antibodies which bind to HIV CD4i can be identified using a phagemid panning process. The HIV CD4i antigen may be coated on a microtiter plate or a magnetic bead and incubated with the domain antibody phagemid library of interest. Phage-linked VHs that do not bind to the CD4i antigen may be washed from the plate, leaving only bound phage. The bound phage may be eluted by addition of a thiol reducing agent such as dithiotreitol (DTT) resulting in cleavage of the disulfide bond linking the antibody to the phage. The recovered population of phage may be amplified by infection of *E. coli* hosts. This panning process may be repeated using the enriched population of phage to further enrich for a population of phage-linked antibodies that bind to the HIV CD4i antigen. The gene sequence encoding the dAbs may then be excised using standard cloning techniques and transferred to an *E. coli* expression vector which is used to transform an *E. coli* expression cell line. dAbs from the enriched pool may then be expressed and purified and characterized.

Domain Antibodies

In another embodiment, the present invention provides novel domain antibodies. The domain antibodies of the invention are advantageous over prior art antibodies, particularly domain antibodies, because the inventive antibodies are more stable, more soluble and do not tend to form aggregates or polymerization products in solution. In addition, the domain antibodies of the invention have high affinity for their target epitopes, are highly expressed, possess strong antigen neutralization action, and optionally can be broadly cross-reactive, e.g. cross-reactive antibody against HIV isolates from different clades. Accordingly, in one aspect, the domain antibodies of the invention can be used therapeutically to treat or prevent a number of conditions (e.g. cancer) or infections (e.g. HIV), or diagnostically to diagnose or detect condition- or infection-related antigens. As noted above, the advantageous features of the inventive antibodies of the invention stem at least in part to the novel VH framework, m0, and its derivatives, of the invention that forms the basis of the dAb library from which the inventive antibodies can be obtained.

In one aspect, the present invention embodies a number of different antibodies having gp120/CD4 CD4i binding characteristics identified by screening the m0 based domain antibody library of the invention using a sequential panning approach. In one aspect, the present invention provides a novel dAb, designated as m36, which possesses good solubility, has no detectable oligomerization tendencies, is highly specific for the CD4i antigen, and has broad affinity for different HIV isolates from different clades. (See Example 2). The amino acid and nucleotide sequence of m36 are given in FIGS. 18 and 19. The CDR sequences and framework sequences of m36 are shown in FIG. 18.

The present invention also contemplates, in accordance with the methods previously described or any other suitable known methods, derivatives of m36, which have been derivatived in any advantageous manner, such as, introducing changes in the at the nucleotide sequence level of the framework and/or the CDR1, CDR2 or CDR3 of m36. Methods for introducing genetic change to the nucleotide sequence of m36 are well known in the art, and can include PCR-based random or site-directed mutagenesis, insertions, deletions, gene shuffling, CDR grafting, etc. The present invention particular contemplates dAbs that have framework and/or CDR amino acid sequences having at least 60%, preferably at least 80%, or 85%, preferably at least 90%, 95%, 96%, 97%, 98%, or 99% or greater sequence identity with the framework and/or CDR sequences of m36.

Domain antibodies and/or fragments or derivatives thereof of the invention may be purified from any cell that expresses the antibodies, including host cells that have been transfected with antibody-encoding expression constructs. The host cells may be cultured under conditions whereby the antibodies are expressed. Purified dAbs antibodies may be separated from other cellular components that may associate with the antibodies in the cell, such as certain proteins, carbohydrates, or lipids using methods well known in the art. Such methods include, but are not limited to, size exclusion chromatography, ammonium sulfate fractionation, ion exchange chromatography, affinity chromatography, and preparative gel electrophoresis. Purity of the preparations may be assessed by any means known in the art, such as SDS-polyacrylamide gel electrophoresis.

Alternatively, antibodies may be produced using chemical methods to synthesize its amino acid sequence or portions of the antibody sequence (e.g. CDR sequences), such as by direct peptide synthesis using solid-phase techniques (e.g., Merrifield, J. Am. Chem. Soc. 85:2149-2154, 1963; Roberge, et al., Science 269:202-204, 1995, each of which are incorporated herein by reference). Protein synthesis may be performed using manual techniques or by automation. Automated synthesis may be achieved, for example, using Applied Biosystems 431A Peptide Synthesizer (Perkin Elmer). Optionally, fragments of antibodies may be separately synthesized and combined using chemical methods to produce a full-length molecule.

In embodiments where the VH framework is obtained from a non-human animal and used to construct a dAb library, methods for humanization are contemplated. It will be generally appreciated by those skilled in the art that the most critical determinants of antibody selectivity and binding affinity are the sequences and resulting conformations of the complementarity regions (CDRs). Whole antibodies (e.g. human IgG) contain six CDRs, three within the heavy chain variable region (VH) and three within the light chain variable region (VL), for each Fab arm of the complete molecule. The intervening sequences between the CDRs within VH and VL are the framework regions which spacially orient the CDRs. The CDRs together form the antigenic binding sites within antibodies. The critical role of these CDRs in determining the functional properties of antibodies has long been exploited in the processes of antibody humanization and antibody optimization. In the former process, the CDRs from a monoclonal antibody, for example, a mouse antibody, are transferred to a human antibody of similar framework design thereby resulting in an antibody with the same functional properties and reduced immunogenicity in man.

The success of this process is evident from the number of humanized antibodies that have been successfully commercialized as human therapeutics and include HERCEPTIN® (trastuzumab, Genentech, Inc., South San Francisco, Calif.), SYNAGIS® (palivizumab, Medimmune, Inc., Gaithersburg, Md.), CAMPATH® (alemtuzumab, Genzyme Oncology, Cambridge, Mass.), ZENAPAX® (daclizumab, Roche Pharmaceuticlas, Nutley, N.J.), XOLAIR® (omalizumab, Genentech, Inc., South San Francisco, Calif.), RAPTIVA® (efalizumab, Genentech, Inc., South San Francisco, Calif.), AVASTIN® (bevacizumab, Genentech, Inc., South San Francisco, Calif.), and MYLOTARG® (gemtuzumab ozogamicin, Wyeth-Ayerst, Madison, N.J.). Other examples have been described in Singer, et al., (J. Immunol, 150:2844-2857, 1993); Luo, et al., (J. Immunol Meth., 275:31-40, 2002); and Kostelny, et al., (Int. J. Cancer 93; 556-565, 2001).

In principal, a framework sequence from any human antibody may serve as the template for CDR grafting. However, it has been demonstrated that straight CDR replacement onto such a framework often leads to significant loss of binding affinity to the antigen (Glaser, et al., J. Immunol. 149:2606, 1992); Tempest, et al., Biotechnology 9:266, 1992; Shalaby, et al., J. Exp. Med. 17: 217, 1992). The more homologous a human antibody is to the original antibody, the less likely combining the CDRs with the human framework will be to introducing distortions into the CDRs that could reduce affinity. In view of this general principle, it is quite unexpected then that the VH framework of the dAb library of the invention is compatible in terms of domain folding and solubility with such a highly diverse repertoire of CDRs. (See Example 2).

Domain Antibody Modifications

In yet another embodiment, the present invention relates to modified dAbs, and provides methods for modifying domain antibodies identified in accordance with the invention. The modifications may be genetic modifications to the nucleic acid encoding a domain antibody polypeptide of the invention or they may be chemical, structural, or physical modifications made directly to an isolated domain antibody of the invention to impart additional advantageous properties to a domain antibody of the invention regarding, for example, the level of expression, stability, solubility, epitope affinity, antigen neutralization activity, or penetration characteristics, etc.

In one aspect, the present invention contemplates introducing genetic modifications into one or more CDRs or to the framework sequence of the domain antibodies of the invention. Such genetic modifications can confer additional advantageous characterics, i.e. genetic optimization, of the domain antibodies identified from library screening, including, for example, enhanced solubility, enhanced affinity, and enhanced stability. Any type of genetic modification is contemplated by the present invention, including, for example, site-directed mutagenesis, random mutagenesis, insertions, deletions, CDR grafting (i.e. genetic replacement of one CDR for another CDR), and the construction and/or preparation of fusion proteins between domain antibodies of interest and desired fusion partners, e.g., serum albumin-binding peptide (SaAb), which was unexpectedly found to increase the stability of the dAbs of the invention, or soluble CD4, which was unexpectedly found to synergistically impact the neutralization capacity of some of the domain antibodies of the invention. All of these techniques are well known to those skilled in the art. See Ausubel et al., Current Protocols in Molecular Biology, John Wiley & Sons, New York, 2000, incorporated herein by reference. Reference to CDR grafting can be made to Nicaise, et al., Protein Science 13:1882-1891, 2004. The effect of any genetic modification can be tested or screened without undue experimentation using any of the methods described herein or other methods already known to one of ordinary skill in the art. For example, affinity of a domain antibody to a target antigen can be assessed using the herein described BIA procedure.

In another aspect, other modifications contemplated by the present invention relate to chemical modifications of the domain antibodies of the invention to confer additional advantageous features, such as enhanced stability and/or solubility and/or half-life.

In one particular aspect, the domain antibodies of the present invention can be PEGylated, or coupled to polymers of similar structure, function and purpose ("PEG or PEG-like polymers"), to confer enhanced stability and half-life. PEGylation can provide increased half-life and resistance to degradation without a loss in activity (e.g. binding affinity) relative to non-PEGylated antibody polypeptides. The skilled artisan will appreciate, however, that PEGylation may not be advantageous with respect to some targets, in particular, those epitopes which are sterically-obstructed, e.g. CD4i epitope. Thus, in cases where the inventive domain antibody targets a size-restricted epitope, the domain antibody should minimally PEGylated so as not to negatively impact the accessibility of the antibody to the size-restricted antigen. The skilled artisan will appreciate that this general principle should be applied to any modifications made to the dAbs of the invention.

Any method known in the art to couple the domain antibodies of the invention to PEG or PEG-like polymers is contemplated by the present invention. PEG or PEG-like moieties which can be utilized in the invention can be synthetic or naturally occurring and include, but are not limited to, straight or branched chain polyalkylene, polyalkenylene or polyoxyalkylene polymers, or a branched or unbranched polysaccharide, such as a homo- or heteropolysaccharide. Preferred examples of synthetic polymers which can be used in the invention include straight or branched chain poly(ethylene glycol) (PEG), poly(propylene glycol), or poly(vinyl alcohol) and derivatives or substituted forms thereof. Substituted polymers for linkage to the domain antibodies of the invention can also particularly include substituted PEG, including methoxy(polyethylene glycol). Naturally occurring polymer moieties which can be used in addition to or in place of PEG include, for example, lactose, amylose, dextran, or glycogen, as well as derivatives thereof which would be recognized by persons skilled in the art.

PEGylation of the domain antibodies of the invention may be accomplished by any number of means (see for example Kozlowski-A & Harris-J M (2001) Journal of Controlled Release 72:217). PEG may be attached to the domain antibody construct either directly or by an intervening linker. Linkerless systems for attaching polyethylene glycol to proteins is described in Delgado et al., (1992), Crit. Rev. Thera. Drug Carrier Sys. 9:249-304 Francis et al., (1998), Intern. J. Hematol. 68:1-18; U.S. Pat. No. 4,002,531; U.S. Pat. No. 5,349,052; WO 95/06058; and WO 98/32466, the disclosures each of which are incorporated herein by reference. The first step in the attachment of PEG or other polymer moieties to the domain antibody construct of the invention typically is the substitution of the hydroxyl endgroups of the PEG polymer by electrophile-containing functional groups. Particularly, PEG polymers are attached to either cysteine or lysine residues present in the domain antibody construct monomers or multimers. The cysteine and lysine residues can be naturally occurring, or can be engineered into the domain antibody molecule.

One system for attaching polyethylene glycol directly to amino acid residues of proteins without an intervening linker employs tresylated MPEG, which is produced by the modification of monomethoxy polyethylene glycol (MPEG) using tresylchloride. Following reaction of amino acid residues with tresylated MPEG, polyethylene glycol is directly attached to the amine groups. Thus, the invention includes protein-polyethyleneglycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460 discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins are described in WO 98/32466, the entire disclosure of which is incorporated herein by reference.

Other derivatized forms of polymer molecules include, for example, derivatives which have additional moieties or reactive groups present therein to permit interaction with amino acid residues of the domain antibodies described herein. Such derivatives include N-hydroxylsuccinimide (NHS) active esters, succinimidyl propionate polymers, and sulfhydryl-selective reactive agents such as maleimide, vinyl sulfone, and thiol. The reactive group (e.g., MAL, NHS, SPA, VS, or Thiol) may be attached directly to the PEG polymer or may be attached to PEG via a linker molecule.

The size of polymers useful in the invention can be in the range of 500 Da to 60 kDa, for example, between 1000 Da and 60 kDa, 10 kDa and 60 kDa, 20 kDa and 60 kDa, 30 kDa and 60 kDa, 40 kDa and 60 kDa, and up to between 50 kDa and 60 kDa. The polymers used in the invention, particularly PEG, can be straight chain polymers or may possess a branched conformation.

The present invention also contemplates the coupling (either by physical attachment of separate molecules, or through the use of genetic engineering to construct a fusion protein between an antibody of the invention (e.g., m36) and an adduct protein (e.g., serum albumin-binding peptide) of adduct molecules, which can be various polypeptides or fragments thereof which occur naturally in vivo and which resist degradation or removal by endogenous mechanisms. Molecules which increase half life may be selected from the following: (a) proteins from the extracellular matrix, eg. collagen, laminin, integrin and fibronectin; (b) proteins found in blood, e.g., serum albumin, serum albumin-binding peptide (SAbp—e.g., see the fusion prepared in accordance with Example 3), fibrinogen A, fibrinogen B, serum amyloid protein A, heptaglobin, protein, ubiquitin, uteroglobulin, β-2 microglobulin, plasminogen, lysozyme, cystatin C, alpha-1-antitrypsin and pancreatic kypsin inhibitor; (c) immune serum proteins, e.g. IgE, IgG, IgM and their fragments e.g. Fc; (d) transport proteins, e.g. retinol binding protein; (e) defensins, e.g. beta-defensin 1, neutrophil defensins 1, 2 and 3; (f) proteins found at the blood brain barrier or in neural tissues, e.g. melanocortin receptor, myelin, ascorbate transporter; (g) transferrin receptor specific ligand-neuropharmaceutical agent fusion proteins, brain capillary endothelial cell receptor, transferrin, transferrin receptor, insulin, insulin-like growth factor 1 (IGF 1) receptor, insulin-like growth factor 2 (IGF 2) receptor, insulin receptor; (h) proteins localised to the kidney, e.g. polycystin, type IV collagen, organic anion transporter K1, Heymann's antigen; (i) proteins localized to the liver, e.g. alcohol dehydrogenase, G250; (j) blood coagulation factor X; (k) α-1 antitrypsin; (l) HNF 1 α; (m) proteins localised to the lung, e.g. secretory component (binds IgA); (n) proteins localised to the heart, eg. HSP 27; (o) proteins localised to the skin, eg, keratin; (p) bone specific proteins, such as bone morphogenic proteins (BMPs) e.g. BMP-2, -4, -5, -6, -7 (also referred to as osteogenic protein (OP-1) and -8 (OP-2); (q) tumour specific proteins, eg. human trophoblast antigen, herceptin receptor, oestrogen receptor, cathepsins eg cathepsin B (found in liver and spleen); (r) disease-specific proteins, eg. antigens expressed only on activated T-cells: including LAG-3 (lymphocyte activation gene); osteoprotegerin ligand (OPGL) see Kong Y Y et al Nature (1999) 402, 304-309; OX40 (a member of the TNF receptor family, expressed on activated T cells and the only costimulatory T cell molecule known to be specifically up-regulated in human T cell leukaemia virus type-I (HTLV-I)-producing cells—see Pankow R et al J. Immunol. (2000) Jul. 1; 165(1):263-70; metalloproteases (associated with arthritis/cancers), including CG6512 Drosophila, human paraplegin, human FtsH, human AFG3L2, murine ftsH; angiogenic growth factors, including acidic fibroblast growth factor (FGF-1), basic fibroblast growth factor (FGF-2), Vascular endothelial growth factor/vascular permeability factor (VEGF/VPF), transforming growth factor-α (TGF-α), tumor necrosis factor-alpha (TNF-α), angiogenin, interleukin-3 (IL-3), interleukin-8 (IL-8), platelet derived endothelial growth factor (PD-ECGF), placental growth factor (PlGF), midkine platelet-derived growth factor-BB (PDGF), fractalkine; (s) stress proteins (heat shock proteins); and (t) proteins involved in Fc transport.

In a particular aspect, an antibody of the invention, e.g., m36, can be coupled with CD4 or a fragment or mimic thereof to increase the effectiveness of the binding of the antibody with its cognate HIV epitope, e.g., a CD4i epitope. It was also been surprisingly found that soluble CD4 or fragments or mimics thereof can be co-administered with an antibody of interest of the invention (e.g. m36) to synergistically improve the effectiveness of the antibody's neutralization capability. (see Example 3 for further discuss). CD4 mimics are known in the art and can be found described, for example, in U.S. Publication Nos. 2006/0073576, 2008/0096187, each of which are incorporated herein by reference.

In another aspect, the domain antibodies of the invention may be multimerized, as for example, hetero- or homodimers, hetero- or homotrimers, hetero- or homotetramers, or higher order hetero- or homomultimers. Multimerisation can increase the strength of antigen binding, wherein the strength of binding is related to the sum of the binding affinities of the multiple binding sites. The domain antibodies can be multimerized in another aspect by binding to an additional one, two, three or more polypeptide which function to stabilize the dAb against degradation. Such polypeptides may include common blood proteins, such as, albumin, or fragments thereof. Example 3 discusses the construction of m36CH3 as an example of preparing a multimerized antibody of the invention.

In certain aspects, linker may be used to join (either through physical coupling or through a genetic engineering approach) an antibody of the invention, e.g., m36, with a suitable or appropriate adduct molecule or other desired fusion partner. As defined herein, a "fusion partner" can be any molecule, such as an adduct molecule for enhancing the stability of an antibody, that is fused through recombinant means or through physical means to an antibody of interest of the invention.

In yet another aspect, modifications relating to enhancing or modifying antibody activity are contemplated by the present invention. For example, it may be desirable to modify the antibody of the invention with respect to effector function, so as to enhance the effectiveness of the antibody in treating a condition, infection or disorder. For example cysteine residue(s) may be introduced in the domain antibody polypeptide, thereby allowing interchain disulfide bond formation in a multimerized form of the inventive antibodies. The homodimeric or heterodimeric (or multimeric) antibodies may include combinations of the same domain antibody polypeptide chains or different domain antibody polypeptide chains, such that more than one epitope is targeted at a time by the same construct. Such epitopes can be proximally located in the target (e.g. on the HIV target) such that the binding of one epitope facilitates the binding of the multmeric antibody of the invention to the second or more epitopes. The epitopes targeted by multimeric antibodies can also be distally situated.

The invention also contemplates modifying the domain antibodies of the invention to form immunoconjugates comprising the domain antibodies of the invention conjugated to cytotoxic agents, such as a chemotherapeutic agents, toxin (e.g., an enzymatically active toxin of bacterial, fungal, plant or animal origin, or fragments thereof), radioactive isotopes (i.e., a radioconjugate), or antiviral compounds (e.g. anti-HIV compounds).

The term "cytotoxic agent" as used herein refers to a substance that inhibits or prevents the function of cells and/or causes destruction of cells. The term can include radioactive isotopes (e.g., $I_{131}$, $I_{125}$, $Y_{90}$ and $Re_{186}$), chemotherapeutic agents, and toxins such as enzymatically active toxins of bacterial, fungal, plant or animal origin, or fragments thereof.

A "chemotherapeutic agent" is a type of cytotoxic agent useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins, Melphalan and other related nitrogen mustards.

The invention also contemplates immunoconjugation with enzymatically active toxins or fragments thereof. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes.

Where the inventive antibodies are intended to target viruses, bacteria or other pathogens, the invention also contemplates immunoconjugation of the domain antibodies with anti-viral, anti-bacterial or other chemicals and/or compounds that might improve or increase the effectiveness of the domain antibodies of the invention against intended targets, such as, for example, HIV.

For example, the inventive antibodies can be immunoconjugated, or in the alternative, co-administered with, an antibacterial compound, such as, for example, a macrolide (e.g., tobramycin (TOBI®)), a cephalosporin (e.g., cephalexin (KEFLEX®), cephradine (VELOSEF®), cefuroxime (CEFTIN®), cefprozil (CEFZIL®), cefaclor (CECLOR®), cefixime (SUPRAX®) or cefadroxil (DURICEF®), a clarithromycin (e.g., clarithromycin (BIAXIN®)), an erythromycin (e.g., erythromycin (EMYCIN®)), a penicillin (e.g., penicillin V (V-CILLIN K® or PEN VEE K®)) or a quinolone (e.g., ofloxacin (FLOXIN®), ciprofloxacin (CIPRO®) or norfloxacin (NOROXIN®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

In another example, the inventive antibodies can be immunoconjugated, or in the alternative, co-administered with, an antiviral compound, such as, for example, a zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, adefovir, clevadine, entecavir, and pleconaril.

Methods for modifying the domain antibodies of the invention with the various cytoxic agents, chemotherapeutic agents, toxins, antibacterial compounds, and antiviral compounds, etc. mentioned above are well known in the art. For example, immunoconjugates of the antibody and cytotoxic agents can be made using a variety of bifunctional protein coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The domain antibodies can also be modified with useful detectable agents, such as, for example, fluorescent compounds. Exemplary fluorescent detectable agents include fluorescein, fluorescein isothiocyanate, rhodamine, 5-dimethylamine-1-napthalenesulfonyl chloride, phycoerythrin and the like. The domain antibody construct may also be derivatized with detectable enzymes such as alkaline phosphatase, horseradish peroxidase, glucose oxidase and the like. When the domain antibody construct is derivatized with a detectable enzyme, it is detected by adding additional reagents that the enzyme uses to produce a detectable reaction product. The domain antibody construct may also be derivatized with biotin, and detected through indirect measurement of avidin or streptavidin binding.

The skilled artisan will appreciate it may be advantageous to couple any of the aforementioned molecular entities to the domain antibodies of the invention through flexible linkers, such as flexible polypeptide chains. Such linkers may be required to avoid a loss in activity of the domain antibodies, or to avoid sterically restricting the domain antibodies such that they lose their effectiveness in binding to cognate epitopes, in particular, those epitopes which themselves may be sterically restricted, e.g. HIV CD4i epitopes.

Another type of covalent modification contemplated by the present invention involves chemically or enzymatically coupling glycosides to the domain antibodies of the invention. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, CRC Crt. Rev. Biochem., pp. 259-306 (1981).

Removal of any carbohydrate moieties present on the antibodies of the invention may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, et al. Arch. Biochem. Biophys. 259:52 (1987) and by Edge et al. Anal. Biochem., 118:131 (1981). Enzymatic cleavage of carbohydrate moieties on antibodies can be achieved by the use of a variety of endo- and exo-glycosidases as described by Thotakura et al. Meth. Enzymol. 138:350 (1987).

Antigens

The present invention, in another embodiment, relates to antigens of interest that may be used to screen the domain antibody library of the invention to identify useful and effective domain antibodies of the invention.

In one preferred aspect, the antigens of the invention are HIV antigens. The antigens can be from any HIV isolate, e.g. 92UG, Bal, JR-FL, JRCSF, IIIB, 89.6, R2, NL4-3, GXG, Z2Z6, or GXE. The HIV source of antigens can also be from any known clade of HIV, including clade A, B, C, D or E. It will be appreciated that HIV is different in structure from other retroviruses. It is about 120 nm in diameter and roughly spherical. It is composed of two copies of positive single-stranded RNA that codes for nine genes enclosed by a conical capsid composed of 2,000 copies of the viral protein p24. The single-stranded RNA is tightly bound to nucleocapsid proteins, p7 and enzymes needed for the development of the virion such as reverse transcriptase, proteases, ribonuclease and integrase. A matrix composed of the viral protein p17 surrounds the capsid ensuring the integrity of the virion particle. The viral envelope, which forms the outer shell of the virus, is composed of a phospholipid bilayer derived from the membrane of a human cell when outwardly budding from the cell. Embedded in the viral envelope are proteins from the host cell and about 70 copies of the Env "spike" complex. Env consists of a cap made of three molecules called glycoprotein (gp) 120 (gp120) and a stem consisting of three gp41 molecules that anchor the structure into the viral envelope. This glycoprotein complex enables the virus to attach to and fuse with target cells to initiate the infectious cycle.

Regarding the HIV genome, of the nine genes that are encoded within the RNA genome, three of these genes, gag, pol, and env, contain information needed to make the structural proteins for new virus particles. For example, env codes for a protein called gp160 that is broken down by a viral enzyme to form gp120 and gp41. The six remaining genes, tat, rev, nef, vif, vpr, and vpu (or vpx in the case of HIV-2), are regulatory genes for proteins that control the ability of HIV to infect cells, replicate, or cause disease. The protein encoded by nef, for instance, appears necessary for the virus to replicate efficiently, and the vpu-encoded protein influences the release of new virus particles from infected cells. The ends of each strand of HIV RNA contain an RNA sequence called the long terminal repeat (LTR). Regions in the LTR act as switches to control production of new viruses and can be triggered by proteins from either HIV or the host cell.

The HIV antigens can be any of those indicated above, and especially, those for which the neutralization of by antibody would inhibit or cease the virus's ability to replicate, ability to infect cells, ability to assemble, or its ability to process its viral genetic or protein material, etc. In one embodiment, the antigen is the Env protein complex. It will be appreciated that the primary neutralization target on the HIV-1 virion is the envelope glycoprotein (Env), which promotes virus entry by catalyzing fusion between the virion and target cell membranes. Env is a major focus for humoral vaccine and antibody-based immunotherapeutic strategies against HIV-1 (see Parren et al., 2001; Wyatt et al., 1998, for further detail regarding strategies for neutralization by anti-Env antibodies, each of which are incorporated herein by reference). One problem in the art, however, is that efforts to develop effective neutralizing antibodies against Env have been frustrated by the difficulties in eliciting antibodies with potent neutralizing activities against genetically diverse HIV-1 isolates. (Dey et al., 2003).

In a preferred embodiment, the antigen is an inducible antigen. As used herein, the term "inducible antigen" or "inducible epitope" refers to those antigens or epitopes which are present on a polypeptide which, initially are sterically unavailable for antibody interaction, but through the binding of the polypeptide to a second interacting molecule, such as a drug, second polypeptide, ligand, receptor or nucleic acid, becomes exposed as a result of an induced conformational change in the polypeptide caused by the interaction between the polypeptide and the second interacting molecule. In one particular aspect, the inducible antigen is CD4i, which is an antigen comprising an epitope on gp120, the exposure of which is induced by binding to its cognate cellular receptor, CD4. See Labrijn et al., 2003, which is incorporated herein by reference.

While not wishing to be bound by theory, the skilled artisan will appreciate that HIV-1 entry into host cells is initiated by the binding of the gp120 subunit of the viral Env complex (the "spike" complex) to the host cell receptor (CD4). This interaction induces conformational changes in gp120 resulting in the exposure of a conserved high-affinity binding site for the coreceptor (the chemokine receptors CCR5 or CXCR4) (Sattentau et al., 1991; Sattentau et al., 1993).

A second binding step between the gp120-CD4 complex and the coreceptor is then thought to induce additional conformational changes that ultimately result in the fusion of viral and host cell membranes (Dimitrov, 2004; Jones et al., 1991). Not wishing to be bound by theory, neutralizing antibodies are believed to act, at least in part, by binding to the exposed Env surface and obstructing the initial interaction between a trimeric array of gp120 molecules on the virion surface and receptor molecules on the target cell.

In response, HIV-1 has evolved a number of strategies to evade recognition by neutralizing antibodies, particularly those directed to the conserved CD4 and coreceptor binding sites of Env. The extent of protection of these sites from antibody recognition is limited by the necessity to preserve the accessibility for receptor interaction. In the case of the binding site of CD4 to gp120 (the "CD4bs"), this has led to the following structural features: (i) it is partially obscured from antibody recognition by the V1/V2 loop and associated carbohydrate structures; (ii) the flanking residues are variable and modified by glycosylation; (iii) it is recessed to an extent that limits direct access by an antibody variable region; (iv) clusters of residues within the CD4bs that do not directly interact with CD4 are subject to variation among virus strains; (v) many gp120 residues interact with CD4 via main-chain atoms, allowing for variability in the corresponding amino acid side chains; and (vi) there is considerable conformational flexibility within the CD4-unbound state of gp120, and antibody binding therefore requires relatively large entropic decreases, thus "conformationally masking" the conserved CD4bs (Kwong et al., 2002; Myszka et al., 2000).

The coreceptor binding site on gp120 is thought to be composed of a highly conserved element on the β19 strand and parts of the V3 loop (Labrijn et al., 2003). These elements are masked by the V1/V2 variable loops in the CD4-unbound state and largely unavailable for antibody binding (Labrijn et al., 2003). Upon CD4 binding, conformational changes are induced. These changes include displacement of the V1/V2 stem-loop structure and consequent exposure of the coreceptor binding site (Labrijn et al., 2003). Binding studies with variable loop-deleted mutants suggest that CD4 induces additional rearrangement or stabilization of the gp120 bridging sheet near the 19 strand to form the final coreceptor binding surface (Labrijn et al., 2003). Since the binding to CD4 occurs at the virus-cell interface, the exposed coreceptor binding site is optimally positioned for interaction with the coreceptor.

A highly conserved discontinuous structure on gp120 associated with the coreceptor binding site is recognized by monoclonal antibodies (MAbs) that bind better to gp120 upon ligation with CD4. These so-called CD4-induced (CD4i) antibodies, such as 17b and 48d (Labrijn et al., 2003), recognize a cluster of gp120 epitopes that are centered on the 119 strand and partially overlap the coreceptor binding site (Labrijn et al., 2003). Although such CD4i MAbs can neutralize some T-cell line adapted HIV-1 strains, they are generally poorly neutralizing for primary isolates (Labrijn et al., 2003; Poignard et al., 2001). Recently, an antibody Fab fragment, X5, from a phage display library and directed to a CD4i epitope, neutralized a wide variety of primary isolates (Labrijn et al., 2003; Moulard et al., 2002). Also recently, the Fab X5 antibody fragment was studied against other CD4i Mabs at a molecular level and found the smaller fragments were more able to neutralize different HIV-1 isolates (Labrijn et al., 2003).

Accordingly, in one embodiment, the domain antibodies of the present invention bind to or are specifically immunoreactive against the HIV-1 CD4i epitope.

Analytical and Preparative Methods

Once an antibody in accordance with the invention is identified or obtained, for example, by any of the methods herein described, for example, including by panning of the dAb library of the invention and expressing same in a host, it may be preferable to carry out further steps to characterize and/or purify and/or modify the antibody. For example, it may be desirable to prepare a purified, high-titer composition of the desirable antibody or to test the immunoreactivity of the identified antibody. The present invention contemplates any known and suitable methods for characterizing, purifying, or assaying the antibodies of the present invention and it is expected the any person of ordinary skill in the art to which the invention pertains will have the requisite level of technical know-how and resources, e.g. technical manuals or treatises, to accomplish any further characterization, purification and/or assaying of the antibodies of the invention without undue experimentation.

For example, any useful means to describe the strength of binding (or affinity) between a domain antibody of the invention and an antigen of the invention (e.g. CD4i antigen) can be used. For example, the dissociation constant, $K_d$ ($K_d$=k2/k1=[antibody][antigen]/[antibody-antigen complex]) can be determined by standard kinetic analyses that are known in the art. It will be appreciated by those of ordinary skill in the art that the dissociation constant indicates the strength of binding between an antibody and an antigen in terms of how easy it is to separate the complex. If a high concentration of antibody and antigen are required to form the complex, the strength or affinity of binding is low, resulting in a higher $K_d$. It follows that the smaller the $K_d$ (as expressed in concentration units, e.g. molar or nanomolar), the stronger the binding.

Affinity can be assessed and/or measured by a variety of known techniques and immunoassays, including, for example, enzyme-linked immunospecific assay (ELISA), Bimolecular Interaction Analysis (BIA) (e.g., Sjolander and Urbaniczky, Anal. Chem. 63:2338-2345, 1991; Szabo, et al., Curr. Opin. Struct. Biol. 5:699-705, 1995, each incorporated herein by reference), and fluorescence-activated cell sorting (FACS) for quantification of antibody binding to cells that express antigen. BIA is a technology for analyzing biospecific interactions in real time, without labeling any of the interactants (e.g., BIACORE™). BIAcore is based on determining changes in the optical phenomenon surface plasmon resonance (SPR) in real-time reactions between biological molecules, such as, an antibody of the invention and an antigen of interest, e.g. CD4i. References relating to BIAcore technology can be further found in U.S. Published Application Nos: 2006/0223113, 2006/0134800, 2006/0094060, 2006/0072115, 2006/0019313, 2006/0014232, and 2005/0199076, each of which are incorporated herein in their entireties by reference.

The domain antibodies of the invention may be assayed for immunospecific binding by any suitable method known in the art. Assays involving an antibody and an antigen are known as "immunoassays," which can be employed in the present invention to characterize both the antibodies and the antigens of the invention. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety) and can be performed without undue experimentation.

Western blot analysis generally comprises preparing protein samples, electrophoresis of the protein samples in a polyacrylamide gel (e.g., 8% 20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer; blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $_{32}P$ or $_{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1, which is incorporated herein by reference. ELISAs typically comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1, which is incorporated herein by reference.

Any suitable method for purifying antibodies is contemplated herein. For example, chromatographic methods, such as, for example, immuno-affinity chromatography (immobilized ligand to bind and trap antibody of interest), affinity chromatography, protein precipitation, ion exchange chromatography, hydrophobic interaction chromatography, size-exclusion chromatography, as well as electrophoresis, can be found described in the technical literature, for example, in Methods in Enzymology, Volume 182, Guide to Protein Purification, Eds. J. Abelson, M. Simon, Academic Press, $1^{st}$ Edition, 1990, which is incorporated herein by reference. Thus, suitable materials for performing such purification steps, such as chromatographic steps, are known to those skilled in the art. Such methods are suitable for purification of any of the antibodies, antigens or any fragments thereof that are in accordance with the invention as described herein.

Certain embodiments may require the purification or isolation of expressed proteins or antibodies or fragments thereof from a host cell or a portion thereof. Conventional procedures for isolating recombinant proteins from transformed host cells are contemplated by the present invention. Such methods include, for example, isolation of the protein or fragments of interest by initial extraction from cell pellets or from cell culture medium, followed by salting-out, and one or more chromatography steps, including aqueous ion exchange chromatography, size exclusion chromatography steps, high performance liquid chromatography (HPLC), and affinity chromatography may be used to isolate the recombinant protein or fragment. Guidance in the procedures for protein purification can be found in the technical literature, including, for example, Methods in Enzymology, Volume 182, Guide to Protein Purification, Eds. J. Abelson, M. Simon, Academic Press, $1^{st}$ Edition, 1990, which is already incorporated by reference.

Nucleic Acid Molecules, Vectors, and Host Cells

In another aspect, the present invention relates to nucleic acid molecules, e.g. the phagemid clones of the invention, comprising the nucleotide sequences encoding the dAbs of the invention. These nucleic acid molecules may be used, for example, to express quantities of the antibodies for therapeutic or diagnostic use.

Nucleic acid molecules, e.g. phagemid clones, of the present invention may be isolated from host cells, free of other cellular components such as membrane components, proteins, and lipids according to any known or suitable method in the art. Nucleic acid molecules may be isolated using standard nucleic acid purification techniques, or synthesized using an amplification technique such as the polymerase chain reaction (PCR), or by using an automatic synthesizer. Methods for isolating polynucleotides are routine and are known in the art. Any such technique for obtaining a polynucleotide may be used to obtain isolated polynucleotides encoding antibodies of the invention. For example, restriction enzymes and probes may be used to isolate polynucleotides which encode antibodies.

Antibody-encoding cDNA molecules may be made with standard molecular biology techniques, using mRNA as a template. Thereafter, cDNA molecules may be replicated using molecular biology techniques known in the art and disclosed in manuals such as Sambrook, et al., (*Molecular Cloning: A Laboratory Manual,* (Second Edition, Cold Spring Harbor Laboratory Press; Cold Spring Harbor, N.Y.; 1989, Vol. 1-3, incorporated herein by reference). An amplification technique, such as PCR, may be used to obtain additional copies of the polynucleotides.

To express a polynucleotide encoding an antibody, the polynucleotide may be inserted into an expression vector that contains the necessary elements for the transcription and translation of the inserted coding sequence. Methods that are well known to those skilled in the art may be used to construct expression vectors containing sequences encoding antibodies and appropriate transcriptional and translational control elements. These methods include in vitro recombinant DNA techniques, synthetic techniques, and in vivo genetic recombination. Such techniques are described, for example, in Sambrook, et al. (1989) and in Ausubel, et al., (*Current Protocols in Molecular Biology*, John Wiley & Sons, New York, N.Y., 1995, incorporated herein by reference).

A variety of expression vector/host systems may be utilized to contain and express sequences encoding antibodies. These include, but are not limited to, microorganisms, such as bacteria (e.g. *E. coli*) transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV); or bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements may vary in strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUE-SCRIPT phagemid (Stratagene, LaJolla, Calif.), pSPORT1 plasmid (Life Technologies), or the like can be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses may be used. If it is necessary to generate a cell line that contains multiple copies of a nucleotide sequence encoding an antibody, vectors based on SV40 or EBV may be used with an appropriate selectable marker.

General texts describing additional molecular biological techniques useful herein, including the preparation of antibodies include Berger and Kimmel (*Guide to Molecular Cloning Techniques, Methods in Enzymology*, Vol. 152, Academic Press, Inc.); Sambrook, et al., (*Molecular Cloning: A Laboratory Manual*, (Second Edition, Cold Spring Harbor Laboratory Press; Cold Spring Harbor, N.Y.; 1989) Vol. 1-3); *Current Protocols in Molecular Biology*, (F. M. Ausabel et al. [Eds.], Current Protocols, a joint venture between Green Publishing Associates, Inc. and John Wiley & Sons, Inc. (supplemented through 2000)); Harlow et al., (*Monoclonal Antibodies: A Laboratory Manual*, Cold Spring Harbor Laboratory Press (1988), Paul [Ed.]); *Fundamental Immunology*, (Lippincott Williams & Wilkins (1998)); and Harlow, et al., (*Using Antibodies: A Laboratory Manual*, Cold Spring Harbor Laboratory Press (1998)), all of which are incorporated herein by reference.

Use of the dAbs of the Description

In yet another embodiment, the present description provides a pharmaceutical composition comprising an effective amount of the domain antibody of the invention, together with a pharmaceutically acceptable carrier or diluent.

In a particular embodiment, the present invention provides a method for treating and/or preventing an HIV infection by administering an effective amount of the domain antibody, m36 (or derivative thereof) of the invention, together with a pharmaceutically acceptable carrier or diluent. Administration can occur before or after HIV infection.

Some terms relating to the use of the dAbs of this invention are defined as follows.

The term "treatment" includes any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "combination therapy" or "co-therapy" means the administration of two or more therapeutic agents to treat a disease, condition, and/or disorder. Such administration encompasses "co-administration" of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner. The order of administration of two or more sequentially co-administered therapeutic agents is not limited.

The phrase "therapeutically effective amount" means the amount of each agent administered that will achieve the goal of improvement in a disease, condition, and/or disorder severity, and/or symptom thereof, while avoiding or minimizing adverse side effects associated with the given therapeutic treatment.

The term "pharmaceutically acceptable" means that the subject item is appropriate for use in a pharmaceutical product.

The antibodies of this invention are expected to be valuable as therapeutic agents, e.g. anti-HIV antibody based therapies. Accordingly, an embodiment of this invention includes a method of treating and/or preventing a particular condition (e.g. HIV infection) in a patient which comprises administering to said patient a composition containing an amount of an antibody of the invention that is effective in treating the target condition.

The present invention can be used to screen and identify dAb that can be used in the treatment or prevention of a variety of diseases and/or conditions, which include, for example, cancer, such as, carcinomas of the kidney, esophagus, breast, cervix, colon, and lung, and which also includes viral infections (e.g. HIV), bacterial infections, and fungal infections.

The domain antibodies of the present invention may be administered alone or in combination with one or more additional therapeutic agents. Combination therapy includes administration of a single pharmaceutical dosage formulation which contains an antibody of the present invention and one or more additional therapeutic agents, as well as administration of the antibody of the present invention and each additional therapeutic agents in its own separate pharmaceutical dosage formulation. For example, an antibody of the present invention and a therapeutic agent may be administered to the patient together in a single oral dosage composition or each agent may be administered in separate oral dosage formulations.

Where separate dosage formulations are used, the antibody of the present invention and one or more additional therapeutic agents may be administered at essentially the same time (e.g., concurrently) or at separately staggered times (e.g., sequentially). The order of administration of the agents is not limited.

For example, in one aspect, co-administration of a domain antibody or antibody fragment of the invention together with one or more anti-HIV agents to potentiate the effect of either the antibody or the anti-HIV agent(s) or both is contemplated for use in treating HIV infections.

The one or more anti-cancer agents can include any known and suitable compound in the art, such as, for example, chemoagents, other immunotherapeutics, cancer vaccines, anti-angiogenic agents, cytokines, hormone therapies, gene therapies, and radiotherapies. A chemoagent (or "anti-cancer agent" or "anti-tumor agent" or "cancer therapeutic") refers to any molecule or compound that assists in the treatment of a cancer. Examples of chemoagents contemplated by the present invention include, but are not limited to, cytosine arabinoside, taxoids (e.g., paclitaxel, docetaxel), anti-tubulin agents (e.g., paclitaxel, docetaxel, epothilone B, or its analogues), macrolides (e.g., rhizoxin) cisplatin, carboplatin, adriamycin, tenoposide, mitozantron, discodermolide, eleutherobine, 2-chlorodeoxyadenosine, alkylating agents (e.g., cyclophosphamide, mechlorethamine, thioepa, chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP) cisplatin, thio-tepa), antibiotics (e.g., dactinomycin (formerly actinomycin), bleomycin, mithramycin, anthramycin), antimetabolites (e.g., methotrexate, 6-mercaptopurine, 6-thioguanine, cytarabine, flavopiridol, 5-fluorouracil, fludarabine, gemcitabine, dacarbazine, temozolamide), asparaginase, *Bacillus* Calmette and Guerin, diphtheria toxin, hexamethylmelamine, hydroxyurea, LYSODREN®, nucleoside analogues, plant alkaloids (e.g., Taxol, paclitaxel, camptothecin, topotecan, irinotecan (CAMPTOSAR, CPT-11), vincristine, *vinca* alkyloids such as vinblastine), podophyllotoxin (including derivatives such as epipodophyllotoxin, VP-16 (etoposide), VM-26 (teniposide)), cytochalasin B, colchine, gramicidin D, ethidium bromide, emetine, mitomycin, procarbazine, mechlorethamine, anthracyclines (e.g., daunorubicin (formerly daunomycin), doxorubicin, doxorubicin liposomal), dihydroxyanthracindione, mitoxantrone, mithramycin, actinomycin D, procaine, tetracaine, lidocaine, propranolol, puromycin, anti-mitotic agents, abrin, ricin A, *pseudomonas* exotoxin, nerve growth factor, platelet derived growth factor, tissue plasminogen activator, aldesleukin, allutamine, anastrozle, bicalutamide, biaomycin, busulfan, capecitabine, carboplain, chlorabusil, cladribine, cylarabine, daclinomycin, estramusine, floxuridhe, gamcitabine, gosereine, idarubicin, itosfamide, lauprolide acetate, levamisole, lomusline, mechlorethamine, magestrol, acetate, mercaptopurino, mesna, mitolanc, pegaspergase, pentoslatin, picamycin, riuxlmab, campath-1, straplozocin, thioguanine, tretinoin, vinorelbine, or any fragments, family members, or derivatives thereof, including pharmaceutically acceptable salts thereof. Compositions comprising one or more chemoagents (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone.

The chemoagent can be an anti-angiogenic agent, such as, for example, angiostatin, bevacizumab (Avastin®), sorafenib (Nexavar®), baculostatin, canstatin, maspin, anti-VEGF antibodies or peptides, anti-placental growth factor antibodies or peptides, anti-Flk-1 antibodies, anti-Fit-1 antibodies or peptides, laminin peptides, fibronectin peptides, plasminogen activator inhibitors, tissue metalloproteinase inhibitors, interferons, interleukin 12, IP-10, Gro-β, thrombospondin, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, cidofovir, vincristine, bleomycin, AGM-1470, platelet factor 4 or minocycline. Without being bound by theory, the coadministration of an anti-angiogenic agent advantageously may lead to the increase in MN expression in a tumor, thereby making the tumor more susceptible to the antibodies and antibody conjugates of the invention.

In one aspect, said chemoagent is gemcitabine at a dose ranging from 100 to 1000 mg/m$^2$/cycle. In one embodiment, said chemoagent is dacarbazine at a dose ranging from 200 to 4000 mg/m$^2$ cycle. In another aspect, said dose ranges from 700 to 1000 mg/m$^2$/cycle. In yet another aspect, said chemoagent is fludarabine at a dose ranging from 25 to 50 mg/m$^2$/cycle. In another aspect, said chemoagent is cytosine arabinoside (Ara-C) at a dose ranging from 200 to 2000 mg/m$^2$/cycle. In still another aspect, said chemoagent is docetaxel at a dose ranging from 1.5 to 7.5 mg/kg/cycle. In yet another aspect, said chemoagent is paclitaxel at a dose ranging from 5 to 15 mg/kg/cycle. In a further aspect, said chemoagent is cisplatin at a dose ranging from 5 to 20 mg/kg/cycle. In a still further aspect, said chemoagent is 5-fluorouracil at a dose ranging from 5 to 20 mg/kg/cycle. In another aspect, said chemoagent is doxorubicin at a dose ranging from 2 to 8 mg/kg/cycle. In yet a further aspect, said chemoagent is epipodophyllotoxin at a dose ranging from 40 to 160 mg/kg/cycle. In yet another aspect, said chemoagent is cyclophosphamide at a dose ranging from 50 to 200 mg/kg/cycle. In a further aspect, said chemoagent is irinotecan at a dose ranging from 50 to 150 mg/m$^2$/cycle. In a still further aspect, said chemoagent is vinblastine at a dose ranging from 3.7 to 18.5 mg/m$^2$/cycle. In another aspect, said chemoagent is vincristine at a dose ranging from 0.7 to 2 mg/m$^2$/cycle. In one aspect, said chemoagent is methotrexate at a dose ranging from 3.3 to 1000 mg/m$^2$/cycle.

In another aspect, the anti-MN antibodies and/or antibody fragments of the present invention are administered in combination with one or more immunotherapeutic agents, such as antibodies or immunomodulators, which include, but are not limited to, HERCEPTIN®, RETUXAN®, Ova-Rex, Panorex, BEC2, IMC-C225, Vitaxin, Campath I/H, Smart MI95, LymphoCide, Smart I D10, and Oncolym, rituxan, rituximab, gemtuzumab, or trastuzumab.

The invention also contemplates administering the domain antibodies and/or antibody fragments of the present invention with one or more anti-angiogenic agents, which include, but are not limited to, angiostatin, thalidomide, kringle 5, endostatin, Serpin (Serine Protease Inhibitor) anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a β-amino acid peptide corresponding to a fragment of platelet factor-4 (Maione et al., 1990, Cancer Res. 51:2077), a 14-amino acid peptide corresponding to a fragment of collagen I (Tolma et al., 1993, J. Cell Biol. 122:497), a 19 amino acid peptide corresponding to a fragment of Thrombospondin I (Tolsma et al., 1993, J. Cell Biol. 122:497), a 20-amino acid peptide corresponding to a fragment of SPARC (Sage et al., 1995, J. Cell. Biochem. 57:1329-), or any fragments, family members, or derivatives thereof, including pharmaceutically acceptable salts thereof.

Other peptides that inhibit angiogenesis and correspond to fragments of laminin, fibronectin, procollagen, and EGF have also been described (See the review by Cao, 1998, Prog. Mol. Subcell. Biol. 20:161). Monoclonal antibodies and cyclic pentapeptides, which block certain integrins that bind RGD proteins (i.e., possess the peptide motif Arg-Gly-Asp), have been demonstrated to have anti-vascularization activities (Brooks et al., 1994, Science 264:569; Hammes et al., 1996, Nature Medicine 2:529). Moreover, inhibition of the urokinase plasminogen activator receptor by antagonists inhibits angiogenesis, tumor growth and metastasis (Min et al., 1996, Cancer Res. 56:2428-33; Crowley et al., 1993, Proc Natl Acad. Sci. USA 90:5021). Use of such anti-angiogenic agents is also contemplated by the present invention.

In another aspect, the domain antibodies and/or antibody fragments of the present invention are administered in combination with a regimen of radiation.

The domain antibodies and/or antibody fragments of the present invention can also be administered in combination with one or more cytokines, which includes, but is not limited to, lymphokines, tumor necrosis factors, tumor necrosis factor-like cytokines, lymphotoxin-ca, lymphotoxin-β, interferon-β, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Pas ligand, 4-1BBL, endothelial monocyte activating protein or any fragments, family members, or derivatives thereof, including pharmaceutically acceptable salts thereof.

The domain antibodies and/or antibody fragments s of the present invention can also be administered in combination with a cancer vaccine, examples of which include, but are not limited to, autologous cells or tissues, non-autologous cells or tissues, carcinoembryonic antigen, alpha-fetoprotein, human chorionic gonadotropin, BCG live vaccine, melanocyte lineage proteins (e.g., gp100, MART-1/MelanA, TRP-1 (gp75), tyrosinase, widely shared tumor-associated, including tumor-specific, antigens (e.g., BAGE, GAGE-1, GAGE-2, MAGE-1, MAGE-3, N-acetylglucosaminyltransferase-V, p15), mutated antigens that are tumor-associated (β-catenin, MUM-1, CDK4), nonmelanoma antigens (e.g., HER-2/neu (breast and ovarian carcinoma), human papillomavirus-E6, E7 (cervical carcinoma), MUC-1 (breast, ovarian and pancreatic carcinoma). For human tumor antigens recognized by T-cells, see generally Robbins and Kawakami, 1996, Curr. Opin. Immunol. 8:628. Cancer vaccines may or may not be purified preparations.

In yet another embodiment, the domain antibodies and/or antibody fragments of the present invention are used in association with a hormonal treatment. Hormonal therapeutic treatments comprise hormonal agonists, hormonal antagonists (e.g., flutamide, tamoxifen, leuprolide acetate (LUPRON), LH-RH antagonists), inhibitors of hormone biosynthesis and processing, and steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), and antiandrogens (e.g., cyproterone acetate).

The antibodies described herein may be provided in a pharmaceutical composition comprising a pharmaceutically acceptable carrier. The pharmaceutically acceptable carrier may be non-pyrogenic. The compositions may be administered alone or in combination with at least one other agent, such as stabilizing compound, which may be administered in any sterile, biocompatible pharmaceutical carrier including, but not limited to, saline, buffered saline, dextrose, and water. A variety of aqueous carriers may be employed including, but not limited to saline, glycine, or the like. These solutions are sterile and generally free of particulate matter. These solutions may be sterilized by conventional, well-known sterilization techniques (e.g., filtration).

Generally, the phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the antibody compositions of the invention.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compositions may contain pharmaceutically acceptable auxiliary substances as required to approximate physiological conditions such as pH adjusting and buffering agents, and the like. The concentration of the antibody of the invention in such pharmaceutical formulation may vary widely, and may be selected primarily based on fluid volumes, viscosities, etc., according to the particular mode of administration selected. If desired, more than one type of antibody may be included in a pharmaceutical composition (e.g., an antibody with different $K_d$ for MN binding).

The compositions may be administered to a patient alone, or in combination with other agents, drugs or hormones. In addition to the active ingredients, these pharmaceutical compositions may contain suitable pharmaceutically acceptable carriers comprising excipients and auxiliaries that facilitate processing of the active compounds into preparations which may be used pharmaceutically. Pharmaceutical compositions of the invention may be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

The compositions of the invention additionally contemplate suitable immunocarriers, such as, proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein-derived or non-protein derived substances are known to those skilled in the art.

Formulations suitable for parenteral, subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000). Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The determination of a therapeutically effective dose is well within the capability of those skilled in the art. A therapeutically effective dose refers to the amount of an antibody that may be used to effectively treat a disease (e.g., cancer) compared with the efficacy that is evident in the absence of the therapeutically effective dose.

The therapeutically effective dose may be estimated initially in animal models (e.g., rats, mice, rabbits, dogs, or pigs). The animal model may also be used to determine the appropriate concentration range and route of administration. Such information may then be used to determine useful doses and routes for administration in humans.

Therapeutic efficacy and toxicity (e.g., $ED_{50}$—the dose therapeutically effective in 50% of the population and $LD_{50}$—the dose lethal to 50% of the population) of an antibody may be determined by standard pharmaceutical procedures in cell cultures or experimental animals. The dose ratio of toxic to therapeutic effects is the therapeutic index, and it may be expressed as the ratio, $LD_{50}/ED_{50}$. The data obtained from animal studies may used in formulating a range of dosage for human use. The dosage contained in such compositions may be within a range of circulating concentrations that include the $ED_{50}$ with little or no toxicity. The dosage varies within this range depending upon the dosage form employed, sensitivity of the patient, and the route of administration.

The exact dosage may be determined by the practitioner, in light of factors related to the patient who requires treatment. Dosage and administration may be adjusted to provide sufficient levels of the antibody or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy.

The antibodies of the invention may also be administered by introducing genetically engineered bacteria which express and release the domain antibodies of the invention once the bacteria a present in the patient. This format might be suitable for treating HIV infections. The antibody-expressing bacteria can be introduced into mucus membranes of the throat, for example, or in other mucosal regions in which HIV might be found. Methods for constructing and/or engineering such recombinant bacteria are well known in the art.

Polynucleotides encoding antibodies of the invention may be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 500 µg/kg of patient body weight. For administration of polynucleotides encoding the antibodies, effective in vivo dosages are in the range of about 100 ng to about 500 µg of DNA.

The antibodies of the present invention can also be delivered in a microsphere or microsome bodies.

The mode of administration of antibody-containing pharmaceutical compositions of the present invention may be any suitable route which delivers the antibody to the host. As an example, pharmaceutical compositions of the invention may be useful for parenteral administration (e.g., subcutaneous, intramuscular, intravenous, or intranasal administration, or microsomal or lipid microsome bodies).

The above disclosure generally describes the present invention. A more complete understanding can be obtained by reference to the following specific examples, which are provided for purposes of illustration only and are not intended to limit the scope of the invention.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1. Identification of VH Framework

Figure 4:
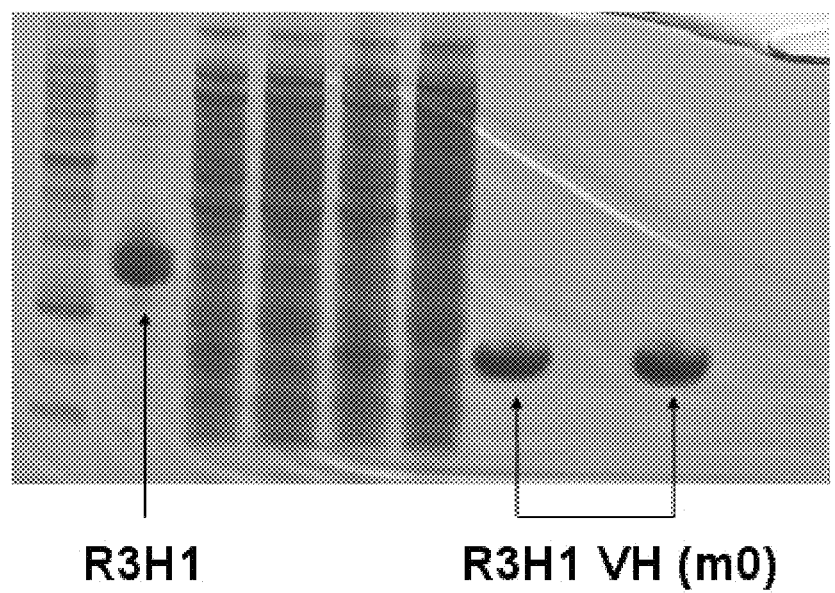
FIG. 4 is a photograph of an SDS-PAGE gel showing the R3H1 Fab and its VH domain, m0, of the invention. The VH domain, m0, was identified by panning a human naïve antibody library, which had been recently constructed according to the procedure and primers described in (de Haard H J et al. 1999. J. Biol. Chem. 274:18218-30) but with one-step overlapping PCR cloning (Zhu Z and Dimitrov D S, in press, Therapeutic antibodies, A. Dimitrov, Ed., Methods in Molecular Biology, Humana Press), with an HIV-1 antigen, recombinant soluble Env with truncated transmembrane portion and cytoplasmic tail—gp140. The R3H1 Fab was identified with a stop codon in the light chain, after which its reading frame was corrected. The VH domain of R3H1 was sub-cloned into a phagemid vector, expressed and purified.

A naïve human Fab library ($1.5\times10^{10}$ members) was constructed from peripheral blood B cells of 22 healthy donors, spleens of 3 donors, and lymph nodes of healthy 34 donors. This library was used for selection of Fabs against HIV-1 antigen gp140 which was conjugated to magnetic beads (Dynabeads M-270 epoxy; DYNAL Inc., New Hyde Park, N.Y.) as described (Zhu Z et al. J Virol. 2006, 80(2):891-9). Amplified libraries of $3.8\times10^{12}$ phage-displayed Fabs were incubated with 20, 20, 10, and 10 µg of gp140 in 1 ml volume for 2 h at room temperature during the first, second, third, and fourth rounds of biopanning, respectively. After incubation the beads were washed 5 times for the first round and 10 times for the later rounds with PBST to remove nonspecifically bound phages. Bound phages were rescued by mixing the beads with *E. coli* TG1 cells for 45 min at 37° C. and a phage library was prepared for the next round of biopanning. Ninety five clones were randomly picked from the infected TG1 cells in the third and fourth round, respectively, and subjected to monoclonal phage-based enzyme-linked immunosorbent assay (monoclonal phage ELISA). A positive Fab, designated R3H1, was identified with a stop codon in the light chain. Its reading frame was corrected subsequently. R3H1 was expressed and purified as shown in FIG. 4.

The gene fragment of R3H1 VH domain (m0) was amplified from R3H1 Fab phagemid and subcloned into phagemid vector (e.g. pComb3x or pZYD). The phagemids containing m0 genes were prepared and transformed to *E. coli* HB2151 chemical competent cells. Soluble m0 were expressed and purified as described (Zhu Z et al. J Virol. 2006, 80(2):891-9). The SDS-PAGE of purified m0 was shown in FIG. 4. The amino acid and nucleotide sequences of m0 are shown in FIGS. 5A and 5B.

Example 2. Construction and Screening of Domain Antibody Library

Highly diverse antibody libraries have become important sources for selection of antibodies with high affinity and novel properties. Combinatorial strategies provide efficient ways of creating antibody libraries containing a large number of individual clones. These strategies include the reassembly of naturally occurring genes encoding the heavy and light chains from either immune or nonimmune B-cell sources and introduction of synthetic diversity to either the framework regions (FRs) or the complementarity determining regions (CDRs) of the variable domains of antibodies.

This Example describes the identification of a human heavy chain-only antibody and its use as a scaffold for construction of a phage-displayed VH library as well as an approach to introduce genetic diversity in this library in which natural human CDR2, CDR3, and synthetic CDR1 repertoires are combined into a single human VH framework scaffold. The usefulness of the library has been demonstrated by the successful selection of high-affinity binders to viral and cancer-related antigens.

The following methods and materials were employed in this Example. The results of this Example are subsequently discussed below.

Methods and Materials:

Amplification of CDR Repertoire and FR Fragments

Primers used for PCR amplification of gene fragments are described in Table 1, below.

TABLE 1

Primers used for PCR amplification of gene fragments.

| Primer description | Name | Sequence | Target |
|---|---|---|---|
| H1 antisense | H1R | 5'-GCG GAC CCA GCT CAT TTC ATA AKM AKM GAA AKM GAA AKM AGA GGC TGC ACA GGA GAG (SEQ ID NO: 5)$^c$ | CDR1 |
| H1 sense | H1-F | 5'-GAG GAG GAG GAG GAG GCG GGG CCC AGG CGG CCC AGG TGC AGC TGG TGC-3' (SEQ ID NO: 6) | CDR1 |
| H2 sense | H2F1 | 5'-GAA ATG AGC TGG GTC CGC CAG GCT CCA GGA CAA SGS CTT GAG TGG (SEQ ID NO: 7) | VH1-2$^a$, VH1-3, VH1-8, VH1-18, VH1-45, VH1-46, VH1-58, VH1-69, VH1-C, VH6-1, VH7-*$^b$ |
| | H2F2 | GAA ATG AGC TGG GTC CGC CAG GCT CCA GGG AAG GCC CTG GAG TGG (SEQ ID NO: 8) | VH2-* |
| | H2F3 | 5'-GAA ATG AGC TGG GTC CGC CAG GCT CCA GGG AAG GGN CTR GAG TGG (SEQ ID NO: 9) | VH1-24, VH1-F, VH3-*, VH4-*, VH5-* |
| H2 antisense | H2R1 | ATT GTC TCT GGA GAT GGT GAC CCT KYC CTG RAA CTY (SEQ ID NO: 10) | VH1-* |
| | H2R2 | 5'-ATT GTC TCT GGA GAT GGT GAA TCG GCC CTT CAC NGA (SEQ ID NO: 11) | VH3-*, VH6-1 |
| | H2R3 | 5'-ATT GTC TCT GGA GAT GGT | VH2-*, VH4-* |

TABLE 1-continued

Primers used for PCR amplification of gene fragments.

| Primer description | Name | Sequence | Target |
|---|---|---|---|
| | | GAC TMG ACT CTT GAG GGA (SEQ ID NO: 12) | |
| | H2R4 | 5'-ATT GTC TCT GGA GAT GGT GAC STG GCC TTG GAA GGA (SEQ ID NO: 13) | VH5-* |
| | H2R5 | 5'-ATT GTC TCT GGA GAT GGT AAA CCG TCC TGT GAA GCC (SEQ ID NO: 14) | VH7-* |
| H3 sense | H3F1 | 5'-ACC CTG AGA GCC GAG GAC ACR GCY TTR TAT TAC TGT (SEQ ID NO: 15) | VH3-9, VH3-20, VH3-43 |
| | H3F2 | 5'-ACC CTG AGA GCC GAG GAC ACA GCC AYR TAT TAC TGT (SEQ ID NO: 16) | VH1-45, VH2-*, VH5-*, VH7-81 |
| | H3F3 | 5'-ACC CTG AGA GCC GAG GAC ACR GCY GTR TAT TAC TGT (SEQ ID NO: 17) | Other than above |
| H3 antisense | H3R | 5'-GTG GCC GGC CTG GCC ACT TGA GGA GAC GGT GAC C (SEQ ID NO: 18) | FR4 |
| FR3 sense | FR3F | 5'-ACC ATC TCC AGA GAC AAT TCC (SEQ ID NO: 19) | FR3 |
| FR3 antisense | FR3R | 5'-GTC CTC GGC TCT CAG GGT G (SEQ ID NO: 20) | FR3 |
| Extension #1 | FR1F | 5'-TGG TTT CGC TAC CGT GGC CCA GGC GGC CCA GGT GCA GCT GGT G (SEQ ID NO: 21) | FR1 |
| Extension #2 | HISR | 5'-GTC GCC GTG GTG GTG GTG GTG GTG GCC GGC CTG GCC ACT TG (SEQ ID NO: 22) | 5' end of H3R primer |

[a] Sub-groups of human antibody heavy chain genes.
[b] All members in the groups.
[c] Underlined codons indicates primer degeneracy.

Figure 6:
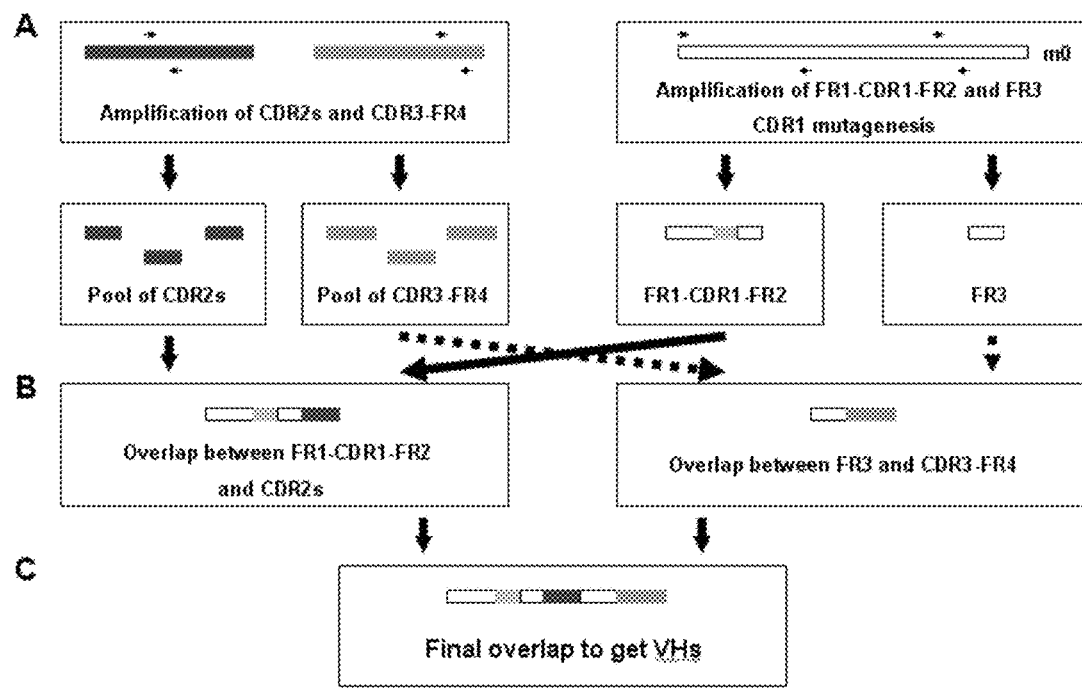
FIG. 6 illustrates a process of constructing the VH library, which comprises the m0 framework and a diversity of CDR sequences from different sources. The VH library was constructed in three steps. In the first step, PCRs were performed to amplify CDR2 and CDR3 gene segments from various antibody libraries (plasmid DNA containing human antibody gene fragments). CDR2 amplification products from different libraries were pooled. Similarly, CDR3 amplification products generated from different libraries were pooled together. The CDR1 segment was prepared by PCR amplification from a m0 template using the degenerate primer H1R covering the entire length of CDR1 to generate mutations at four positions to A, D, S or Y. The FR3 segment was also obtained from m0 for assembly of entire VHs. In the second step, overlapping PCRs were performed to join CDR1s to CDR2s and FR3 to CDR3s, respectively. In the third step, entire VHs were assembled by overlapping PCR of the products of the second step. The products were cloned into a phagemid vector and a library was obtained by performing electroporations as described in the Examples.

For amplification of CDR1 repertoire and FR3 fragment, the master human VH m0, as described in Example 1 and shown in FIGS. 5A and 5B, was used as the template. The degenerate primer H1R (see Table 1) enables randomization of four amino acids in CDR1 to A/D/S/Y. Three non-immune (IgM-derived from healthy non-infected non-immunized donors) human antibody phage display libraries that have recently been constructed according to the procedure described previously (de Haard H J et al. 1999. J. Biol. Chem. 274:18218-30) and one immune (IgG-derived from HIV-infected donors) library constructed from HIV patients have been used as templates for amplification of CDR2 and CDR3 repertoires (See FIG. 6A). The libraries used included (a) a naïve human Fab library ($5 \times 10^9$ members) constructed from peripheral blood B cells of 10 healthy donors (Zhu et al., J. Virol., 2006, which is incorporated herein by reference); (b) a naïve human Fab library ($1.5 \times 10^{10}$ members) constructed from peripheral blood B cells of 22 healthy donors, spleens of 3 donors, and lymph nodes of healthy 34 donors (de Haard H J et al. 1999. J. Biol. Chem. 274:18218-30); (c) a naïve human Fab library ($7.2 \times 10^8$ members) constructed from cord blood of 2 healthy babies (essentially the procedure and primers described in (de Haard H J et al. 1999. J. Biol. Chem. 274:18218-30) were used but with one-step overlapping PCR cloning (Zhu Z and Dimitrov D S, in press, Therapeutic antibodies, A. Dimitrov, Ed., Methods in Molecular Biology, Humana Press; and (d) an immune human Fab library constructed from bone marrow obtained from 3 long-term nonprogressors whose sera exhibited the broadest and most potent HIV-1 neutralization among 37 HIV-infected individuals (Zhang et al., J. Immunol. Methods, 2003). To maintain maximal diversity, 8 first round PCR reactions were carried out using different primer combinations of Table 2 against each of the above libraries as a template to obtain CDR2 product repertoire. Similarly, 3 first round PCR reactions were carried out using different primer combinations of Table 2 against each of the above libraries as a template to obtain CDR3 product repertoire.

TABLE 2

Primer pairings used for first round amplification of gene segments

| Primer pairings | Products | Targets |
|---|---|---|
| FR1F-H1R | FR1-CDR1-FR2[a] | CDR1 |
| H2F1-H2R1 | FR2[a]-CDR2-FR3[a] | VH1-* (except VH1-24, VH1-F) |
| H2F1-H2R2 | FR2[a]-CDR2-FR3[a] | VH6-1 |
| H2F1-H2R5 | FR2[a]-CDR2-FR3[a] | VH7-* |
| H2F2-H2R3 | FR2[a]-CDR2-FR3[a] | VH2-* |
| H2F3-H2R1 | FR2[a]-CDR2-FR3[a] | VH1-24, VH1-F |
| H2F3-H2R2 | FR2[a]-CDR2-FR3[a] | VH3-* |
| H2F3-H2R3 | FR2[a]-CDR2-FR3[a] | VH4-* |
| H2F3-H2R4 | FR2[a]-CDR2-FR3[a] | VH5-* |
| H3F1-H3R | FR3[a]-CDR3-FR4 | VH3-9, VH3-20, VH3-43 |
| H3F1-H3F2 | FR3[a]-CDR3-FR4 | VH1-45, VH2-*, VH5-*, VH7-81 |
| H3F1-H3F3 | FR3[a]-CDR3-FR4 | Other than above |
| FR3F-FR3R | FR3 | FR3 |

[a]These products partially cover FRs.

PCRs were performed in a volume of 50 μl using High Fidelity PCR Master (Roche, Cat. #12140314001), 500 pM of each primer and 0.5 μg of template DNA (e.g. VH m0 or the four antibody phage display libraries described above) for 30 cycles (45 sec at 94° C.; 45 sec at 55° C.; and 1 min at 72° C.). Products for each primer combination from one template were pooled, purified from 2% agarose gel using QIAquick Gel Extraction Kit (Qiagen, Cat. #28706), and quantified by reading the optical density (O.D.) at 260 nm (1 O.D. unit=50 μg/ml). Finally, all products from the four antibody phage display library templates were pooled at a molarity ratio calculated by counting the number of donors for template libraries, e.g. 10:59:2:3.

Assembly of Complete VH Domain Antibodies

The primers used in the first round of PCR created identical sequences in the downstream regions of the CDR1 products, the upstream regions of CDR3 products, and both the downstream and the upstream regions of the CDR2 products. These identical sequences are homologous to FRs and serve as the overlap for the second- and third-round extension PCR reactions.

In the second-round PCR extension reactions (see FIG. 6B), CDR1 fragments containing the whole FR1 and partial FR2 on both sides were joined to the CDR2 fragments containing partial FR2 and partial FR3 on both sides by overlapping PCRs performed in a volume of 100 μl using both templates (in the same molarities) for 7 cycles in the absence of primers and additional 15 cycles in the presence of primers (500 pM of FR1F and 500 pM of H2R1-5 mixture). Under the same condition, FR3 fragments were joined to CDR3 fragments containing partial FR3 and the whole FR4 on both sides by overlapping PCRs using primers FR3F and H3R.

In the third-round extension (see FIG. 6C), complete VHs were formed by annealing the products of the second-round extension reactions to each other using overlapping PCRs with the extension primers HISR and FR1F appended with SfiI restriction sites.

Preparation of VH Domain Library

Gel-purified VH products formed above were digested with SfiI (New England BioLabs, Inc., Cat. #R0123L), and cloned into a phagemid vector. The SfiI-digested and gel-purified VH fragments and phagemid vectors, 80 μg and 230 μg respectively, were ligated in an 8-ml reaction mixture with 10000 units of T4-DNA ligase (New England BioLabs, Inc., Cat. #M0202L) at 16° C. for 72 h. The ligation products were then desalted and concentrated by passing through a 4-ml Amicon Ultra-4 centrifugal filter with a cutoff of 3000 MW (Millipore, Cat. #UFC800324) at 4000×g for 20 minutes at room temperature and washing 3 times with 4 ml of distilled water. About 100-μl of ligation product was recovered from the filter and stored at −20° C. for later use.

Electroporation was then performed. For electroporations, 1 L of 2YT medium containing 1% glucose (w/v) was pre-warmed at 37° C. 100 gene pulser cuvettes (Bio-Rad, Cat. #165-2089) with 1 mm gap were chilled on ice. The desalted ligation product and 4 ml of E. coli strain TG1 electroporation-competent cells (Stratagene, Cat. #200123) were thawed together on ice. The TG1 competent cells were divided into 10 pre-chilled 1.5-ml Eppendorf tubes in 400 μl aliquots. Ten μl of ligation product was added to each tube and gently mixed by pipet action. Next, 41 μl of mixture was transferred to each electroporation cuvette, which was gently tapped on the bench to move the mixture to the bottom of the cuvette. Electroporations were performed at 1.8 kV, 25 μF, and 200Ω and the cuvettes were flushed immediately with 1 ml and then twice with 2 ml of pre-warmed 2YT medium and transferred into a 2-L flask.

After completing all electroporations, 700 ml of pre-warmed 2YT medium was added to each flask to make a volume of 1 L in total. The cultures were incubated at 37° C. with shaking at 250 rpm for 30 min. Ten μl of the culture was 10-fold serially diluted in 100 μl of 2YT medium, and plated on 2YT agar plates containing 2% glucose (w/v) and 100 μg/ml of ampicillin. The plates were incubated overnight at 37° C. The total number of transformants was calculated by counting the number of colonies, multiplying by the culture volume, and dividing by the plating volume.

For preparation of the phage display library, 1 ml of 100 mg/ml ampicillin was added to the 1-L culture and the culture was then incubated with shaking for additional 2 h at 37° C. The cell density was measured by reading the O.D.600 of the culture and the total number of cells was calculated by multiplying the O.D.600 value by $5 \times 10^8$ (estimated number of cells in 1 ml culture when O.D.600 reaches 1) and the culture volume (1000 in this case). The culture was infected with 10 M.O.I. of M13KO7 helper phage (New England BioLabs, Cat. #N0315S) and incubated at 37° C. for 30 min, shaking for homogenization every 10 min. The cells were collected by centrifuging at 5000 rpm for 10 min and resuspended in 2-L 2YT medium containing 100 µg/ml of ampicillin and 50 µg/ml of kanamycin. Following incubation at 250 rpm overnight at 30° C., the culture was centrifuged at 5000 rpm for 15 min at 4° C.

The phagemids were prepared from the bacterial pellet using the Qiagen HiSpeed Plasmid Maxi Kit (Cat. #12663). For phage precipitation, the supernatant was transferred to 2 clean 2-L flasks, mixed well with ¼ volume of PEG8000 (20%, w/v)/NaCl (2.5 M) solution, and incubated on ice for 3 h. The mixture was centrifuged at 14000×g for 20 min at 4° C. and the phage pellet was resuspended in 100 ml 1×PBS, pH7.4 by pipetting up and down along the side of the centrifuge bottles with a 10-ml pipet. The phage suspension was centrifuged at 5000 rpm for 10 min at 4° C. The supernatant was transferred to a clean 200 ml flask, mixed well with ¼ volume of PEG8000 (20%, w/v)/NaCl (2.5 M) solution, and incubated on ice for 1 h. The mixture was centrifuged at 14000×g for 20 min at 4° C. and the phage pellet was resuspended in 50 ml 1×PBS, pH7.4. The phage suspension was centrifuged at 5000 rpm for 10 min at 4° C. and the supernatant was transferred to a clean 200 ml flask. The concentration of phage was measured by reading O.D.280 (1 O.D.280=$2.33 \times 10^{12}$/ml). For long-term storage, the phages were mixed with the same volume of autoclaved glycerol, aliquoted to make sure that each contains phage particles at least 100 times of the total number of transformants, and stored at −80° C.

Sequence Diversity Analysis

To evaluate sequence diversity of the VH domain library, clones were randomly selected from the library and sequenced. The amino acid sequences were deduced from those clones with complete nucleotide sequences. For analysis of CDR1 sequence diversity, the frequency of A/D/S/Y usage in each position mutated was calculated (see FIG. 8A).

The origins of CDR2s were determined and the numbers of mutations in amino acid sequences were calculated by comparing to the germlines of human VHs from IMGT database (imgt.cines.fr/textes/IMGTrepertoire/Proteins/protein/human/IGH/IGHV/Hu_IGHVallgenes.htm 1). The FR sequences on both sides of CDR2, e.g. residue #53-55 (IMGT numbering) and residue #70-76, are highly diversified among 7 groups of human VH germlines, thus, could be used as markers in addition to CDR2 sequences themselves to determine CDR2 origins. See FIGS. 8B and 8C.

The length of CDR3 was calculated one by one and the length distribution was compared to that of human heavy chain CDR3 in vivo. The pairing between CDR2 origins and lengths of CDR3 was also plotted. See FIG. 8D.

Measurement of VH Folding

The folding of phage-displayed VHs with a fixed VH3 scaffold was measured by their ability binding to protein A.

The use of Protein A as a marker for proper folding of human VH3 is well known. The library of ~$10^{13}$ phage particles was blocked in 2% non-fat dry milk in PBS for 1 h at room temperature and passed through a chromatography column (Bio-Rad, Cat. #731-1550) loaded with 300 ml of nProtein A Sepharose 4 Fast Flow (GE Healthcare, Cat. #17-5280-02). The column was washed 3 times with 10 ml of PBS containing 0.05% (v/v) Tween-20 (PBST) each. Bound phages were eluted by incubation at room temperature for 10 min with 1 ml of 100 mM acetic acid (pH 3.0) followed by neutralization with 0.1 ml of 1 M Tris-HCl (pH 9.0). Eluted phage were rescued by infection of E. coli TG1 cells and a phage library was prepared for the next round of selection. In the fourth round of selection, TG1 cells were infected with the eluted phages, serially diluted and plated on 2YT agar plates. Clones were randomly selected from these plates and sequenced. The origins of CDR2s were determined as described above.

Panning the Library to Screen for Domain Antibodies of Interest

The library of ~$10^{13}$ phage particles was blocked in 1 ml PBS containing 2% non-fat dry milk and incubated with 10 µg of gp120-CD4, 5 µg of gp140, 5 µg of gp120-CD4, and 5 µg of gp140 conjugated to magnetic beads (Dynabeads M-270 epoxy, Invitrogen, Cat. #143-01) for 2 h at room temperature during the first, second, third and fourth rounds of biopanning, respectively. After incubation the beads were washed 5 times for the first round and 15 times for the later rounds with PBST to remove nonspecifically bound phages. Bound phage were rescued by mixing the beads with E. coli TG1 cells for 45 min at 37° C. and a phage library was prepared for the next round of biopanning. Clones were randomly picked from the infected TG1 cells in the third and fourth round and subjected to monoclonal phage-based enzyme-linked immunosorbent assay (monoclonal phage ELISA) to identify clones of phage displaying VHs with binding activity as described (Zhu et al., J. Virol., 2006, which is incorporated herein by reference).

Each of the selected clones was inoculated into 100 µl of 2YT medium containing 100 µg/ml ampicillin and 0.2% glucose in 96-well plates. When the bacterial cultures reached an O.D. 600 of 0.5, 50 µl of fresh 2YT medium containing helper phage M13KO7 at M.O.I. of 10 and kanamycin at 50 µg/ml (final concentration) was added to each well, and the plates were further incubated at 30° C. overnight in a shaker at 250 rpm. 50 µl of each phage supernatant was moved to a Corning high-binding 96-well plate (Sigma, Cat. #CLS3690) coated with 1 µg/ml of gp120-CD4 and blocked with 3% non-fat dry milk in PBS, and incubated for 2 h at room temperature. The plates were washed 4 times with PBST and incubated with 50 µl of horse radish peroxidase (HRP)-conjugated anti-M13 antibody (GE Healthcare, Cat. #27-9421-01) 1:5000 diluted in PBS at room temperature for 1 h. After incubation the plates were washed 4 times with PBST and 50 µl of substrate solution ABST (Roche, Cat. #1684302) was added to each well. The solution absorbance at 405 nm (A405) was measured following incubation at 37° C. for 15-30 min.

Expression and Purification of VH Domain Antibodies

The selected clones resulting from the panning and screening process, each phagemid clone containing a VH gene of interest, were prepared and transformed into E. coli HB2151 chemical competent cells. These selected phagemid clones were referred to as c3, c6, d1, d7, b4, c11, d10, b3, b5 (also referred to herein as m36), b7, g6 and e11. Soluble VHs were expressed as described previously (Zhu et. al., J. Virol., 2006, which is incorporated herein by reference). The bacterial pellet was collected after centrifugation at 8000×g for 10 min and resuspended in PBS buffer containing 0.5 mU polymixin B (Sigma, Cat. #P0972). After 30 min incubation with rotation at 50 rpm at room temperature, it was centrifuged at 25000×g for 25 min at 4° C., and the supernatant was used for Hexahistidine-tagged VH purification by immobilized metal ion affinity chromatography (IMAC) using Ni-NTA resin (Qiagen, Cat. #30230) according to manufacturer's protocols (which are incorporated herein by reference). The purity of each VH was determined by running SDS-PAGE (see FIG. 7 or FIG. 11C) and measuring O.D. at 280.

Binding of Soluble VH Domain Antibodies

ELISA was performed by using Corning high-binding 96-well plates coated with 1 µg/ml of antigens and blocked with 3% non-fat dry milk in PBS. Microplate wells were then inoculated with 50 µl of serially diluted soluble VHs for 2 h at room temperature. After 4 washes with PBST, FLAG-tagged VHs were detected by adding 50 µl of 1:5000 diluted HRP-conjugated anti-FLAG antibody (Sigma, Cat. #A8592) to each well. Following incubation with the antibody for 1 h at room temperature, the plates were washed 4 times with PBST and the assay was developed at 37° C. with ABST substrate and monitored at 405 nm as described.

Measurement of VH Domain Antibody Oligomerization

Superdex75 column was calibrated with protein molecular mass standard of 13.7 (ribonuclease A), 25 (chymotrypsin), 44 (ovalbumin), 67 (albumin), 158 (aldolase), 232 (catalase), 440 (ferritin) and 669 (thyroglobulin) kDa. Purified VH domain antibodies in PBS were loaded onto the column that had been pre-equilibrated with PBS. The proteins were eluted with PBS at 0.5 ml/min.

Pseudovirus Neutralization Assay

Viruses pseudotyped with Envs from HIV-1 primary isolates representing HIV-1 group M, clades A-E (4) were used in this study. Briefly, pseudotyped viruses were prepared by cotransfection of 70-80% confluent 293T cells with pNL4-3.luc.E-R- and pSV7d-env plasmid using the Poly-Fect transfection reagent, according to manufacturer's instruction (Qiagen, Cat. #301105). Pseudotyped viruses were obtained after 24 h by centrifugation and filtration of cell culture through 0.45-µm filters, mixed with different concentrations of antibodies for 1 h at 37° C., and then added to $1.5 \times 10^4$ HOS-CD4-CCR5 cells grown in each well of 96-well plates. Luminesence was measured after 2 days, using the Bright-Glo Luciferase Assay System (Promega, Cat. #E2610) and a LumiCount microplate luminometer (Turner Designs). Mean relative light units (RLU) for triplicate wells were determined. Percentage inhibition was calculated by the following formula: (1—average RLU of antibody-containing wells/average RLU of virus-only wells)×100. $IC_{50}$ and $IC_{90}$ of neutralization were assigned for the antibody concentration at which 50% and 90% neutralization were observed, respectively.

A more detailed description of the specific materials that could be employed in carrying out the methods of Example 2 are outlined as follows. Equivalent materials can be employed as will be understood by one of ordinary skill in the art. This specific listing of materials is not meant to limit the present invention in any way.

Detailed List of Materials:

The following list of materials were used in connection with the human VH genes and phagemid vectors
1. VH framework m0 is shown in FIG. 20A.
2. Phagemid vector is shown in FIG. 20B.

The following list of materials were used in connection with the isolation of lymphocytes.

1. Defibrinated or anticoagulant-treated human peripheral blood stored at 4° C. was used as soon as possible. Total RNA, PolyA+ RNA, and cDNA of human blood and other immune tissues such as bone marrow, spleen, and lymph node are commercially available, e.g. from Clontech.
2. Ficoll-Paque Plus regents (Amersham Bioscience, Piscataway, N.J.) were used.
3. Solution A: 0.1% (w/v) anhydrous D-glucose, 0.05 mM $CaCl_2$, 0.98 mM $MgCl_2$, 5.4 mM KCl, and 145 mM Tris was used. To prepare, Solution A was dissolved in approximately 950 ml double distilled water ($ddH_2O$) and add 10 N HCl until pH is 7.6. The volume was adjusted to 1 L with $ddH_2O$.
4. Solution B: 140 mM NaCl in $ddH_2O$ was used.
5. Balanced salt solution (ready to use) was employed. To prepare, 1 volume of Solution A was mixed with 9 volumes of Solution B. The balanced salt solution should be prepared fresh each week. Equivalent salt solution may be employed, e.g., phosphate buffer solution (PBS), pH 7.4.
6. Eppendorf centrifuge 5804R (Eppendorf, Westbury, N.Y.) was used for centrifugation. Any equivalently refrigerated centrifuge producing up to at least 400 g and maintaining temperature of 18-20° C. may be employed.
7. BD Falcon™ Conical Tubes (BD Biosciences, San Jose, Calif.) we used. Any equivalent tubes with a volume of ~15 ml and internal diameter ~1.3 cm may be used.
8. Pasteur pipettes, 3 ml, were used.
9. Hemacytometer (Sigma, St. Louis, Mo.) was used.
10. 0.4% trypan blue stain (Sigma, St. Louis, Mo.) was used.

The following list of materials were used in connection with the isolation of total RNA and the synthesis of cDNA.
1. RNeasy Mini Kits (Qiagen, Valencia, Calif.) were employed.
2. QIAshredder (Qiagen, Valencia, Calif.) kits were employed.
3. SuperScript. III First-Strand Synthesis System for RT-PCR (Invitrogen, Carlsbad, Calif.) was employed.
4. Corning® PCR tubes, free of RNase and DNase (Sigma, St. Louis, Mo.) were employed.
5. 1.5 ml Eppendorf tubes, treated with distilled water containing 0.05% (v/v) DEPC at 37° C. overnight, dried in an oven, and autoclaved, were employed.
6. Ultra pure water (Quality Biologicals, Gaithersburg, Md.), free of RNase and DNase was employed.
7. Eppendorf centrifuge 5417R (Eppendorf, Westbury, N.Y.), or other refrigerated centrifuges with adapters for 1.5 ml Eppendorf centrifugal tubes were employed.
8. Bio-Rad PTC-100 thermal cycler (Bio-Rad, Hercules, Calif.) was employed. Any equivalent thermal cycler with a hot bonnet heated lid may be employed.

The following list of materials were used in connection with the PCR amplification of CDRs and FRs and the assembly of entire VHs.
1. High Fidelity PCR Master (Roche, Indianapolis, Ind.) was used. Other high-fidelity PCR systems may be used.
2. Primers for PCR amplification of CDRs can be found in Table 1 above. It is noted that to construct a highly diverse antibody library, it is essential for the primers to be able to cover as many human antibody genes as possible. To design those primers, it is necessary to possess some sequence information and try to understand how human antibody genes are organized. It is further noted that the products of CDR1 primers and CDR2 primers will cover FR1 and FR2, respectively, so that there are only four fragments instead of six (FR1-3 and CDR1-3) for the entire VH assembly. The number of fragments for assembly should be reduced to help decrease reading frame shifts. It was found that highly efficient digestion of VH products with restriction enzymes is critical for the construction of a large library. PCR amplification using the extension primers will result in long overhangs at both 5' and 3' ends of VH products so that there is an obvious difference in length change after digestion with restriction enzyme SfiI, which can be observed clearly on agarose gel.

The following list of materials were used in connection with the digestion of VHs and ligation of VHs with phagemids.
 1. Restriction enzymes SfiI, 20000 units/ml (BioLabs, Ipswich, Mass.) were used.
 2. T4 DNA Ligase, 400000 units/ml (BioLabs, Ipswich, Mass.) was used.

The following list of materials were used in connection with the concentration and desalting of ligations.
 1. Centrifugal filter: Amicon Ultra-4 with a cutoff of 3000 MW (Millipore, Billerica, Mass.).

The following list of materials were used in connection with cell electroporations.
 1. TG1 electroporation-competent cells (Stratagene, La Jolla, Calif.).
 2. Gene Pulser/MicroPulser Cuvettes (Bio-Rad, Hercules, Calif.).
 3. Gene Pulser (Bio-Rad, Hercules, Calif.)

The following list of materials were used in connection preparing the VH library.
 1. 2YT medium: 0.5% (w/v) NaCl, 1% (w/v) yeast extract, 1.6% (w/v) tryptone in distilled water. Autoclaved and stored at room temperature.
 2. 20% (w/v) glucose in distilled water. Sterilized using 0.22 μm pore size filter (Nalgene, Rochester, N.Y.).
 3. M13KO7 helper phage (BioLabs, Ipswich, Mass.).
 4. Antibiotics: 100 mg/ml ampicillin and 100 mg/ml kanamycin.

A more detailed description of the specific methods that could be employed in Example 2 are outlined as follows. Equivalent methods can be employed as will be understood by one of ordinary skill in the art. This specific listing of methods is not meant to limit the present invention in any way.

Detailed List of Methods:

To construct a high-quality (high diversity, low mutation rate, and very few of reading frame shifts) antibody library, it is important to optimize each step before next step can be performed.

Lymphocyte Isolation by Ficoll-Paque Plus Regents
 1. To a 15 ml BD Falcon tube, add 2 ml of defibrinated or anticoagulant-treated blood and 2 ml of balanced salt solution. Mix by drawing the blood and buffer in and out of a Pasteur pipette. Note that tissue culture plasticware or pretreated glassware should be used. All glassware which comes in contact with the samples should be siliconized before use. The glassware should be immersed in a 1% silicone solution for 10 seconds, washed with distilled water (6 times) and then dried in an oven.
 2. Invert the Ficoll-Paque Plus bottle several times to ensure thorough mixing. Pipette 3 ml of the reagents into a new 15 ml BD Falcon tube. Carefully layer the diluted blood sample (4 ml) onto the Ficoll-Paque Plus. When layering the sample do not mix the regents and the diluted blood sample.
 3. Centrifuge at 400 g for 30-40 minutes at 18-20° C. Note that it is important to maintain exactly 18-20° C. temperature in the centrifuge. Lower temperature will result in precipitates in the layer of plasma making the lymphocyte layer unclear. Optimization of the duration of centrifuging is also recommended to yield a clear lymphocyte layer. This can be accomplished through a practice using irrelevant blood samples. After centrifugation, generally four layers can be clearly observed including plasma, lymphocyte, Ficoll-Paque Plus, and granulocyte/erythrocyte layer from top to bottom, respectively. Draw off the upper layer of plasma using a clean Pasteur pipette, leaving the lymphocyte layer undisturbed at the interface.
 4. Transfer the lymphocyte layer to a clean 15 ml BD Falcon tube using a clean Pasteur pipette. It is critical to remove the entire interface but with a minimum amount of Ficoll-Paque Plus and plasma. Removing excess plasma causes contamination by platelets and plasma proteins. Removing excess Ficoll-Paque Plus results in unnecessary granulocyte contamination.
 5. Add at least 3 volumes of balanced salt solution to the lymphocytes. Suspend the cells by gently drawing them in and out of a Pasteur pipette.
 6. Centrifuge at 400 g for 10 minutes at 18-20° C. Remove the supernatant and resuspend the lymphocytes in 6-8 ml balanced salt solution by pipetting them gently in and out.
 7. Determine the number of living cells by using hemacytometer: Mix 50 μl cell suspension with 50 μl trypan blue stain, load 20 μl of the mixture to the hemacytometer, count the total number of living cells (i.e., the unstained cells, since only the live cells have intact membrane that is not permeable for the dye), and calculate the total cell quantity according to the hematocytometer instructions.
 8. Centrifuge the cell suspension at 400 g for 10 minutes at 18-20° C. Remove the supernatant. The lymphocyte pellet can be used immediately for RNA extraction or stored at −80° C. for later use.

Extraction of Total RNA from Lymphocytes

To extract the total RNA we used RNeasy Mini Kit from Qiagen following the basic protocol provided by the manufacturer. Note that this kit provides enrichment for mRNA by eliminating most RNAs shorter than 200 nucleotides such as 5.8S rRNA, 5S rRNA, and tRNAs. Thus, it may be more efficient for the products to be retro-transcribed to cDNA. Below are described a few modifications in this protocol that may improved the yield and quality of the extracted RNA.
 1. Thaw the lymphocyte pellet at room temperature if it is stored at −80° C. Note that the lymphocytes should not be frozen but used for RNA extraction directly. Also it will be better for RNA products to be retro-transcribed to cDNA without freeze-thaw cycle. Finish these steps within one day. Gently tap the bottom of the tube containing the lymphocyte pellet on the bench to loosen the cells.
 2. Disrupt cells (up to 5×10$^6$) by addition of 350 μl of Buffer RLT from RNeasy Mini Kit. Note that there are limitations with the capacity of the buffer to lyse the cells and the binding capacity of the column. Thus, it is important to use appropriate number of cells in order to obtain optimal RNA yield and purity. Vortex or pipet to mix.

3. Pipet the lysate directly onto a QIAshredder spin column placed in a 2 ml collection tube, and centrifuge for 2 min at 12000×rpm.
4. Add 1 volume of 70% ethanol to the homogenized lysate and mix well by pipetting. Do not centrifuge.
5. Apply all sample, including any precipitate that may have formed, to an RNeasy mini column placed in a 2 ml collection tube. Centrifuge for 15 s at 10000×rpm. Discard the flow-through.
6. Add 700 μl Buffer RW1 to the RNeasy column. Centrifuge for 15 s at 10000×rpm. Discard the flow-through and collection tube.
7. Transfer the RNeasy column into a new 2 ml collection tube. Pipet 500 μl Buffer RPE onto the RNeasy column. Centrifuge for 15 s at 10000×rpm. Discard the flow-through.
8. Add another 500 μl Buffer RPE to the RNeasy column. Centrifuge for 2 min at 10000×rpm to dry the membrane in the column.
9. Transfer the RNeasy column to a new 1.5 ml collection tube. Pipet 30-50 μl RNase-free water onto the membrane in the column. Centrifuge for 1 min at 10000×rpm to elute. Store the RNA product at −80° C. and use it quickly.

Retro-Transcription of RNAs to cDNAs

These instructions assume the use of SuperScript™ III First-Strand Synthesis System from Invitrogen. The following procedure is designed to convert total RNA (5 μg to 25 μg) or mRNA (5 μg to 2.5 μg) into first-strand cDNA.
1. Mix and briefly centrifuge each component in the kit before use.
2. Prepare two RNA/primer mixtures, one with oligo $(dT)_{20}$ and the other with random hexamers, in 0.2 ml Corning® PCR tubes by combining the following:

| | |
|---|---|
| 3. Total RNA | x μl (up to 25 μg) |
| 4. 50 μM oligo $(dT)_{20}$ or | 5 μl |
| 5. 50 ng/μl random hexamers | |
| 6. 10 mM dNTP mix | 5 μl |
| 7. DEPC-treated water | 40-x μl |
| 8. Total | 50 μl |

Incubate at 65° C. for 5 min, then place on ice for at least 1 min.
3. During the incubation, set up two tubes containing the same cDNA synthesis mixtures by adding each component in the indicated order:

| | |
|---|---|
| 1. 10 × RT buffer | 10 μl |
| 2. 2.5 mM $MgCl_2$ | 20 μl |
| 3. 0.1M DTT | 10 μl |
| 4. RNase OUT ™ (40 u/μl) | 5 μl |
| 5. Superscript ™ III RT (200 u/μl) | 5 μl |
| 6. Total | 50 μl |

Figure 21:
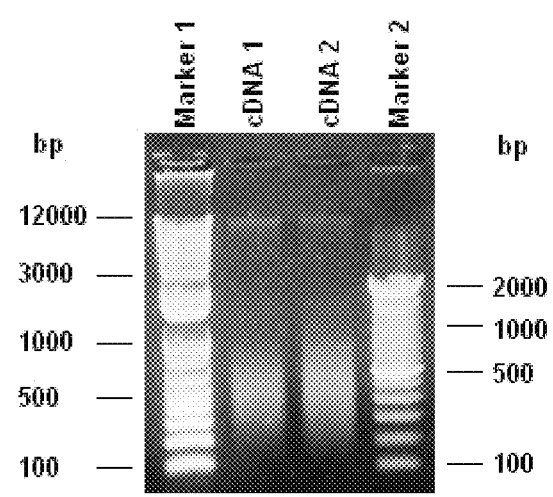
FIG. 21 shows the preparation of cDNA by reverse transcription of total RNA from human peripheral blood mononuclear cells. Total RNA was extracted from human mononuclear cells with RNeasy Mini Kit (Qiagen, Cat. #74104) as described below in Example 2. Using a SuperScript III First-Strand Synthesis System (Invitrogen, Cat. #18080-051) containing oligo $(dT)_{20}$ primers and random hexamers, total RNA was then reverse transcribed into cDNA. The cDNA products were separated on a 0.8% (w/v) agarose gel. The cDNA 1 and cDNA 2 are from reactions using oligo $(dT)_{20}$ primers and random hexamers, respectively. Two molecular weight DNA mass markers, Marker 1 (Invitrogen Cat. #15628-019) and Marker 2 (Invitrogen Cat. #10787-018) were included.

4. Add 50 μl cDNA synthesis mixtures to the 50 μl RNA/primer mixtures, mix gently, and collect by brief centrifugation. Incubate as follows:
For oligo $(dT)_{20}$ primer: 50 min at 50° C.
For random hexamer primer: 10 min at 25° C., followed by 50 min at 50° C.
5. Terminate the reactions at 85° C. for 5 min. Chill on ice.
6. Collect the reactions by brief centrifugation add 5 μl of RNase H to each reaction, and incubate for 20 min at 37° C.
7. Run a 0.8% (w/v) agarose gel using 2 μl of the reaction to simply check the amount and length distribution of cDNA. An example of the results produced is shown in FIG. 21. The cDNA reactions are combined and stored at −20° C. for further use.

PCR Amplification of CDRs and FRs
1. First Round of PCR to Get CDR2s
To amplify the CDR2s from cDNA samples, perform eight amplifications. Set up one PCR tube for each primer combination as the following:

| | |
|---|---|
| 1. $ddH_2O$ | 23-x μl |
| 2. 2 × High Fidelity PCR Master | 25 μl |
| 3. Forward primer (25 μM) | 1 μl |
| 4. Reverse primer (25 μM) | 1 μl |
| 5. cDNA | x μl (~1 μg) |
| 6. Total | 50 μl |

Primer Recombinations:
H2-F1/H2-R1; H2-F1/H2-R2; H2-F1/H2-R5; H2-F2/H2-R3; H2-F3/H2-R1; H2-F3/H2-R2; H2-F3/H2-R3; H2-F3/H2-R4

Perform the PCR under the following conditions:
1. Step 1: 4 min at 94° C. for initial denaturation
2. Step 2: 45 sec at 94° C.; 45 sec at 55° C.; 1 min at 72° C. (30 cycles)
3. Step 3: 5 min at 72° C.

Run the products separately on a 2% agarose gel to check the specific amplification of CDR2s. An example of the results produced is shown in FIG. 22A. Cut out the correct-sized bands on the gel and purify the DNA using, for example, QIAquick Gel Extraction Kit (Qiagen, Cat. #28706). Running the eight products separately on the gel is strongly recommended to make observation. When different templates are used, products may not be observed on the gel for one or two primer combinations. This should be due to very limited number of templates for the specific primer combinations so it is not necessary to repeat the reaction. However, it is recommended to cut out the correct-sized gel and purify the limited number of DNA for these primer combinations as is done to those with clear bands. This essentially helps maintain the diversity of the repertoires. Then, pool the purified DNA and quantify it by reading the optical density (O.D.) at 260 nm (1 O.D. unit=50 μg/ml). Store the sample at −20° C. for later use.

2. First Round of PCR to Get CDR3s
Three amplifications are performed to obtain CDR3. Set up the reaction for each primer combination and perform the PCR as it is described above for CDR2 amplification except for the use of different primers.
Primer Combinations: H3-F1/H3R; H3-F2/H3R; H3-F3/H3R Run the products separately on a 2% agarose gel to check the specific amplification of CDR3s. An example of the results produced is shown in FIG. 22B. Purify the DNA. Note that when running the CDR3 products on 2% agarose gel, the bands will not be so sharp due to their highly diverse lengths. Thus, cut as wide a gel as you can to make sure it covers those CDR3s with long or short lengths. Next, pool and quantify it by reading the optical density (O.D.) at 260 nm (1 O.D. unit=50 μg/ml). Store the sample at −20° C. for later use.

3. First Round of PCR to Get CDR1s
Only one reaction is needed for CDR1 amplification as the following.

| | |
|---|---|
| 1. ddH$_2$O | 46-x µl |
| 2. 2 × High Fidelity PCR Master | 50 µl |
| 3. H1-F (25 µM) | 2 µl |
| 4. H1-R (25 µM) | 2 µl |
| 5. m0 | x µl (~0.1 µg) |
| 6. Total | 100 µl |

Perform the PCR under the same conditions as for the CDR2 amplification. At least 1 µg of purified DNA is required in order to proceed further.

4. First Round of PCR to Get FR3

Only one reaction is needed for FR3 amplification as the following

| | |
|---|---|
| 1. ddH$_2$O | 46-x µl |
| 2. 2 × High Fidelity PCR Master | 50 µl |
| 3. FR3-F (25 µM) | 2 µl |
| 4. FR3-R (25 µM) | 2 µl |
| 5. m0 | x µl (~0.1 µg) |
| 6. Total | 100 µl |

Perform the PCR under the same conditions as for the CDR2 amplification. At least 1 µg of purified DNA is required in order to proceed further.

Assembly of Entire VHs

1. Perform a Second Round of PCR (Overlap Extension) to Get CDR1s and CDR2s Together The primers in the first round of PCR create identical sequences in the downstream regions of the CDR1s and the upstream regions of CDR2s. These identical sequences serve as the overlap for the second-round extension.

Set up a reaction without primers as the following. The CDR1s and CDR2s should be added in the same molarities.

| | |
|---|---|
| 1. ddH$_2$O | 46-x-y µl |
| 2. 2 × High Fidelity PCR Master | 50 µl |
| 3. CDR1s | x µl (~100 ng) |
| 4. CDR2s | y µl (~120 ng) |
| 5. Total | 100 µl |

Perform the PCR under the following conditions:
1. Step 1: 4 min at 94° C. for initial denaturation
2. Step 2: 45 sec at 94° C.; 45 sec at 55° C.; 1 min at 72° C. (7 cycles)
3. Step 3: 5 min at 72° C.

After the cycling, add primers to the reaction: 2 µl H1-F (25 µM) and 2 µl H2-R1-5 mixture (25 µM). Then perform another 15 cycles of PCR under the same condition. Note that other than the major correct-sized fragments, this procedure could generate minor nonspecific products for some reasons. Optimization is may be helpful to minimize nonspecific amplification. Increasing the annealing temperature from 55° C. to 60° C. and reducing the number of cycles from 7 to 5, 15 to 12 before and after addition of primers, respectively, may help.

2. Second Round of PCR (Overlap Extension) to Get FR3 and CDR3s Together

The procedure is almost the same as above except the use of different gene fragments and primers for overlap. The reaction after addition of primers contains the following:

| | |
|---|---|
| 1. ddH$_2$O | 46-x-y µl |
| 2. 2 × High Fidelity PCR Master | 50 µl |
| 3. FR3 | x µl (~100 ng) |
| 4. CDR3s | y µl (~120 ng) |
| 5. FR3-F (25 µM) | 2 µl |
| 6. H3-R (25 µM) | 2 µl |
| 7. Total | 100 µl |

Run the products on a 2% agarose gel, purify the DNA, and quantify it. At least 2 µg each of the purified CDR1-CDR2 and FR3-CDR3 DNA is required to proceed.

3. Third Round of PCR (Final Overlap Extension) to Get Whole-Length VHs.

Also, the procedure is almost the same as above except the use of resultant gene fragments from Step 1 (CDR1-CDR2) and 2 (FR3-CDR3) above, and extension primers for overlap. The reaction after addition of primers contains the following:

| | |
|---|---|
| 1. ddH$_2$O | 46-x-y µl |
| 2. 2 × High Fidelity PCR Master | 50 µl |
| 3. CDR1-CDR2 | x µl (~100 ng) |
| 4. FR3-CDR3 | y µl (~100 ng) |
| 5. H1-F (25 µM) | 2 µl |
| 6. HISR | 2 µl |
| 7. Total | 100 µl |

Run the products on a 2% agarose gel, purify the DNA with gel extraction kit (elute the DNA with ultra pure water in this step instead of elution buffer provided with the kit), and quantify it. At least 50 µg of purified VHs is needed to make a library with a size of up to $10^{10}$. If the yields are too low, repeat the final overlap PCR and pool the end products.

Digestion of VHs and Phagemid Vector, and Ligation of Same

1. Digestion of VHs and Phagemid Vector

The reaction for VH digestion should contain:

| | |
|---|---|
| 1. ddH$_2$O | 870-x µl |
| 2. 10 × Buffer 2 | 100 µl |
| 3. VHs | x µl (up to 50 µg) |
| 4. SfiF (20 units/µl) | 20 µl |
| 5. BSA | 10 µl |
| 6. Total | 1000 µl |

Set up two reactions for phagemid digestion. Each should contain:

| | |
|---|---|
| 1. ddH$_2$O | 870-x µl |
| 2. 10 × Buffer 2 | 100 µl |
| 3. Phagemid vectorphagemid vector | x µl (up to 100 µg) |
| 4. SfiF (20 units/µl) | 20 µl |
| 5. BSA (100×) | 10 µl |
| 6. Total | 1000 µl |

Incubate both digests at 50° C. for 3 hours. Run the digested products on agarose gels (2% for VHs and 1% for phagemids), purify the DNA with gel extraction kit (elute the DNA with ultra pure water), and quantify it. Note that the digestion of phagemid vectors may not be complete due to quality of DNA. To address this problem, additional treatment may be needed to further purify the phagemids before digestion, or use more SfiI to digest for longer time, for example, overnight.

2. Ligation of VHs with Phagemid Vector.

Before large-scale ligation can be performed, it is recommended to test the ligations. One test can be to assess the suitability of the vector and inserts for high-efficiency ligation and transformation. This can be accomplished through assembling small reactions either with vector only (test for vector self-ligation) or with both vector and insert, and transforming chemical competent cells like DH5α. Another test can be to determine the optimal ratio between insert and vector for the highest efficiency of ligation. This can be accomplished through assembling small reactions with insert and vector in different morality ratios such as 3:1, 2:1, and 1:1, and transforming chemical competent cells. The highest ligation efficiency may be obtained by using insert in two-fold molar excess.

Assemble the reaction as the following:

| | |
|---|---|
| 1. ddH$_2$O | 1750-x-y μl |
| 2. 10 × T4 ligase buffer | 200 μl |
| 3. SfiI-digested VHs | x μl (~30 μg) |
| 4. SfiI-digested pCom3bX | y μl (~90 μg) |
| 5. T4 ligase (200 units/μl) | 50 μl |
| 6. Total | 2000 μl |

Incubate at 16° C. for 72 hours.

Concentration and Desalting of Ligated Products

Concentrate and desalt the reactions by passing through a 4 ml Amicon Ultra-4 centrifugal filter with a cutoff 3000 MW:

1. Add all 2000 μl reactions into the filter; centrifuge at 4000×g for 20 minutes at room temperature, Remove the flow-through to a 15 ml Falcon tube (do not discard the flow-through at this moment just in case most of DNA is lost due to the broken membrane of the filter).
2. Add 3.5 ml ultra pure water into the filter and centrifuge under the same condition for 30 min, remove the flow-through to a 15 ml Falcon tube.
3. Repeat Step 2 at least twice. Note that the desalting of DNA samples is an important step to the success of electroporations. High concentration of ions in the DNA solution will result in a long and intense pulse in electroporations, which causes cell damage or rupture. At least 1000-time dilution of DNA solution can be needed to generate time constants of 4.6-5.0 s in electroporations that generally gave the highest efficiency. In the last repeat, centrifuge for a longer time, making sure that about 50 μl reactions remain in the filter.
4. Gently pipette the reactions and remove them to a 1.5 ml Eppendorf tube, store at −20° C. for later use.

Electroporations and Preparation of Library

1. Pre-warm 1 L 2YT medium containing 1% glucose (w/v) at 37° C. Chill 50 gene pulser cuvettes on ice. At the same time thaw, on ice, the desalted ligations and 2 ml of TG1 electroporation-competent cells.
2. Divide 2 ml of TG1 competent cells into 5 pre-chilled 1.5 ml Eppendorf tubes with 400 μl each. Add 10 μl ligations to each tube and pipet gently to mix. Transfer 41 μl mixtures to each cuvette. Gently tap the cuvette on the bench to make the mixture fill out the bottom of the cuvette.
3. Electroporate at 1.8 kV, 25 μF, and 200Ω. Flush the cuvette immediately with 1 ml and then twice with 2 ml of pre-warmed 2YT medium and combine the 3 ml in a 2 L flask. After all electroporations are completed, add 850 ml pre-warmed 2YT medium left to the flask.
4. Shake at 250 rpm for 30 min at 37° C. Serially dilute 10 μl of the culture in 100 μl of 2YT medium, and spread on LB agar plates containing 2% glucose (w/v) and 100 μg/ml of ampicillin. Incubate the plates overnight at 37° C. Calculate the total number of transformants by counting the number of colonies, multiplying by the culture volume, and dividing by the plating volume.
5. Add 1 ml of 100 mg/ml ampicillin to the 1-L culture and shake for additional 2 hours at 37° C.
6. Take 1 ml of the culture and measure the cell density by reading O.D.600. Calculate the total number of cells by multiplying the O.D.600 value by $5 \times 10^8$ (estimated number of cells in 1 ml culture when O.D.600 reaches 1) and the culture volume (1000 in this case). Add 10 M.O.I. of M13KO7 helper phage to the culture. Incubate at 37° C. for 30 min, shaking for homogenization every 10 min.
7. Spin down the cells at 5000 rpm for 10 min. Resuspend in 2 L 2YT medium containing 100 μg/ml of ampicillin and 50 μg/ml of kanamycin. Incubate at 250 rpm overnight at 30° C.
8. Spin at 5000 rpm for 15 min at 4° C. Save the bacterial pellet for phagemid preparation using, for example, the Qiagen HiSpeed Plasmid Maxi Kit. For phage precipitation, transfer the supernatant to a clean 2 L flask and add ¼ volume of 20% (w/v) PEG8000 and 2.5 M NaCl solution. Mix well and incubate on ice for at least 1 h.
9. Spin at 14000 g for 20 min at 4° C. Discard the supernatant. Resuspend the phage pellet in 50 ml PBS, pH7.4 by pipetting up and down along the side of the centrifuge bottle by using a 10-ml pipette.
10. Spin at 5000 rpm for 10 min at 4° C. Transfer the supernatant to a clean 200 ml flask and add ¼ volume of 20% (w/v) PEG8000 and 2.5 M NaCl solution. Mix well and incubate on ice for 1 h.
11. Spin at 14000 g for 20 min. Discard the supernatant. Resuspend the phage pellet in 50 ml PBS, pH7.4.
12. Spin at 5000 rpm for 10 min at 4° C. Transfer the supernatant to a clean 200 ml flask.
13. Add the same volume of autoclaved glycerol and mix well.
14. Measure the concentration of phage by reading O.D.280 (1 O.D.280=$2.33 \times 10^{12}$/ml). Aliquot the phage to make sure that each contains phage particles at least 100 times of the total number of transformants (calculated in step 4). Store the phage at −80° C. The phage library is now ready for panning.

Example 2 Results

Design of the VH Library

To obtain a diverse VH library, an approach that grafts all three CDRs from several sources to the framework scaffold of m0 could have been taken. However, the estimated diversity of such an approach could be more than $10^{12}$ after recombination among three CDRs, which is difficult for artificially created phage display libraries to reach. This Example took the approach of mutating one of the CDRs, while grafting in the remaining CDRs from a variety of different sources. Given that the CDR1s were relatively more conserved in both their sequences and their lengths, this Example focused on grafting in CDR2s and CDR3s from a variety of sources, while randomly mutating four putative solvent-accessible positions of the CDR1 of m0 to A/D/S/Y (the solvent-accessible positions being amino acid residue #27, 29, 31 and 32 under the IMGT numbering system) (see FIGS. 5A and 5B) in the original CDR1 of m0 to A/D/S/Y.

In order to access as many different human VH gene segments as possible, a new set of primers (see Table 1) was designed for amplification of CDR2 and CDR3 repertoires, respectively, based on human VH germline sequences loaded in the IMGT database (imgt.cines.fr/textes/IMG-Trepertoire/Proteins/alleles/human/HuAl_list.html). The target sequences (see italicized nucleotide sequences flanking CDR2 and CDR3 regions in the m0 template of FIGS. 5A and 5B) for these primers are mostly conserved within each group of germlines. Thus, these primers, in combination with each other (see Table 2), should allow efficient amplification of all commonly used human VH gene segments.

To make the resultant library more suited for selection of antibodies against a wide range of antigens including, pathogen and cancer-related antigens, an IgM-derived library from cord blood was used as a template additionally, which we assumed should provide more naïve CDR repertoires. Given the special case of HIV-1, which has mostly evolved to escape the human immune system, an immune library from HIV-1 patients was also used.

Construction of the VH Library

The VH library was constructed in three steps. In the first step, 8 and 3 PCRs were performed for amplification of CDR2 and CDR3 gene segments from each library template, respectively (see FIG. 6A). Products of CDR2s from different libraries were pooled. Products of CDR3 amplifications were also pooled. CDR1 repertoire was amplified from m0 master VH using a degenerate primer covering the whole CDR1. FR3 segment was also obtained from m0 for assembly of entire VHs. In the second step, overlapping PCRs were performed to join CDR1s to CDR2s and FR3 to CDR3s, respectively (see FIG. 6B). In the third step, entire VHs were assembled from the products of the second step by overlapping PCR (see FIG. 6C). The products were cloned into phagemid vectors and a library of around $2.5 \times 10^{10}$ members was obtained by performing 100 electroporations as described above.

Sequence Diversity of the Library

To assess the sequence diversity of the library, 190 clones were randomly selected from the library and sequenced. 166 complete sequences were obtained, of which 143 have correct reading frames. The 143 sequences were aligned, and the occurrence of A/D/S/Y in each mutated position within CDR1s, the origins of CDR2s and their mutations, and the length distribution of CDR3s were tabulated. The results showed that these sequences were totally different from each other after recombination among three CDRs although several identical CDR1s and CDR2s were found due to the limited diversity or conservation themselves.

Figure 8:
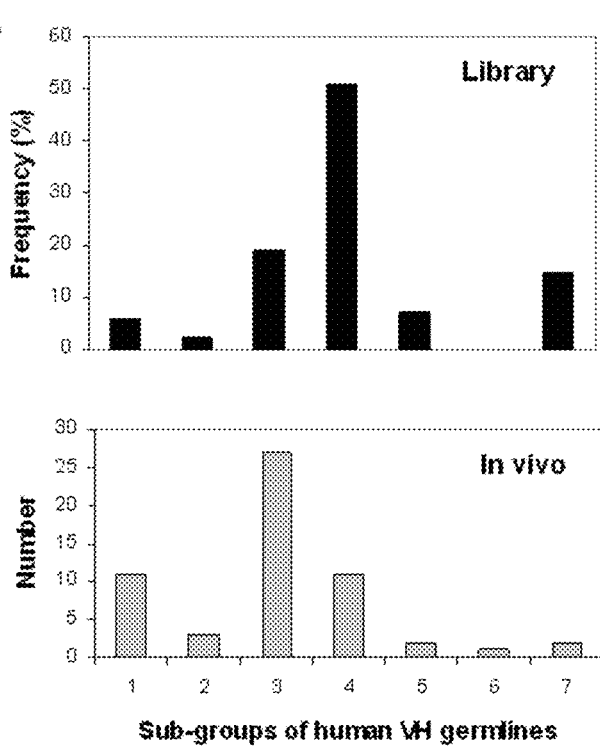
FIG. 8 illustrates the sequence diversity analysis of the VH domain library of the invention, and as described in Example 2. To evaluate the sequence diversity of the library, clones were randomly selected and sequenced. Regarding the diversity of CDR1 sequences.
Figure 9:
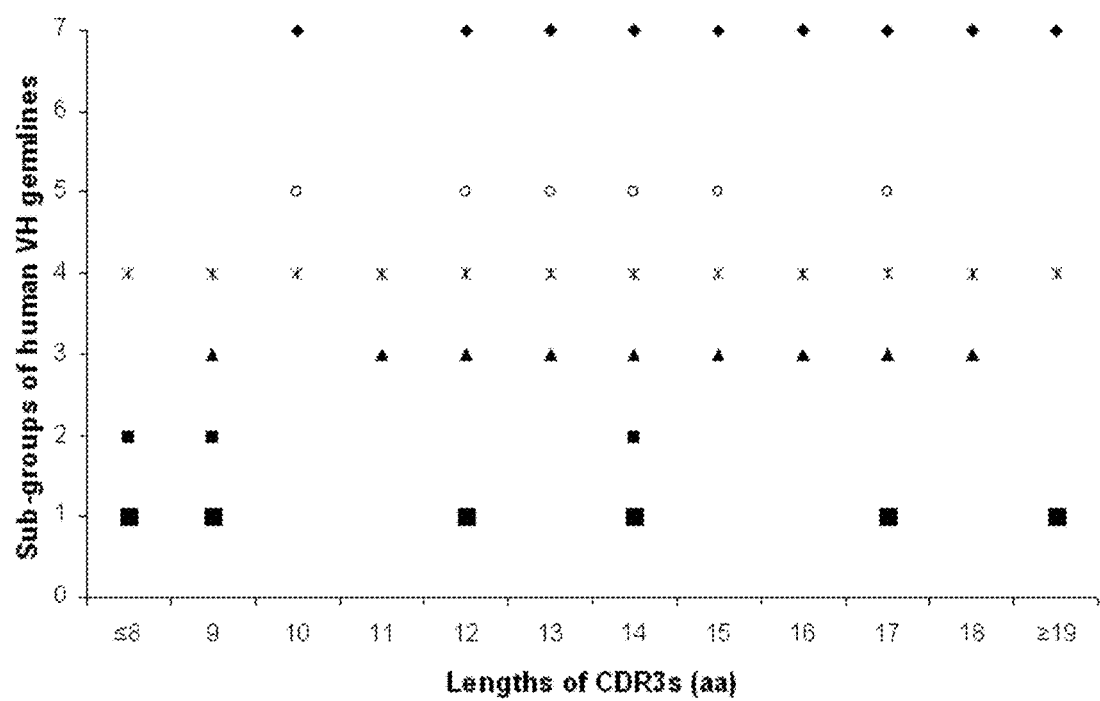
FIG. 9 shows the diversity in the lengths of the CDR3s of the different human VH germlines genes.

For CDR1s, A/D/S/Y was well scattered in each position while Y dominated slightly (see FIG. 8A). CDR2s were derived from VH1, 2, 3, 4, 5 and 7 of germlines (see FIG. 8B). VH4-derived CDR2s were dominant by covering around 50% of the 143 sequences. No CDR2s originated from VH6, which is the smallest one, were found. More than 40% of CDR2s are completely identical to the germline sequences, while there are members with many mutations, regardless of those induced by PCR process (see FIG. 8C). For the CDR3s, the lengths vary from 5 to 24 amino acid residues with a central peak from 12 to 14 residues and a side peak at 17 residues (see FIG. 8D). In comparison with the length distribution of CDR3s in vivo (Wu et al., Proteins, 1993), there is relatively limited number of CDR3s with length shorter than 8 or longer than 19 residues. Moreover, CDR2s from different origins were paired with CDR3s with varying length (see FIG. 9). These data suggest that the library should have high sequence diversity.

Folding of Phage-Displayed VHs

The folding of phage-displayed VHs was evaluated by measuring their activity binding to protein A since a VH3 framework scaffold m0 was used in library construction. The library was cycled through 4 rounds of selection to enrich for members that were capable of binding to protein A, and thus, were likely to be folded as natural VH3 structures. 95 clones were randomly picked from the fourth round of enrichment and sequenced and 79 complete and clear sequences were obtained. In the 143 clones from the original library, all 4 positions mutated in CDR1s bias slightly toward residue Y (see FIG. 8A) and VH3-originated CDR2s cover about 20% (see FIG. 8B). In contrast, all 79 sequences picked after the binding selection process against protein A were shown to have CDR2s derived from VH3. Within CDR1, residue D apparently dominates in position #27, 29 and 32 (see FIG. 10). CDR3 of these clones are much diversified and the length varies from 7 to 17 residues.

VH Expression and Solubility

We evaluated the expression and solubility of VHs by measuring the yield of soluble proteins purified from the soluble fraction of E. coli periplasm. First, 2 clones each, one with relatively short CDR3 and the other long CDR3, were selected from those with CDR2s derived from 6 different groups of human VH germlines, respectively, expressed and purified as described above. The SDS-PAGE result showed that 11 of 12 could be expressed in the form of soluble proteins and the estimated yield ranged from 0.5 to 24 mg 17 (see FIG. 11A). There was no significant relation between the yield and the CDR2 origins or CDR3 lengths of VHs tested.

Then, 12 clones (named c3, c6, d1, d7, b4, c11, d10, b3, b5 (also referred to hereas m36), b7, g6 and e11) with CDR3 length from 7 to 24 residues were picked from those with VH4-derived CDR2s and measured for soluble protein expression. 10 of 12 clones gave yield varying from 0.5 to 15 mg $l^{-1}$ and there was no obvious connection between the yield and the lengths of CDR3 either (see FIG. 11B). Last, we evaluated the solubility of VHs selected after three and four rounds of biopanning of the library with HIV-1 antigen gp120-CD4 fusion protein and gp140 (described further below).

Figure 7:
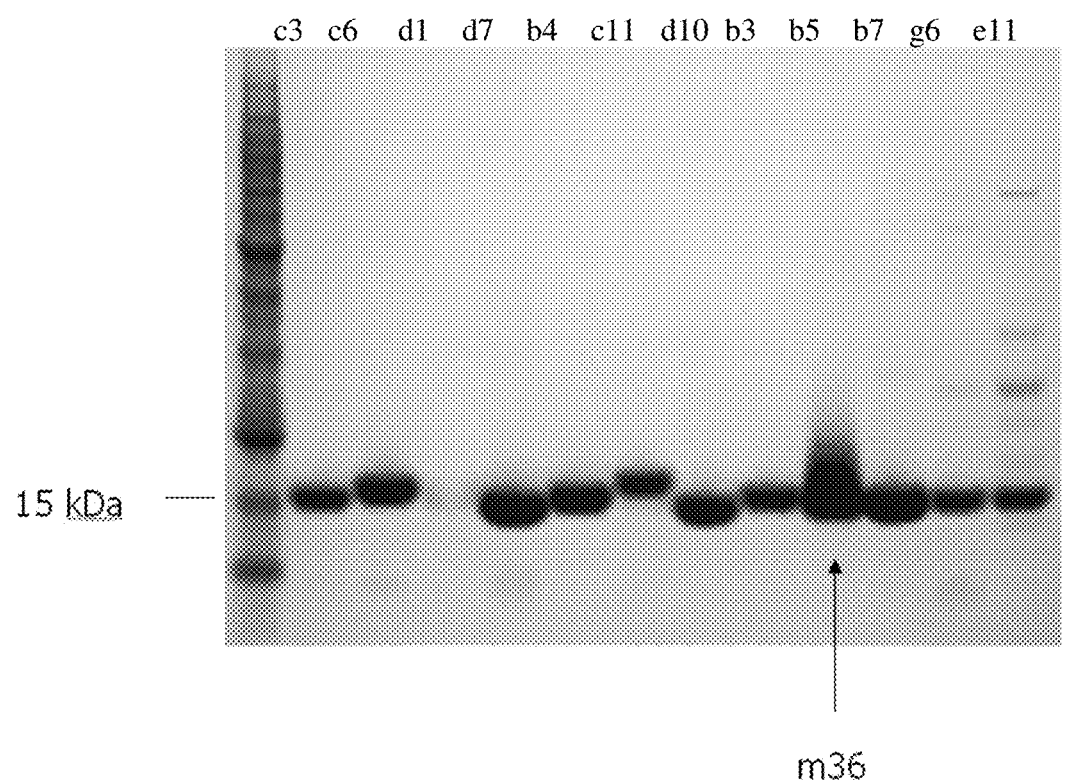
FIG. 7 is a photograph of an SDS-PAGE gel showing soluble VHs selected against HIV-1 antigens. Twelve positive clones (c3, c6, d1, d7, b4, c11, d10, b3, b5 (m36), b7, g6 and e11) were selected after three rounds of sequential panning of library with HIV-1 antigens gp120-CD4 and gp140, expressed and purified by immobilized metal ion affinity chromatography (IMAC) using Ni-NTA resin.
Figure 11:
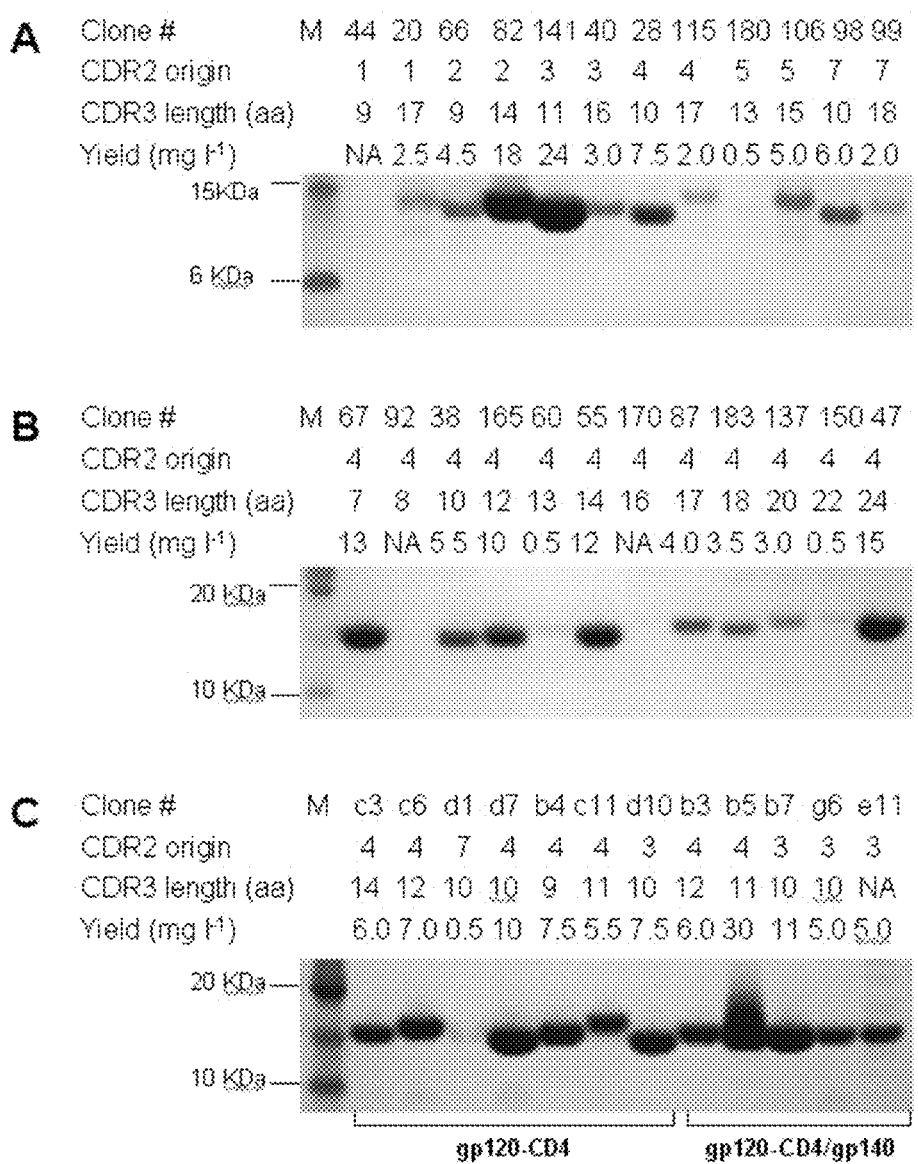
FIG. 11 shows SDS-PAGE gels of three sets of clones grouped in A, B and C gels. For each gel, the clone number, the origin of the CDR2, the length in amino acids of CDR3, and the yield in milligrams are indicated for each set of clones. See Example 2 for further description. The figure shows the expression profile before (11A and B) and after (11C) panning with antigens.

Twelve positive clones on monoclonal phage ELISA with A405 of >1.5 were expressed and purified. As shown in FIG. 11C (which is a duplicate of the gel image of FIG. 7 showing the identify of clone b5 or "m36"), 11 of 12 clones gave high-level yield from 5.0 to 30 mg $l^{-1}$. These clones have CDR2s that originated from VH3, VH4 and VH7, which were determined to be dominant in the library (see FIG. 8B). These clones were also shown to have medium length CDR3s.

These results indicate that the framework scaffold used for library construction could be flexible enough to harbor CDR2s derived from a variety of human VH germlines and CDR3s with length as short as 7 residues and as long as 24 residues.

Selection of VHs Against Viral and Cancer-Related Antigens

To assay the performance of the library and given the constant need for new and better therapeutics, the library was panned against three viral antigens and one cancer-related antigen (see Table 3).

TABLE 3

Panning of the library with viral and cancer-related antigens.

| Antigen | No. of selections | Positive clones/ tested clones | No. of unique clones/ sequenced clones | EC$_{50}$ of the best binder (µg/ml) |
|---|---|---|---|---|
| gp120-CD4 (HIV-1 antigen) | 4 | 188/190 | 14/14 | ND |
| gp120-CD4/ gp140 (HIV-1 antigen) | 4 | 17/190 | 7/7 | 0.040[a] |
| B5R (vaccinia antigen) | 3 | 6/95 | 6/6 | 0.013 |
| Her2 (cancer antigen) | 3 | 5/95 | 5/5 | 1.1 |

[a]Binding activity with gp120-CD4.

Selections were carried out using antigens conjugated on magnetic beads as described above. In the sequential panning with HIV-1 antigens (alternate panning between HIV gp120-CD4 and gp140), gp120-CD4 was used for the first round and third round, and gp140 the second round and fourth round. Enrichment was achieved in all selections and positive clones were identified on monoclonal phage ELISA.

A handful of clones having a high value of A405 following the ELISA were sequenced. All of the sequenced clones were mosaic, especially in CDR1 and CDR3 (see Table 4).

TABLE 4

CDR diversity of phage-displayed VHs selected from biopanning.

| Antigen | Round No. | Clone | CDR1 | CDR2 Sequence | CDR2 Origin | CDR3 |
|---|---|---|---|---|---|---|
| gp120-CD4 | 3 | a9 | D-H-HS-- | INHSGIT (SEQ ID NO: 23) | 4-4, 4-34 | AIVDTAMVWDY (SEQ ID NO: 44) |
| | | b2 | S-A-SD-- | INHSGST (SEQ ID NO: 24) | 4-4, 4-34 | AASGSYSDY (SEQ ID NO: 45) |
| | | b3 | A-D-SY-- | INHSGST (SEQ ID NO: 24) | 4-4, 4-34 | ATHDYGDSFES (SEQ ID NO: 46) |
| | | c3 | D-S-YS-- | INHSGST (SEQ ID NO: 24) | 4-4, 4-34 | ARIGDGFFSD AFEI (SEQ ID NO: 47) |
| | | c6 | D-Y-DY-- | IDNSGST (SEQ ID NO: 25) | 4-28, 4-30-2, ect. | AGDYGSGSEFEN (SEQ ID NO: 48) |
| | | d1 | D-D-YD-- | INTDGDIP (SEQ ID NO: 26) | 7-4-1 | AKYTWNSDS GWGEL (SEQ ID NO: 49) |
| | | d7 | Y-D-YD-- | IYHRGNT (SEQ ID NO: 27) | 4-4, 4-30-2, ect. | VGYGADQDDC (SEQ ID NO: 50) |
| | | e10 | D-A-DD-- | INHTGST (SEQ ID NO: 28) | 4-34 | ATHDYGDSFES (SEQ ID NO: 51) |
| | | g2 | D-D-DY-- | INHSGST (SEQ ID NO: 24) | 4-4, 4-34 | AADTGNAFDI (SEQ ID NO: 52) |
| | 4 | a11 | Y-D-DD-- | INHSGST (SEQ ID NO: 24) | 4-4, 4-34 | AGSSGWLHE Y (SEQ ID NO: 53) |
| | | b4 | D-D-AS-- | INHSGST (SEQ ID NO: 24) | 4-4, 4-34 | ATDQAGIEH (SEQ ID NO: 54) |
| | | c8 | S-S-AD-- | INHSGST (SEQ ID NO: 24) | 4-4, 4-34 | ATSVGYEEL (SEQ ID NO: 55) |
| | | c11 | A-S-DY-- | INHSGST (SEQ ID NO: 24) | 4-4, 4-34 | AMSDGYSAT DV (SEQ ID NO: 56) |
| | | d10 | A-A-DD-- | ITGSGDTT (SEQ ID NO: 29) | 3-23 | ALTDSSSYDY (SEQ ID NO: 57) |

TABLE 4-continued

CDR diversity of phage-displayed VHs selected from biopanning.

| Antigen | Round No. | Clone | CDR1 | CDR2 Sequence | Origin | CDR3 |
|---|---|---|---|---|---|---|
| gp120-CD4/ gp140 | 3 | a8 | D-D-SD-- | INHSGST (SEQ ID NO: 24) | 4-4, 4-34 | AFYMRGAILEY (SEQ ID NO: 58) |
| | | b3 | Y-D-SS-- | INHSGST (SEQ ID NO: 24) | 4-4, 4-34 | AAYDFWSGSYPEY (SEQ ID NO: 59) |
| | | b5 | A-D-SD-- | INDSGNT (SEQ ID NO: 30) | 4-34, 4-55 | AIYGGNSGGEY (SEQ ID NO: 60) |
| | | b7 | D-S-DY-- | VGGSGERT (SEQ ID NO: 31) | 3-23 | ARIDRDGDEH (SEQ ID NO: 61) |
| | | c6 | S-D-DY-- | INHSGST (SEQ ID NO: 24) | 4-4, 4-34 | AGSGSYSDY (SEQ ID NO: 62) |
| | 4 | g6 | D-A-DY-- | INSNGSVT (SEQ ID NO: 32) | 3-74 | ARDWGYSPED (SEQ ID NO: 63) |
| | | e11 | Y-D-YD-- | ISYDGSIK (SEQ ID NO: 33) | 3-30, 3-30-3 | N/A |
| B5R | 3 | z1 | S-Y-DY-- | IYHSGST (SEQ ID NO: 34) | 4-30-2 | ARTPPRIAAAGMRYFDL (SEQ ID NO: 64) |
| | | z2 | S-D-AD-- | INSSSSYI (SEQ ID NO: 35) | 3-21 | ARDWGYSPED (SEQ ID NO: 65) |
| | | z3 | D-D-YS-- | ISGDGGAT (SEQ ID NO: 36) | 3-23 | ARADYRSTDH (SEQ ID NO: 66) |
| | | z4 | D-S-YD-- | IYYSGST (SEQ ID NO: 37) | 4-39 | ARQVAAPV (SEQ ID NO: 67) |
| | | z5 | D-S-YY-- | IKQDGSVV (SEQ ID NO: 38) | 3-7 | ARDWGYSPED (SEQ ID NO: 68) |
| | | z6 | Y-D-YA-- | ISYDGSNK (SEQ ID NO: 39) | 3-30, 3-30-3 | VRDWGYNPED (SEQ ID NO: 69) |
| Her2 | 3 | z7 | Y-D-SS-- | IYSGGTT (SEQ ID NO: 40) | 3-53, 3-66 | VRDWGYNPED (SEQ ID NO: 70) |
| | | z8 | Y-Y-DY-- | ISNSGGTI (SEQ ID NO: 41) | 3-11 | ARGTGLHDYGDYWAHTEFDY (SEQ ID NO: 71) |
| | | z9 | D-A-AD-- | IYSGGST (SEQ ID NO: 42) | 3-53, 3-66 | ARDWGYSPED (SEQ ID NO: 72) |
| | | z10 | D-D-YD-- | IRYDGSNK (SEQ ID NO: 43) | 3-30, 3-30-3, ect. | ARGVDYGDYGGYFDY (SEQ ID NO: 73) |

For the panning against HIV-1 antigens, however, most of selected clones have CDR2s originated from VH4, in particular VH4-4 or VH4-34 sub-group. Their CDR3s vary and lengths range from 9 to 14 residues. In contrast, most and all clones selected from B5R and Her2 panning, respectively, have VH3-derived CDR2s. Some of them, for example, z2, z5 and z6, have similar CDR3s.

Some clones were expressed and purified, and their binding and specificity were confirmed by ELISA against the antigen used for its selection, as well as several unrelated antigens (e.g. BSA or antigens which are significantly heterologous to the one used in the panning could be used as unrelated antigens. For example, in the Her2 panning HIV-1 antigen Bal gp120-CD4 could used as a negative control while in the Bal gp120-CD4 panning Her2 could be used as an unrelated antigen).

In the sequential panning, an antibody with affinity in nanomolar range ($EC_{50}$=0.040 μg/ml), designated b5 (see FIG. 11C) (later designated m36) was identified as binding to HIV-1 antigen gp120-CD4 but neither gp120 nor CD4 alone.

Further characterization showed that b5 (m36) was a potent neutralizing antibody which targeted an epitope on HIV-1 gp120 whose accessibility appeared to be induced upon CD4 binding to HIV-1 gp120. In addition, b5 (m36) was determined to be cross-reactive against HIV-1 isolates from clade A, B, C, and D (see FIG. 17).

Regarding panning results for vaccinia antigen B5R, a specific VH, z1, was found with an $EC_{50}$ of 0.013 μg/ml. Binders against human self-antigen Her2 could also be selected, albeit at a somewhat lower frequency and with lower affinity (see Table 3).

VH Oligomerization

Size exclusion chromatography was performed to measure the oligomerization of VHs using superdex75 column. 5 purified VHs were randomly selected from 12 positive clones (c3, c6, d1, d7, b4, c11, d10, b3, b5, b7, g6 and e11) against HIV-1 antigen gp120 on monoclonal phage ELISA and tested for oligomerization. 2 of 5 VHs, e.g. b7 and d10, have CDR2s originated from human VH3 while the CDR2s of the other 3 from human VH4 (see FIG. 11C).

Before conducting the experiments, all 12 VHs (c3, c6, d1, d7, b4, c11, d10, b3, b5, b7, g6 and e11) had already been stored at 4° C. for 4 weeks and no precipitation was observed with these protein solutions. The data shown in FIG. 12 demonstrates the existence of a monomeric state of all 5 VHs (~15 kDa) and lack of higher order oligomers.

Discussion Fo Example 2 Results:

Domain antibodies (dAbs) are of great interest for biomedical application due to their special biophysical properties. However, the poor solubility and stability of most dAbs, particularly those derived from human antibodies, severely limits the successful development of dAbs and dAb libraries. Camels produce functional antibodies devoid of light chains, $V_H$Hs, which are adapted replacing aliphatic residues in the former light chain interface by hydrophobic residues, packing against the framework and stabilizing the global $V_H$H fold by long CDR3s (Holt et al., Trends Biotech., 2003; Muyldermans et al., Trends in Biochem. Sciences, 2001). It has been demonstrated that the variable domains of human VH3 are significantly more soluble and stable than those from any other human VH and VL families in the absence of light chains (Holt et al., Trends Biotech., 2003).

Jirholt et al. used a camelized human VH3 germline, DP47, as a master framework for construction of a dAb library of $9\times10^6$ members but no further characterization was described in terms of solubility and functionality of dAbs from the library (Jirholt et al., Gene, 1998).

The present inventors have constructed a large non-immune human Fab library (~$1.5\times10^{10}$ members) from the lymph nodes, spleen and peripheral blood lymphocytes of 50 donors. One of these Fabs (R3H1, see FIG. 4) had a stop codon in the light chain but was still isolated from library panning and was functional as a heavy chain alone. The VH domain of this antibody was cloned to form the VH domain antibody, m0 (as shown in FIGS. 5A and 5B). It was found that m0 exhibits high levels of expression and high solubility.

m0, a natural VH domain and belonging to the VH3 family, was used as a framework to construct a large human VH domain library (~$2.5\times10^{10}$ members) by grafting in vivo-formed CDR2s and CDR3s from our other human antibody libraries and mutating four residues in CDR1. The library exhibited a high degree of variability and most of VHs were highly soluble. The quality of the library was also validated by selection of VHs against a panel of antigens, including HIV-1 antigens (Bal gp120-CD4; Bal gp120-CD4/R2 gp140), a vaccinia antigen (B5R), and a cancer antigen (Her2).

Without wishing to be bound by theory, naturally occurring and proofread CDRs are advantageous as compared to synthetic repertoire CDRs because they are processed and adapted by the immune system with respect to their functionality and immunogenicity. Abergel and Claverie (Eur. J. Immunol., 1991) showed that VH genes rearranged in vivo have CDR3s largely derived from the D-segments encoding amino acids with a propensity for loop formation. By comparison with synthetic CDR3s, therefore, naturally occurring CDRs may be more likely to fold properly or produce usefully shaped binding sites. Furthermore, there is evidence that antibodies derived from recombination of natural CDRs exhibit low immunogenicity (Soderlind et al., Nature Biotech., 2000). A scFv library containing $2\times10^9$ members has recently been constructed by randomly shuffling all six in-vivo formed CDRs into a single master framework using human VH DP47 and VL DPL3. Ten scFvs selected from the library specific for different antigens did not show an increased presence of T-cell epitopes, and they contained even fewer T-cell epitopes than the natural antibody variable regions.

The size and sequence diversity are thought to be key features of high-quality libraries. A finding consistent with theoretical considerations is that the affinity of antibodies selected is proportional to the size of the library, with $K_d$s ranging from $10^{6-7}$ for the smaller libraries to $10^9$ for the larger ones, and antibodies with affinity comparable to those obtained from immune libraries can be selected from naïve libraries that are large enough (Andrew et al., J. Immunol. Methods, 2004).

Aiming in part at generating a library with enormous diversity, the present invention relates to the design of a new set of primers to allow amplification of as many VH genes as possible. The complexity of the library formed according to the invention was determined by sequencing 190 clones randomly selected (see FIG. 8 and FIG. 9). The 143 complete sequences have CDR2s derived from 6 (VH1-5 and 7) of 7 human VH germlines (see FIG. 8B). Since VH6 is the smallest group of germlines, we assume that CDR2s with VH6 origin could also be found if more clones are sequenced. The length, sequence, and pairing of CDR3s with different germline-derived CDR2s were varied simultaneously (see FIGS. 8D and 9). These data suggest that this library should have high sequence diversity.

In a scFv library previously constructed, primers were designed for amplification of naturally occurring CDRs, but they were specific for DP47 and DPL3 frameworks only (Soderlind et al., Nature Biotech., 2000; Jirholt et al., Gene, 1998). By contrast, the primers used in the present invention advantageously may cover CDRs derived from all groups of human VH germlines, as described above. They may, therefore, the present invention, in part, facilitates more rapid and efficient construction of large human VH domain libraries.

While the combinatorial strategy provides a powerful tool for creating tremendous diversity, the m0 framework scaffold used in the library construction plays a challenging role because it must support the CDRs from various non-VH3 germlines while maintain a stable tertiary fold. Structural incompatibility between these foreign CDRs and the fixed framework could potentially prevent the formation of stable and soluble VHs. Thus, it is surprising and unexpected that the domain antibodies of the invention specific against various antigens and having a diversity of non-VH3 CDRs possess good folding characteristics.

Protein A binding is considered a marker for proper folding of human VH3 (Potter et al., J. Immunol., 1996). To see whether recombinant VHs with a fixed m0 which is close to VH3 scaffold could retain activity, the library was cycled through four rounds of selection against protein A. All 79 clones randomly picked from the fourth round of selection had CDR2s derived from VH3, suggesting that VH3-derived CDR2s and their flanking FR regions are essential for their property of protein A binding, in agreement with previous studies (Potter et al., J. Immunol., 1996; Randen et al., Eur. J. Immunol., 1993). Interestingly, position #27 and 29 in CDR1s significantly biases toward residue D in those clones after protein A selection while residue Y dominates in these positions of VHs with VH3-derived CDR2s before selection (see FIG. 10). There is also a slight increase in the usage of D in position #32 and this does not happen to position #31. Given D is a small and polar residue, and Y an aromatic residue, the polarity of the residues in these positions could significantly impact the folding of VH3 with respect to protein A binding activity.

It has recently been demonstrated that this property can be used to monitor the structural stability and soluble expression of VH3 (Bond et al., J. Mol. Biol., 2003). Thus, the fact that VHs with non-VH3 CDR2s lack the property further raises a doubt whether these VHs can be soluble and stable. To address this issue, the yield of soluble VHs having non-VH3 CDR2s and CDR3s ranging from 7 to 24 residues was measured (FIG. 11). The results show that most of VHs have favorable yield of soluble proteins and the yield is not significantly related to CDR2 origin and CDR3 length.

Figure 12:
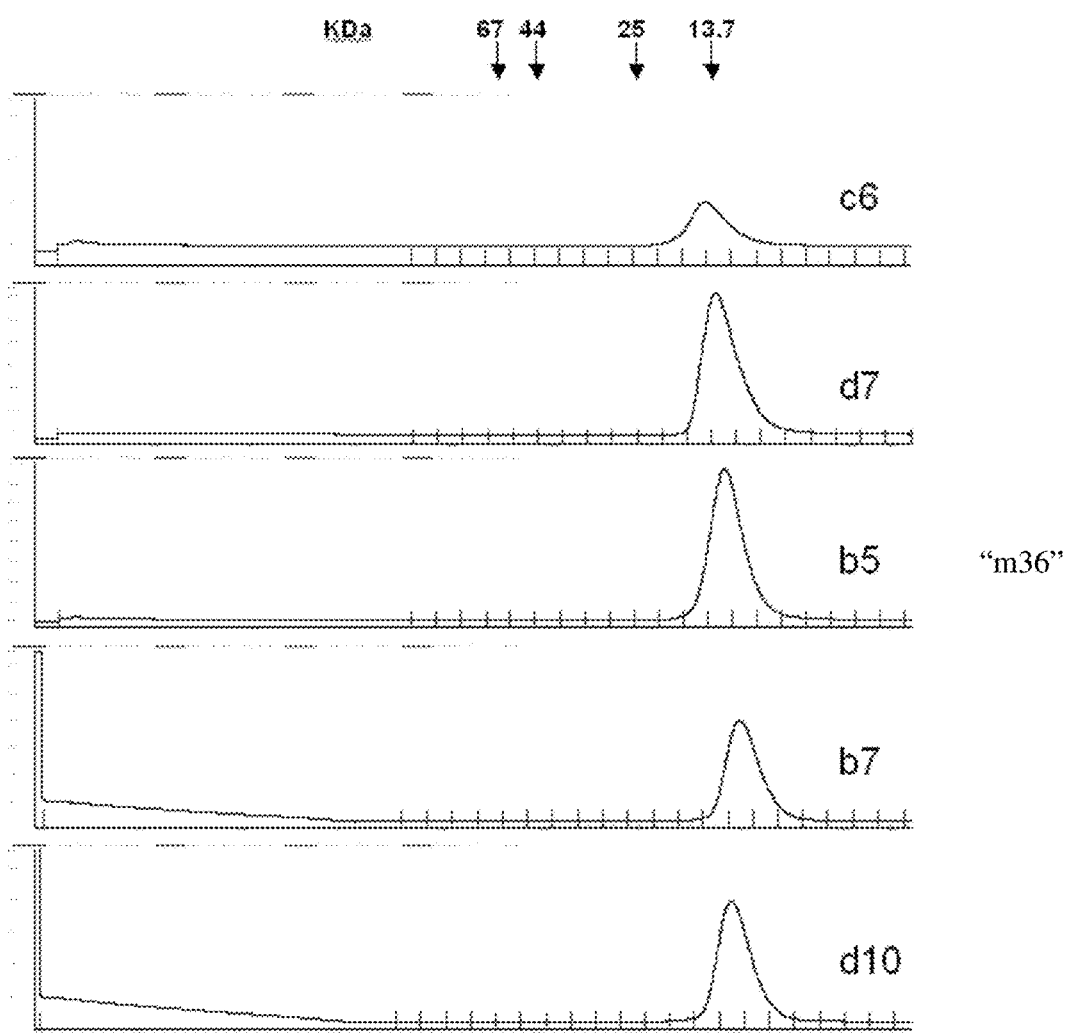
FIG. 12 shows the results of size exclusion chromatography analysis to measure the oligomerization of select isolated VHs, c6, d7, b5 (m36), b7 and d10. See Example 2 for further description.
Figure 13:
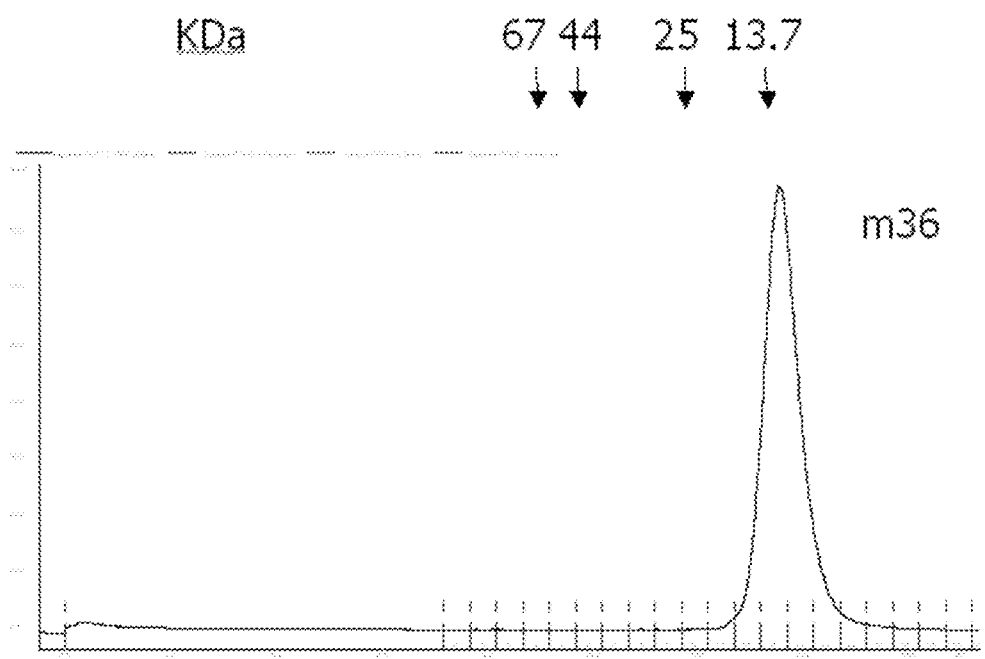
FIG. 13 shows the results of size exclusion chromatography analysis to measure the oligomerization of m36. Purified m36 in PBS was subjected to size exclusion chromatography with Superdex75 column calibrated with protein molecular mass standard shown by the arrows.
Figure 14:
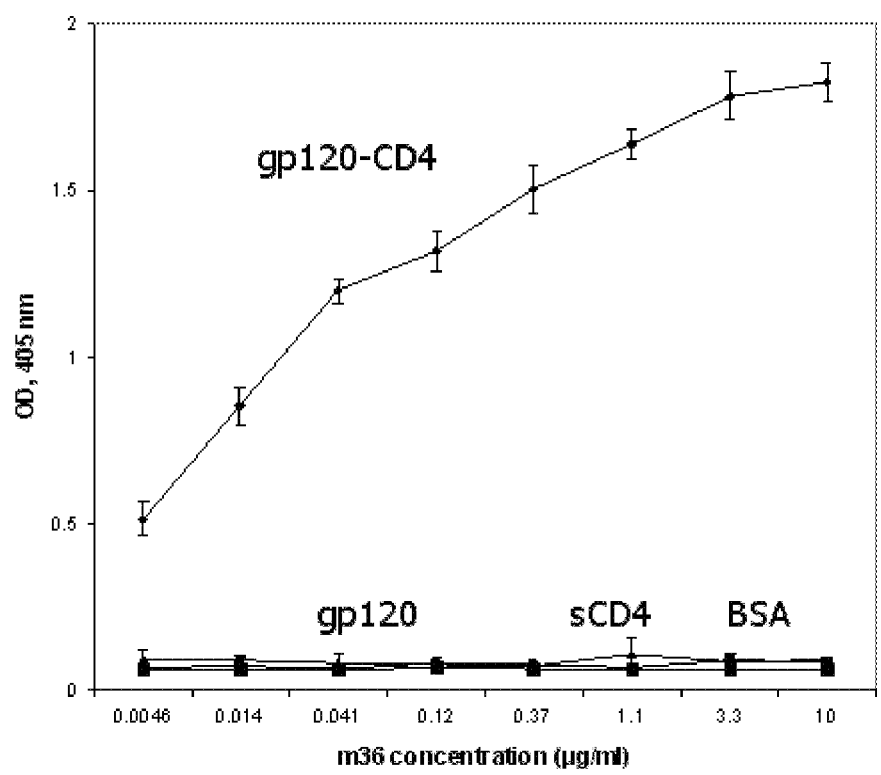
FIG. 14 shows the binding specificity of m36. Binding of m36 was tested by ELISA using Corning high-binding 96-well plates coated with 1 µg/ml of antigens. Bound m36 were detected by adding 1:5000 diluted HRP-conjugated anti-FLAG antibody. The assay was developed at 37° C. with ABST substrate and monitored at 405 nm as described.
Figure 15:
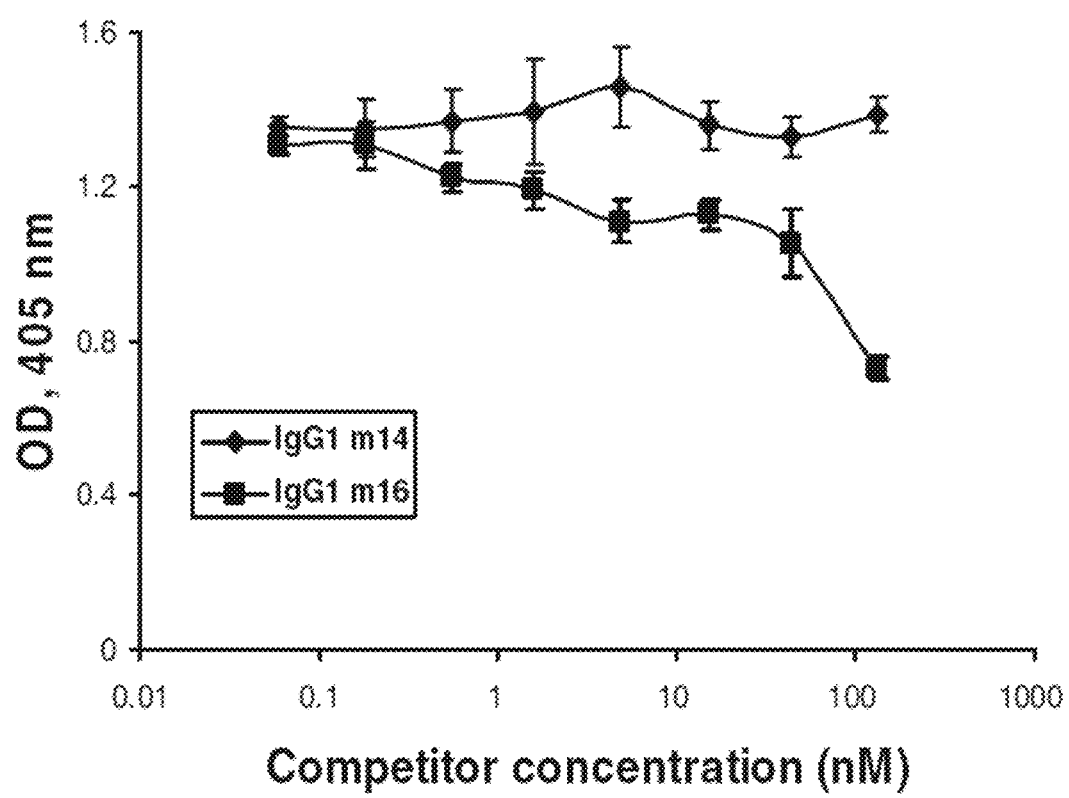
FIG. 15 shows that the binding of m36 to gp120 is induced by the gp120 interaction with CD4. $gp120_{Bal}$-CD4 was coated on Corning high-binding 96-well plates. M36 with consensus concentration was mixed with either a known CD4i antibody (m16) or CD4bs antibody (m14) (negative control) in IgG format serially diluted, and added to 96-well plates coated with antigen. Bound m36 were detected by 1:5000 diluted HRP-conjugated anti-FLAG antibody. The assay was developed at 37° C. with ABST substrate and monitored at 405 nm. See FIG. 27 for complementary data showing the specific binding of m36 to $gp120_{Bal}$-CD4 but not to $gp120_{Bal}$ alone.
Figure 16:
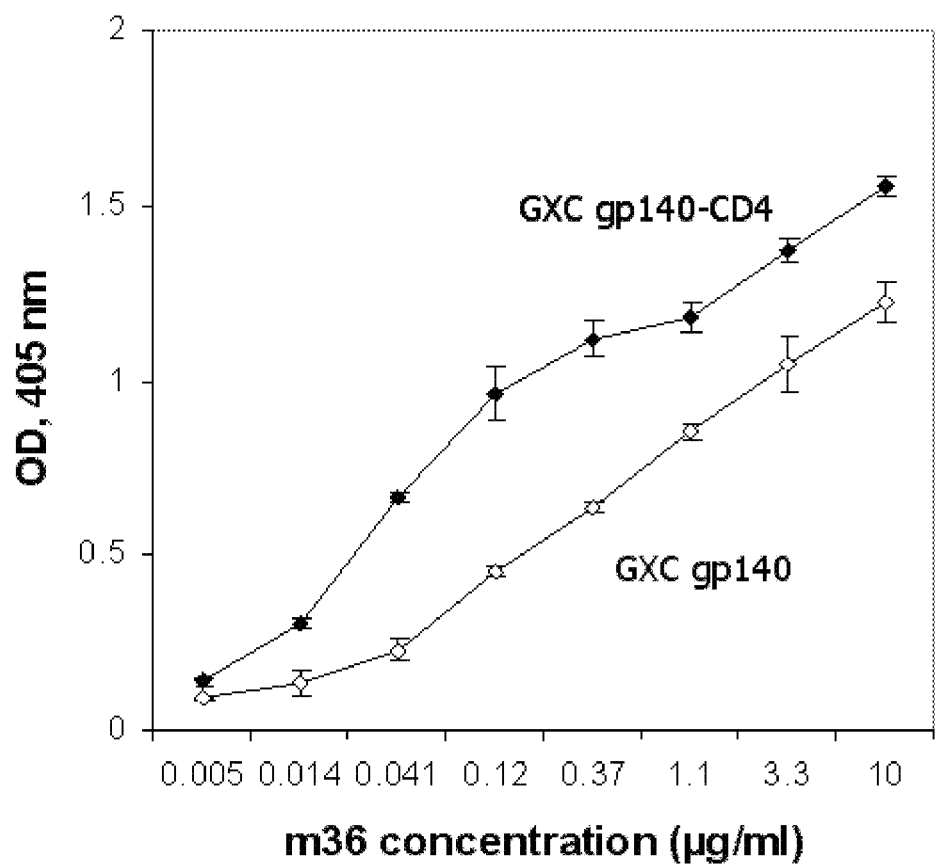
FIG. 16 shows the cross-reactivity of m36. GXC gp140 from an isolate of clade C was coated in the presence or absence of CD4. Serially diluted m36 was added and detected by HRP-conjugated anti-FLAG antibody. The assay was developed at 37° C. with ABST substrate and monitored at 405 nm.

In addition to proper folding, the domain antibodies of the invention were evaluated as to whether they possessed any tendency to form dimers and higher order multimers—which, for steric considerations, may not be desirable. Antibodies in the format of scFv have the tendency to form dimers and higher order multimers in a clone-dependent and relatively unpredictable way (Abergel et al. 1991; Andrew et al., 2004; Potter et al., 1996). The oligomerization of 5 VHs randomly selected was measured by size exclusion chromatography and they all appeared to be monomeric (see FIG. 12). There is evidence that VHs are prone to aggregate upon concentration or prolonged standing at 4° C. (Kortt et all, 1995; Ewert et al., 2002). The 5 VHs tested for oligomerization were concentrated to get concentrations of as high as 10 mg/ml. After being stored at 4° C. for more than 8 weeks no precipitation was observed with these 5 protein solutions.

These data suggest that the m0 scaffold not only is capable of presenting diverse CDRs, but also has desirable properties for biotechnological application, including, high level of expression, solubility, resistance to aggregation in solution, and lack of polymerization.

A central question in the evaluation of the library is whether high-affinity functional VHs could be directly selected against a panel of antigens. The library design was based on the principle that a specific single framework had the potential to include CDRs derived from other groups of germline genes and the small antigen-binding surface was capable of presenting structural diversity enough to form paratopes for a wide range of antigens.

Biopanning of the library showed that VHs with estimated affinity in nanomolar range could be obtained against viral antigens (see Table 3). Binders against human self-antigens could also be selected, albeit at a somewhat lower frequency and with lower affinity. These binders are much diversified in CDRs (see Table 4) suggesting that a number of different antibody specificities could be generated. Thus, this Example demonstrates that this library could be useful for selection of high-affinity binders as therapeutics, e.g., HIV therapeutics.

Example 3. Human Domain Antibodies to Conserved Sterically Restricted Regions on Gp120 as Exceptionally Potent Cross-Reactive HIV-1 Neutralizers This Examples describes the identification and characterization of an antibody heavy chain variable domain (VH) (domain antibody, dAb), m36, targeting highly conserved but sterically restricted CD4-induced (CD4i) structures on the Env. It is believed that M36 is the first reported representative of a novel class of potent and broadly cross-reactive HIV-1 inhibitors based on human dAbs. It has potential as a candidate therapeutic and a microbicide, and as an agent for exploration of the highly protected conserved Env structures with implications for the design of novel small molecule inhibitors, and elucidation of the mechanisms of virus entry into cells and evasion of immune responses.

The following methods and materials were employed in this Example. The results of this Example are subsequently discussed below.

Methods and Materials:

Cells, Viruses, Plasmids, Gp120, Gp140 and Antibodies 293T cells were purchased from ATCC. Other cell lines and plasmids used for expression of various HIV-1 Envs were obtained from the NIH AIDS Research and Reference Reagent Program (ARRRP). Recombinant gp140s were kindly provided by C. Broder (USUHS, Bethesda, Md.). Gp120$_{Bal}$ and the single-chain fusion protein gp120$_{Bal}$-CD4 (8) were gifts from T. Fouts (Institute of Human Virology, Baltimore; currently at Profectus, Baltimore, Md.). Horseradish peroxidase (HRP)-conjugated anti-FLAG tag antibody and HRP-conjugated anti-human IgG (Fc-specific) antibody were purchased (Sigma-Aldrich, St. Louis, Mo.).

Library Construction and Selection of VHs Against HIV-1 Antigens

Figure 23:
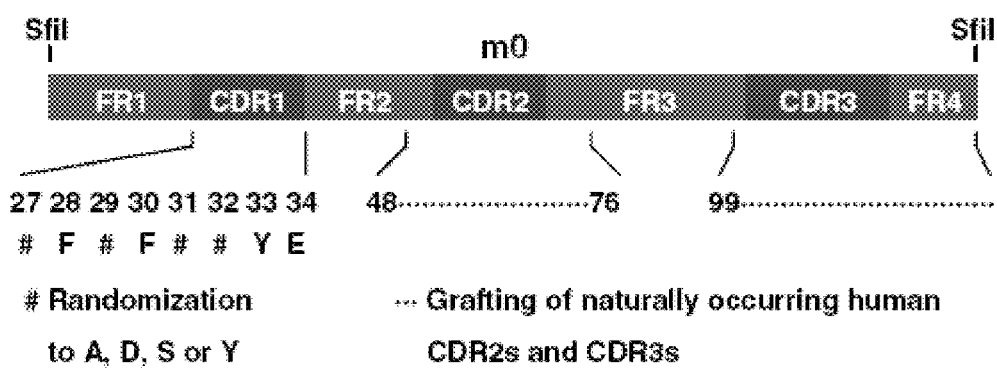
FIG. 23 depicts the construction of a human antibody VH library. A stable VH (m0) was used as a scaffold for grafting CDR2s and CDR3s from five human antibody Fab libraries. CDR1 residues #27, 29, 31 and 32 (IMGT numbering system) were randomized to A, D, S or Y. The numbers denote the positions of the amino acid residues corresponding to the respective regions of the antibody VH gene where the CDRs were grafted; the # denotes the positions of the CDR1 randomization. The SfiI denotes the restriction enzyme sites used for cloning.

A large phage-displayed human VH library (~$2.5 \times 10^{10}$ individuals) was constructed by grafting of naturally occurring heavy chain CDR2s and CDR3s from other five template libraries to a VH framework scaffold, m0, and randomly mutating four putative solvent-accessible residues in its CDR1 (FIG. 23). These template libraries include: (a) a naive human Fab library ($5 \times 10^9$ members) from peripheral blood B cells of 10 healthy donors (Zhu et al., 2006); (b) a naïve human Fab library ($1.5 \times 10^{10}$ members) from peripheral blood B cells of 22 healthy donors, spleens of three donors, and lymph nodes of healthy 34 donors; (c) two naïve human Fab libraries ($6 \times 10^8$ and $7.2 \times 10^8$ members, respectively) from cord blood of two healthy babies, respectively; and (d) an immune human Fab library from the bone marrow of three long-term nonprogressors whose sera exhibited the broadest and most potent HIV-1 neutralization among 37 HIV-infected individuals (Chen et al., J. Mol. Biol., (2008) 382:779-789, which is incorporated herein by reference in its entirety). This dAb library was used for selection of VHs against HIV-1 antigens conjugated to magnetic beads (Dynabeads M-270 epoxy; DYNAL Inc., New Hyde Park, N.Y.) as described previously (Zhu et al, 2006). For sequential panning, 10 and 5 μg of gp120$_{Bal}$-CD4 was used in the first round and third round, respectively; antigens were alternated with 5 μg of gp140$_{R2}$ or gp140$_{JRFL}$ during the second round and fourth round. Clones that bound to HIV-1 antigens were identified from the third and fourth round of biopanning by using monoclonal phage ELISA as described (Zhu et al, 2006).

Construction and Cloning of m36 Fusion Proteins

The following primers were used:

m36F,
(SEQ ID NO: 74)
5'-TGGTTTCGCTACCGTGGCCCAGCCGGCCCAGGTGCAGCTGGTG-3'
(sense);

m36F1,
(SEQ ID NO: 75)
5'-TGGTTTCGCTACCGTGGCCCAGGCGGCCCAGGTGCAGCTGGTG-3' (sense);

m36R1,
(SEQ ID NO: 76)
5'-GTGAGTTTTGTCGGGCCCTGAGGAGACGGTGAC-3' (antisense);

m36R2,
(SEQ ID NO: 77)
5'-TGGTTGTGGTTGGGGTATCTTGGGTTCTGAGGAGACGGTGAC-3' (antisense);

m36R3,
(SEQ ID NO: 78)
5'-GTCACCAAGTGGGGTTTTGAGCTCTGAGGAGACGGTGAC-3' (antisense);

m36R4,
(SEQ ID NO: 79)
5'-TTCTCGGGGCTGCCCTGAGGAGACGGTGAC-3' (antisense);

m36R5,
(SEQ ID NO: 80)
5'-CAGGAGTTCAGGTGCTGAGGAGACGGTGAC-3' (antisense);

CH3F,
(SEQ ID NO: 81)
5'-GGGCAGCCCCGAGAACCA-3' (sense);

CH3R,
(SEQ ID NO: 82)
5'-GTGGTGGTGGTGGTGGCCGGCCTGGCCTTTACCCGGAGACAG-3' (antisense);

FcF1,
(SEQ ID NO: 83)
5'-ACGTGTCCCAAATGTCCAGCACCTGAACTCCTGGGG-3' (sense);

FcF2,
(SEQ ID NO: 84)
5'-CCGTGCCCACGGTGCCCAGCACCTGAACTCCTGGGG-3' (sense);

FcF3,
(SEQ ID NO: 85)
5'-GCACCTGAACTCCTGGGG-3' (sense);

FcR,
(SEQ ID NO: 86)
5'-GTCGAGGCTGATCAGCGG-3' (antisense);

FcR1,
(SEQ ID NO: 87)
5'-CTCCTATGCGGCCGCTTTACCCGGAGACAG-3' (antisense);

HcF,
(SEQ ID NO: 88)
5'-CCCCAACCACAACCAAAACCACAACCACAACCACAACCA
AACCAC-3' (sense);

HcR,
(SEQ ID NO: 89)
5'-TGGACATTTGGGACACGTGCATTCTGGTTCAGGTTTTGGTTGTGGT
TTTGGTTGTGG-3' (antisense);

HhF,
(SEQ ID NO: 90)
5'-ACCCCACTTGGTGACACAACTCACACATGCCCACGGTGCCCAGAGC
CCAAA-3' (sense);

HhR,
(SEQ ID NO: 91)
5'-TGGGCACCGTGGGCACGGGGGAGGTGTGTCACAAGATTTGGGCTCT
GGGCA-3' (antisense);

HSAPR2,
(SEQ ID NO: 92)
5'-ctcctatgcggccgcatcatcgtcgccccacaaacaccccagcgt
ggcaa-3' (antisense);

HSAPR3,
(SEQ ID NO: 93)
5'-ccccagcgtggcaaacatatatcttctgggtggcgctggccctt
atcgtcatc-3' (antisense).

Figure 22:
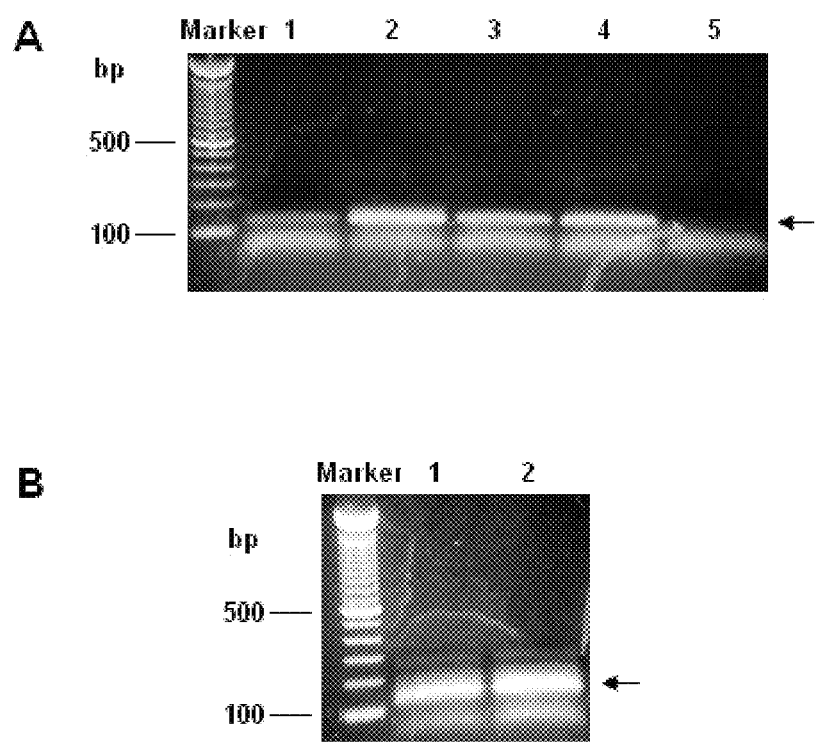
FIG. 22 demonstrates the results obtained from PCR amplification of CDR2 and CDR3 repertoires from cDNA. (A) Eight recombinations of primers were used for CDR2s amplification as described below in Example 2. The products of the first five recombinations (H2-F1/H2-R1, H2-F1/H2-R2, H2-F1/H2-R5, H2-F2/H2-R3, H2-F3/H2-R1, and H2-F3/H2-R2) were shown on lane 1 to lane 5, respectively. (B) Three recombinations of primers were used for CDR3 amplification. The products of the first two recombinations (H3-F1/H3R and H3-F2/H3R) were shown on lane 1 and 2, respectively. The correct-sized bands were indicated by arrows.
Figure 29:
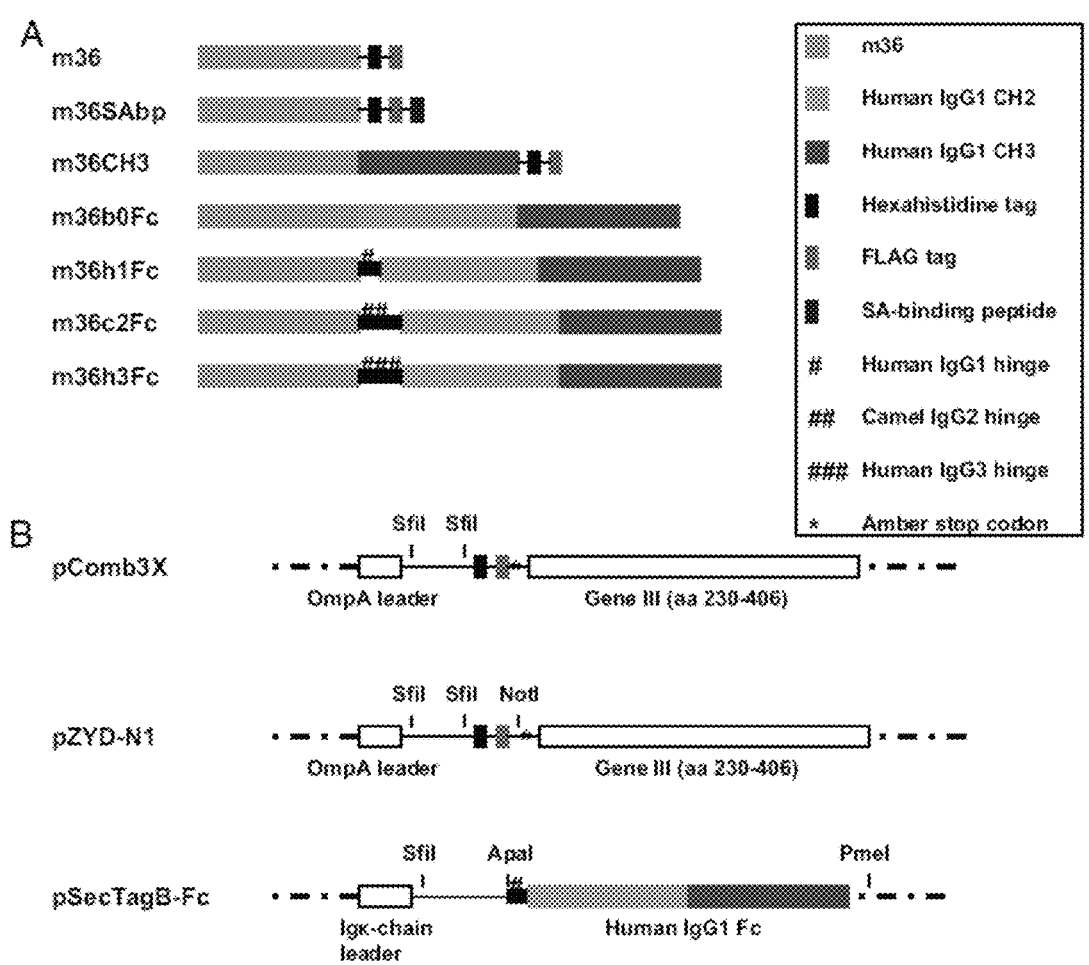
FIG. 29 depicts the cloning of m36 and its fusion proteins of FIG. 28. Schematic representation of the m36 gene cassettes, and its fusion proteins (A) and plasmids used for cloning (B).

For construction of m36CH3, the m36 gene was amplified by PCR (primer: m36F1 and m36R4) with m36-encoding plasmid pCom36 as a template. The CH3 gene of human IgG1 was PCR (primer: CH3F and CH3R) amplified from plasmid pSecTagB-Fc, which encoded the human IgG1 Fc portion (FIG. 29). M36 fragment was joined to CH3 by overlapping PCR performed in a volume of 100 µl using both templates (in the same molarities) for 7 cycles in the absence of primers and additional 15 cycles in the presence of primers (500 pM of m36F1 and CH3R, respectively). The m36CH3 products appended with SfiI restriction sites on both sides were digested and cloned into a phagemid vector (FIG. 22). To generate m36b0Fc, m36 gene was amplified by PCR using primer m36F1 and m36R5. Human IgG1 Fc gene was obtained by PCR amplification using pSecTagB-Fc as the template and primer FcF3 and FcR1. M36 fragment was joined to Fc as described above. The products were digested with SfiI and NotI, and cloned into pZYD-N1, which was developed by the inventors to have a NotI site after the FLAG tag. The vector pSecTagB-Fc was used for construction of m36h1Fc, m36c2Fc, and m36h3Fc. The m36 fragment was PCR amplified using primer m36F and m36R1, digested with SfiI and ApaI, and cloned into pSec-TagB-Fc to generate m36h1Fc. M36c2Fc was cloned by amplifying m36 fragment (primer: m36F and m36R2), human IgG1 Fc (primer: FcF1 and FcR), and camel IgG2 hinge (primer: HcF and HcR). The m36 fragment was fused to camel IgG2 hinge and the product was subsequently joined to Fc by overlapping PCR. The resultant full-length m36c2Fc product was digested with SfiI and PmeI, and cloned into pSecTagB-Fc vector. In the same way m36h3Fc was constructed except for the use of primer m36F and m36R3 for m36 amplification, primer FcF2 and FcR for human IgG1 Fc amplification, and primer HhF and HhR for human IgG3 hinge amplification. To generate m36SAbp, the m36 fragment was amplified using primer m36F1 and HSAPR3, purified and further extended by PCR using primer m36F1 and HSAPR2. The products were digested with SfiI and NotI, and cloned into pZYD-N1.

Expression and Purification of m36 and its Fusion Proteins

M36, m36SAbp, m36CH3 and m36b0Fc were expressed in *E. coli* HB2151 as described previously (Zhu et al, 2006). The bacterial pellet was collected after centrifugation at 5,000×g for 10 min and resuspended in PBS (pH 7.4) containing 0.5 mU polymixin B (Sigma-Aldrich, St. Louis, Mo.). After 30 min incubation with rotation at 50 rpm at room temperature, it was centrifuged at 25,000×g for 25 min at 4° C. The supernatant was used for purification of m36, m36SAbp and m36CH3 by immobilized metal ion affinity chromatography (IMAC) using Ni-NTA resin (Qiagen, Valencia, Calif.) according to manufacturer's protocols. For purification of m36b0Fc, nProtein A Sepharose 4 Fast Flow (GE Healthcare, Piscataway, N.J.) was used. M36h1Fc, m36c2Fc and m36h3Fc were expressed in 293 free style cells. CellFectin (Invitrogen, Carlsbad, Calif.) was used to transfect 293 free style cells according to the instructions of the manufacturer. Three days posttransfection, the culture supernatant was harvested and used for purification of m36h1Fc, m36c2Fc and m36h3Fc by using nProtein A Sepharose 4 Fast Flow.

Binding ELISA

Antigens were coated on Corning EIA/RIA high-binding 96-well plates (Corning Inc., Corning, N.Y.) at 50 ng per well overnight at 4° C. and blocked with 3% nonfat milk in PBS. Threefold serially diluted antibody was added in the absence or presence of sCD4 at 2 µg/ml final concentration and incubated at room temperature for 2 h. The plates were washed with PBS containing 0.05% Tween 20. Bound m36, m36SAbp or m36CH3 was detected by HRP-conjugated anti-FLAG tag antibody (Sigma-Aldrich, St. Louis, Mo.). The m36 fusion proteins with human IgG1 Fc were detected by HRP-conjugated anti-human IgG (Fc-specific) antibody (Sigma-Aldrich, St. Louis, Mo.). The assay was developed at 37° C. with ABST substrate (Roche, Indianapolis, Ind.) and monitored at 405 nm. The half-maximal binding ($EC_5$s) was calculated by fitting the data to the Langmuir adsorption isotherm.

Competition ELISA

Antigens were coated and blocked as described above. M36 at a concentration leading to 90% maximum binding was premixed with threefold serially diluted competitors without or with sCD4 at 2 µg/ml final concentration. Mixtures were subsequently added to each well and incubated. Bound m36 was detected and the assay was developed as described above.

Measurement of m36 Oligomerization

Superdex75 column was calibrated with protein molecular mass standard of 14 (ribonuclease A), 25 (chymotrypsin), 44 (ovalbumin), 67 (albumin), 158 (aldolase), 232 (catalase), 440 (ferritin) and 669 (thyroglobulin) kDa. Purified m36 in PBS were loaded onto the column that had been pre-equilibrated. The proteins were eluted with PBS at 0.5 ml/min.

Pseudovirus Neutralization Assay

Viruses pseudotyped with HIV-1 Envs were prepared by cotransfection of 70-80% confluent 293T cells with pNL4-3.luc.E-R- and pSV7d constructs encoding HIV-1 Envs using the PolyFect transfection reagent (Qiagen, Valencia, Calif.) according to manufacturer's instruction. Pseudotyped viruses were obtained after 24 h by centrifugation and filtration of cell culture through 0.45-µm filters. For neutralization, viruses were mixed with different concentrations of antibodies and/or sCD4 at 8 nM for 1 h at 37° C., and then the mixture was added to ~1.5×10$^4$ HOS-CD4-CCR5 (used for all R5 and dual tropic viruses) or HOS-CD4-CXCR4 cells grown in each well of 96-well plates. Luminesence was measured after 48 h using the Bright-Glo Luciferase Assay System (Promega, Madison, Wis.) and a LumiCount microplate luminometer (Turner Designs). Mean relative light units (RLU) for duplicate wells were determined. Percentage inhibition was calculated by the following formula: (1—average RLU of antibody-containing wells/average RLU of virus-only wells)×100. $IC_{50}$ and $IC_{90}$ of neutralization were assigned for the antibody concentration at which 50% and 90% neutralization were observed, respectively.

Results of Example 3:

Selection of m36 from a Newly Constructed Human Antibody VH Library.

Examples 1 and 2 discuss the identification of a phage-displayed heavy chain only antibody by panning of a large (size~1.5×10$^{10}$) human naive IgM library against an Env. The VH of this Fab, designated as m0, was independently folded, stable, highly soluble, monomeric, and expressed at high levels in bacteria. MO was used as a scaffold to construct a large (size 2.5×10$^{10}$) highly-diversified phage-displayed human VH library by grafting naturally occurring CDR2s and CDR3s of heavy chains from five human antibody Fab libraries, and randomly mutating four putative solvent-accessible residues in CDR1 (FIG. 23).

A VH, m36, was selected from this library as the highest affinity binder by using the sequential antigen panning (SAP) methodology (Zhang et al., 2003) with HIV-1 Envs from clade B: a truncated Env lacking the transmembrane portion and the cytoplasmic tail from R2 (gp140$_{R2}$) (Quinnan et al., 1999) or from JRFL (gp140$_{JRFL}$), and gp120 from Bal in complex with CD4 as a fusion protein (gp120$_{Bal}$-CD4) (Fouts T R et al., 2000). M36 is monomeric in PBS at pH 7.4 as determined by size exclusion chromatography, and runs on SDS-PAGE gels and size exclusion chromatography with an apparent molecular weight (MW) of 14-15 kDa which is close to the calculated MW (14.972 kDa, including the His and FLAG tags) (data not shown). It is highly soluble, thermally stable, and is expressed at high levels in bacteria (~30 mg per L of culture) (data not shown). The m36 framework and CDR1 are closest to those encoded by the VH3-23 germline gene; the CDR2—to the VH4-34 (FIG. 24). All m36 CDRs contain negatively charged and neutral but not basic residues. The CDR3 sequence is relatively short.

Potent Cross-Reactive Neutralization of Pseudotyped HIV-1 Isolates by m36

Figure 26:
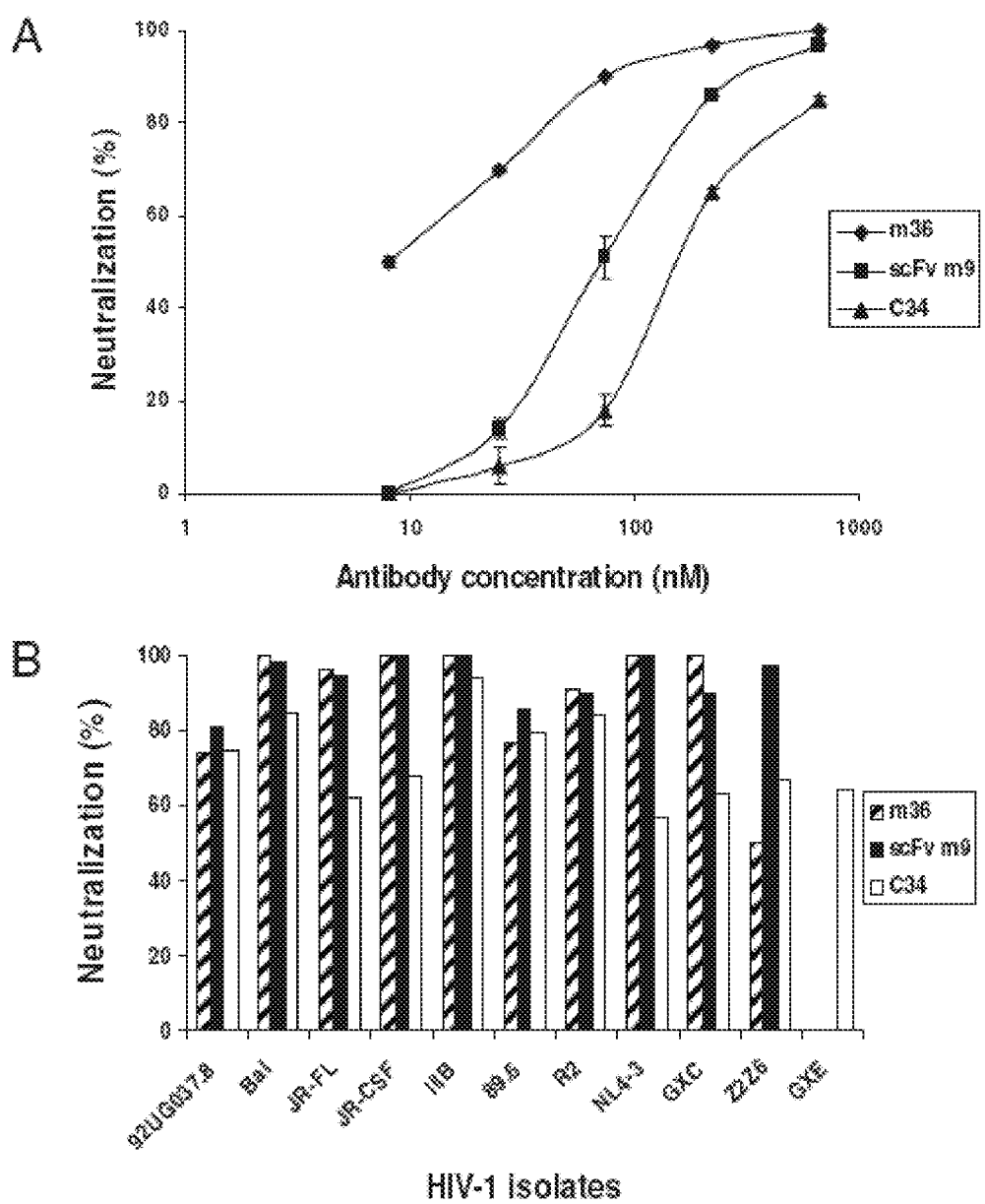
FIG. 26 shows potent m36-mediated neutralization of viruses pseudotyped with Envs of HIV-1 primary isolates. (A) Dose-dependent inhibition of Bal by m36, scFv and C34, respectively. (B) Percentage inhibition of a panel of viruses by m36, scFv m9 and C34 at 667 nM, respectively.
Figure 27:
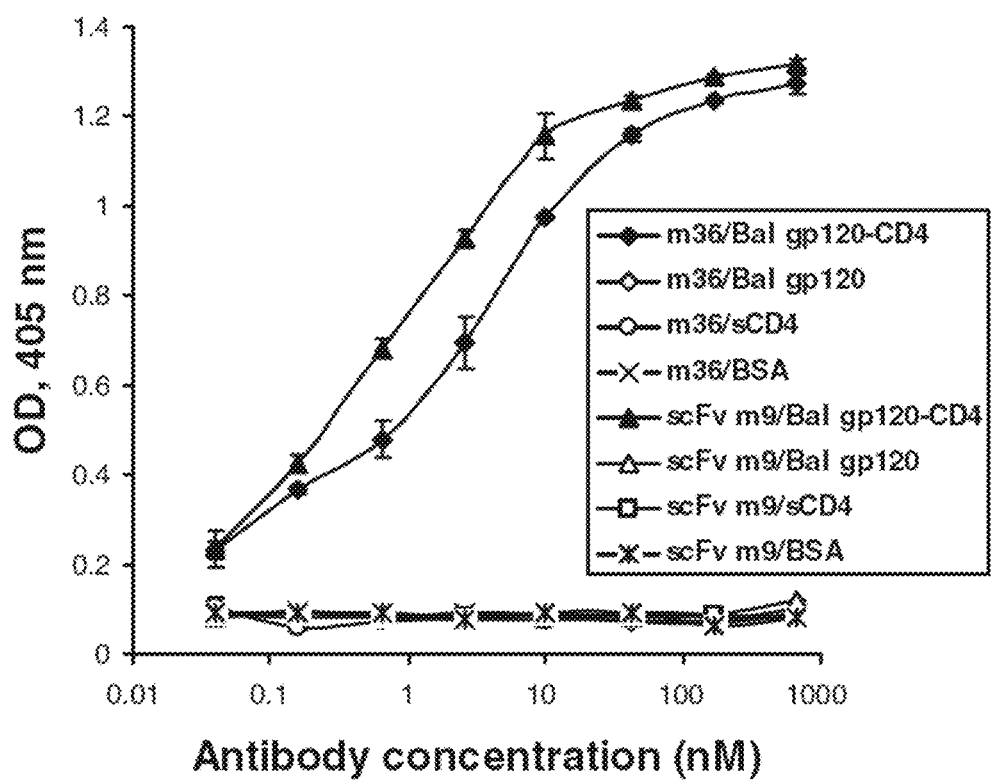
FIG. 27 show that the binding of m36 to gp120 is induced by the gp120 interaction with CD4. The graph shows the specific binding of m36 to $gp120_{Bal}$-CD4 but not to $gp120_{Bal}$ alone. See FIG. 15 for complementary data showing the competition of m36 with a CD4i antibody (IgG m16) for binding to $gp120_{Bal}$-CD4.

To determine the potency and breadth of HIV-1 neutralization by m36, viruses pseudotyped with Envs from HIV-1 isolates representing clades A, B, C, D and E were used. M36 neutralized six isolates from clade B, one isolate from clade C, and one isolate from clade A with potency on average two-fold higher (two-fold lower $IC_{50}$s on molar basis) than that of the broadly cross-reactive neutralizing CD4i antibody scFv m9 (Zhang et al., 2004) (FIG. 25); m9 is an in vitro matured derivative of X5 and exhibits superior neutralizing activity compared to known cross-reactive HIV-1 neutralizing antibodies (b12, 4E10, 2F5, 2G12, X5) when tested against more than 100 isolates. M36 exhibited remarkable activity against the clade C isolate GXC-44 and the clade B isolate NL4-3 with very low $IC_{90}$s (FIG. 32). It exhibited lower neutralization activity against the clade B isolate 89.6 and the clade-D isolate Z2Z6 compared to scFv m9. M36 and scFv m9 did not neutralize the clade E isolate GXE at concentrations up to 667 nM. M36 was also on average more potent than the peptide C34 (FIG. 25); C34 (10) is a gp41-derived peptide which exhibits HIV-1 entry inhibitory activity comparable to or higher than that of the FDA approved peptide entry inhibitor T20 (DP178, FUZEON™) which shares significant sequence homology with C34 although inhibits entry by somewhat different mechanism involving binding to multiple sites (Liu S et al., 2005). The inhibitory activity of m36 was dose-dependent (FIG. 26A). Complete (100%) inhibition of 4 out of 7 clade B isolates and the isolate from clade C was achieved at 667 nM concentration; note that at the equivalent molar concentration C34 did not completely inhibit any of the isolates tested, and m9 completely inhibited 3 out of 7 clade B isolates (FIG. 26B). These results suggest that m36 is a potent cross-reactive neutralizing antibody with potency and breadth of neutralization for this panel of isolates on average better than that of scFv m9 and C34. These three inhibitors exhibit differential neutralization profiles and could be used in combination.

M36 Binding to Gp120 is Enhanced by CD4 and Decreased by the CD4-Binding Site Antibody m14

Figure 3:
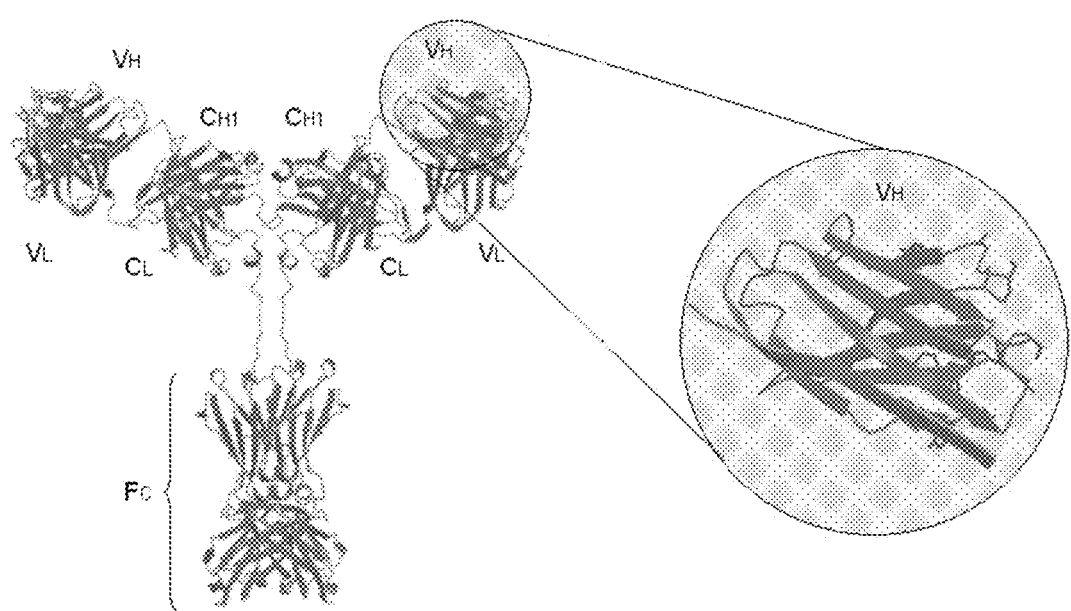
FIG. 3 depicts in ribbon form the general structure of a human IgG molecule, with emphasis on the VH region, which may form a domain antibody of the invention.

To approximately localize the m36 epitope and begin to elucidate the underlying mechanisms of neutralization, we measured binding of m36 to Envs from different isolates alone and in complex with CD4 as well as the m36 competition with well characterized antibodies. M36 bound to gp120$_{Bal}$-CD4 with high affinity (EC$_{50}$~2.5 nM) but not to gp120$_{Bal}$ or to soluble CD4 (sCD4) and BSA, as measured by an ELISA assay (FIG. 3A). It also bound to gp140 from a clade C isolate GXC-44 (gp140$_{GXC-44}$) in the presence of sCD4 but notably it did bind although weaker to gp140$_{GXC-44}$ alone too (data not shown) in contrast to gp120$_{Bal}$ (data not shown). Similarly, it also bound to another clade B Env, a tethered gp140 from 89.6, without complexation with CD4 but its binding was enhanced after gp140 bound to CD4 (data not shown). In both cases the binding as function on concentration deviated from a classical Langmuir-type isotherm likely due to a more complex multi-stage mechanism of antibody-antigen interactions. As expected for a CD4-induced (CD4i) antibody, m36 competed for binding to gp120$_{Bal}$-CD4 with the CD4i antibody m16 (FIG. 3B) but not with the CD4 binding site (CD4bs) antibody m14 which was used as a negative control. Notably, it also competed for binding to gp140$_{GXC-44}$ in the absence of CD4 with m14 (data not shown). These results suggest that m36 is a cross-reactive CD4i antibody which binds to an epitope localized close to the CD4 binding site.

The m36 Epitope is Sterically Restricted

Figure 28:
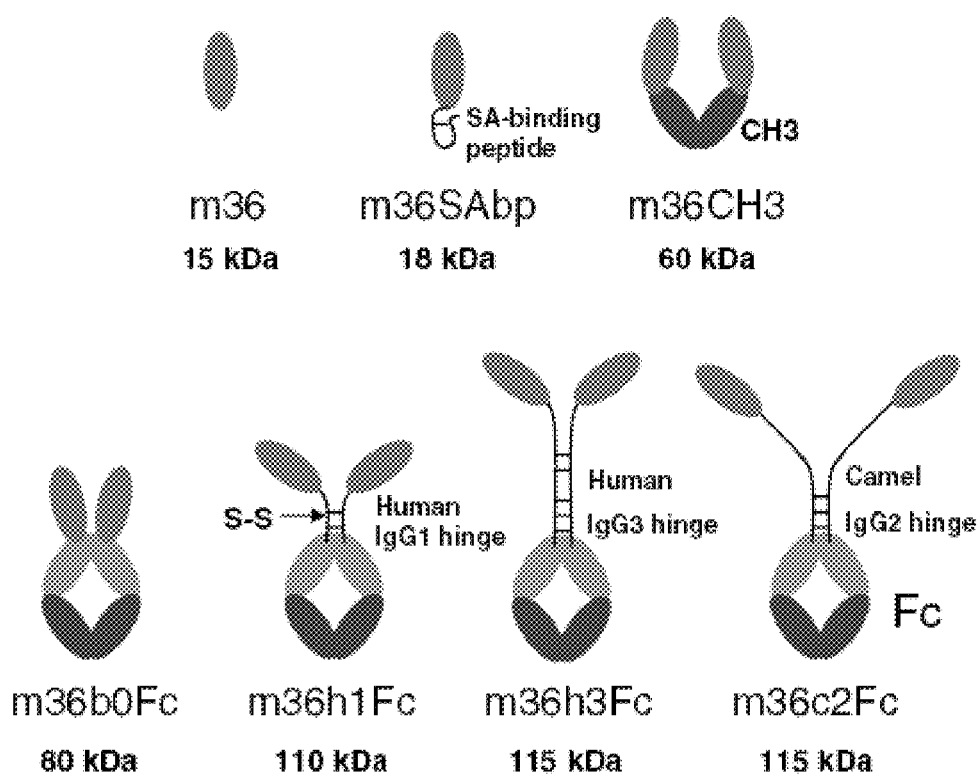
FIG. 28 depicts the design of m36 fusion proteins described in Example 3. Schematic representation of m36 fused with SAbp, human IgG1 CH3 domain or Fc. The names of the constructs and their molecular weights are also shown. The sequences of the SAbp and the linkers used to join m36 with Fc by human IgG1 and IgG3 hinge, and camel IgG2 hinge are QRHPEDICLPRWGCLWGDDD (SEQ ID NO: 1), DKTHTCPPCP (SEQ ID NO: 2), EPKIPQPQPK-PQPQPQPQPKPQPKPEPECTCPKCP (SEQ ID NO: 3), and
ELKTPLGDTTHTCPRCPEPKSCDTPPPCPRCP (SEQ ID NO: 4), respectively.

In an attempt to further elucidate possible mechanisms of neutralization, access to the m36 epitope was examined to determine whether it was sterically restricted. To answer this question several m36 fusion proteins with MWs ranging from 18 to 115 kDa (FIG. 28 and FIG. 29) were designed and tested. First, the binding of the m36 fusion proteins to Env complexed with CD4 was carried out to assure that the additional protein does not interfere with binding. Next, the neutralizing activity of the fusion proteins was evaluated.

Figure 30:
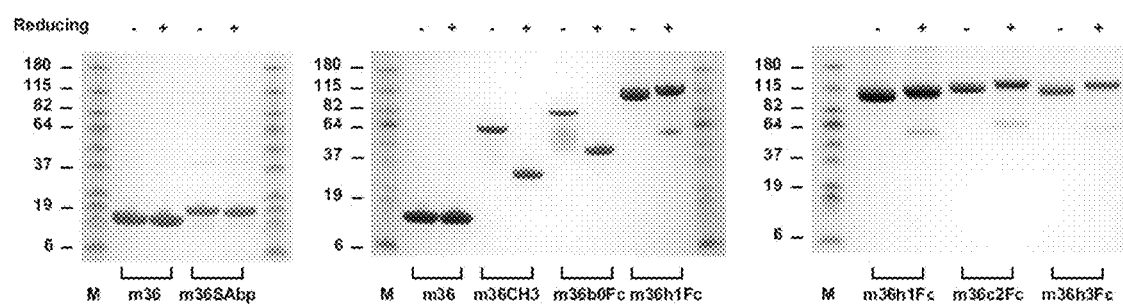
FIG. 30 shows SDS-PAGE of m36 and its fusion proteins under reducing (−) and non-reducing (+) conditions.
Figure 31:
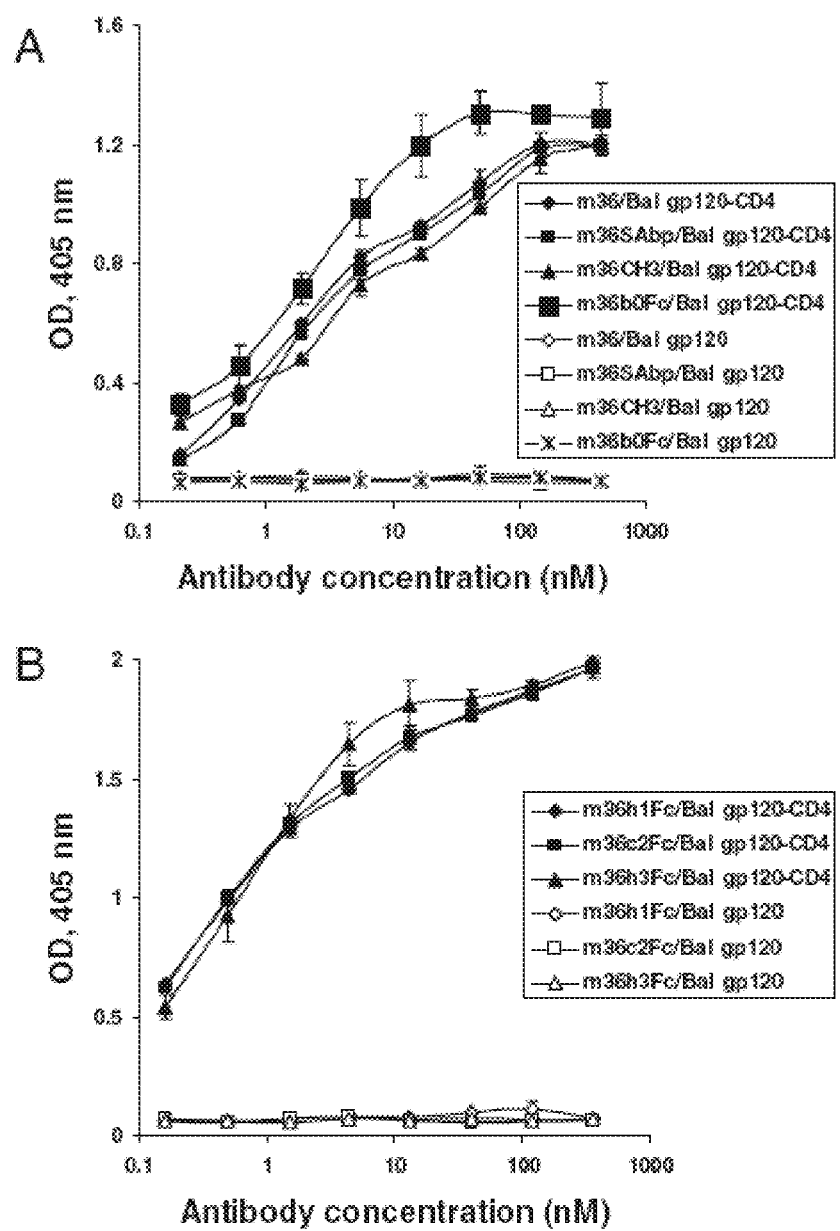
FIG. 31 demonstrates that m36 and its fusion proteins have similar binding activities. (A) Binding of m36, m36SAbp, m36CH3 and m36b0Fc to $gp120_{Bal}$-CD4 and $gp120_{Bal}$, respectively. (B) Binding of m36h1Fc, m36c2Fc and m36h3Fc to $gp120_{Bal}$-CD4 and $gp120_{Bal}$, respectively.

The m36 was fused to a serum albumin binding peptide (SAbp), human IgG1 CH3 domain and Fc without a peptide linker; these fusion proteins, m36SAbp (MW~18 kDa), m36CH3 (MW~60 kDa) and m36b0Fc (MW~80 kDa), respectively (FIG. 4), were expressed in E. coli HB2151 and purified. In the other three fusion proteins m36 was joined with human IgG1 Fc by a human IgG1 hinge (m36h1Fc, MW~110 kDa), a camel IgG2 hinge (m36c2Fc, MW~115 kDa) or a human IgG3 hinge (m36h3Fc, MW~115 kDa), respectively (FIG. 28), and expressed in mammalian 293 suspension cells. All fusion proteins, except m36SAbp, were dimeric in PBS, pH 7.4 as shown on non-reducing SDS-PAGE gels (FIG. 30). They all exhibited comparable to or higher than m36 binding to gp120$_{Bal}$-CD4 as measured by ELISA. M36SAbp and m36CH3 showed binding comparable to that of m36 (FIG. 31A); m36b0Fc bound slightly better. The three fusion proteins expressed in mammalian cells (m36h1Fc, m36c2Fc and m36h3Fc) exhibited the highest binding strengths with EC$_{50}$~0.5 nM (FIG. 31B). All antibodies at concentrations up to 870 nM did not show significant binding to gp120$_{Bal}$ in the absence of CD4.

In spite of the preserved or even higher affinity (avidity), all fusion proteins, except m36SAbp, exhibited significantly weaker neutralizing activity when compared to m36 side by side in the same experiment (FIG. 25 and FIG. 32). The increased size of m36CH3 resulted in loss of neutralization against 7 of 10 isolates compared to m36, and for those neutralized (IIIB, 89.6 and NL4-3) the IC$_{50}$s were significantly higher than the corresponding ones for m36. With an additional increase in molecular size, m36b0Fc further lost neutralization against the T cell line adapted (TCLA) isolate, IIIB, and had a decreased inhibitory activity against 89.6 and NL4-3. Notably, the three fusion proteins with long flexible linkers neutralized HIV-1 significantly better than the bacterially expressed m36b0Fc which does not have a linker and m36CH3 which has much smaller molecular size (FIG. 25 and FIG. 32). They neutralized five isolates, one of them (89.6) even with potency higher than that of m36 likely due to their bivalency leading to avidity and other effects. These isolates were neutralized equally well by m36h1Fc, m36c2Fc and m36h3Fc indicating that further increase in the length of the linker may not affect the neutralization activity. Fusion of m36 with the relatively much smaller SAbp resulted only in slight but not significant decrease of the neutralizing activity (FIG. 25).

Figure 33:
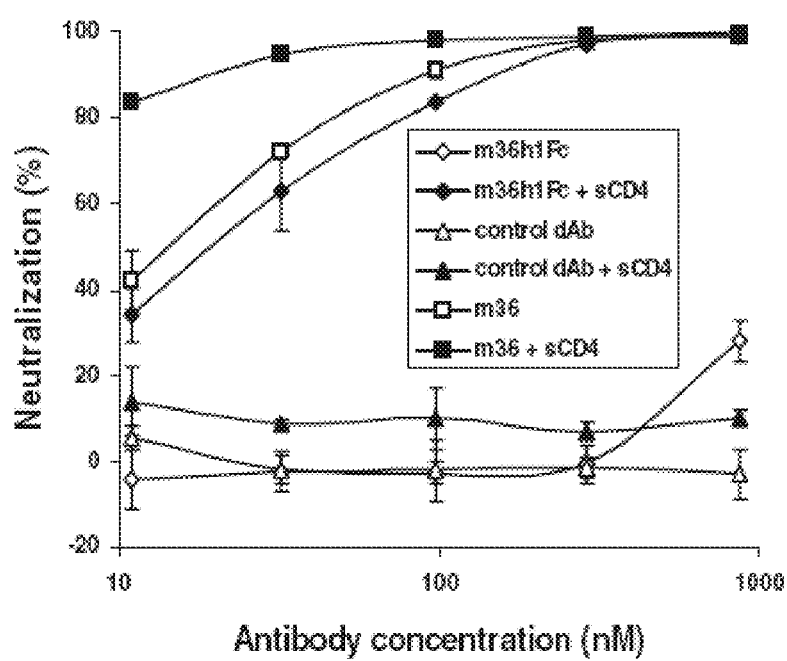
FIG. 33 demonstrates that pre-triggering (sensitization) of virus by sCD4 dramatically increases neutralization by large molecules fused with m36. Viruses were pre-inoculated with different concentrations of antibodies and/or sCD4 at 8 nM for 1 h at 37° C., and then the mixture was added to $1.5 \times 10^4$ HOS-CD4-CCR5 cells grown in each well of 96-well plates. Luminesence was measured 48 h post infection and percentage inhibition was calculated as described in Example 3.

Next, it was investigated whether the access to the m36 epitope on intact virions before entry into cells could be enhanced by CD4. M36 and its fusion proteins were preincubated with pseudovirus and in the presence of a low concentration of sCD4. The m36h1Fc fusion protein alone at up to 870 nM and sCD4 alone at 8 nM or combined with a control domain antibody-Fc fusion protein exhibited low neutralizing activity of about 25% and 10%, respectively (FIG. 33). Preincubation of the Bal pseudovirus with both m36h1Fc and sCD4 resulted in a dramatic increase in neutralization—up to 100% (FIG. 33); similar increase was also observed with JRFL pseudovirus. Taken together these results suggest that the m36 epitope is sterically obstructed and fully accessible during virus entry only by relatively small size molecules.

Discussion Fo Example 3 Results:

Example 3 demonstrates that dAbs could bind to conserved structures that are inaccessible or partially accessible during virus entry for molecules of larger size comparable to that of full-size antibodies generated by the human immune system. Such antibodies could not only be potentially useful as candidate therapeutics against viruses, including HIV-1, which can protect highly conserved structures that are vital for virus replication, but can also help identify those conserved structures with implications for the development of small molecule inhibitors, and elucidation of mechanisms of entry and evasion of immune responses.

The binding of the Env to receptor and coreceptor molecules may result in the exposure of conserved structures that could be used as antigens for selection of cross-reactive neutralizing antibodies. The identification and characterization of the potent broadly cross-reactive human Fab X5 (Moulard et al., 2002) provided supporting evidence. The crystal structure of its complex with gp120-CD4 enabled the localization of the highly conserved epitope overlapping the putative coreceptor binding site very close to the CD4 binding site (Huang et al, 2005). However, unexpectedly, IgG1 X5 on average exhibited lower potency than Fab and scFv likely due to its larger size. Because the crystal structure of Fab X5 complexed with gp120-CD4 suggested that only its heavy chain contacts gp120, decreasing the size to a single VH could further increase the potency of X5. However, efforts to isolate stable VH X5 or VH X5-like dAbs by rational design, mutagenesis and screening have failed. Similarly, efforts to develop a stable highly soluble VH dAb based on an HIV-1 gp120-specific heavy chain only antibody have also failed likely due to certain extent of hydrophobicity that is important for its structural stability.

As disclosed in the present application, including in the above Examples, the present inventors identified another heavy chain only antibody which as an isolated VH, m0, exhibited high stability and solubility. As outlined in the present application, including in Example 2, a large highly diversified library using as a scaffold m0 was constructed. The high diversification of the library was achieved by two strategies—grafting highly diverse CDR2s and CDR3s from five separate libraries including one from HIV-1-infected individuals, and randomly mutating four residues in the CDR1 to residues frequently found in antibody CDRs. This library was used for selection of m36 and could also be useful for isolation of dAbs against other antigens.

Access of full-size antibodies to CD4i epitopes can be restricted during virus entry into cells. The crystal structures of two CD4i antibodies, X5 and 17b, in complex with gp120 and sCD4, indicate that access to their epitopes requires long protruding heavy chain CDR3s. Most of the known CD4i antibodies have long CDR3s that could play an important role in accessing sterically restricted areas. Their CDR3s are highly acidic (FIG. 24) and the closest germline VH gene for this group of antibodies is VH1-69. A smaller group of CD4i antibodies have relatively short CDR3s, acidic CDR2s and VH1-24 gene usage. M36 appears to be the only representative of a third group characterized with short CDR3, acidic CDR1 and VH3-23 gene usage (FIG. 24). Because of its small size it may not need a long CDR3 for access to sterically restricted structures.

M36 exhibited on average higher neutralizing activity than scFv m9, which has been recently shown to be superior to the best characterized cross-reactive HIV-1 neutralizing antibodies b12, 2G12, 2F5 and 4E10, and than C34, a peptide similar to the fusion inhibitor T20 (FUZEON™) which is in clinical use. It was hypothesized that a dimer of m36 could have even higher potency due to avidity effects and used CH3 as a dimerization domain. However, m36CH3 was significantly weaker than m36 indicating that the m36 epitope is fully accessible during virus entry only by antibody domains or smaller molecules (FIG. 25). A larger fusion protein, M36b0Fc, was poorer inhibitor most likely due to the increased molecular size. However, a fusion protein with a human IgG1 hinge region as a linker between m36 and Fc, m36h1Fc, neutralized better several isolates than m36CH3 and m36b0Fc despite an increase in size (FIG. 25). For some isolates (89.6, NL4-3 and GXC-44) its potency was as high as that of m36. It was further hypothesized that the long linker may provide a flexibility needed for the m36 to reach its epitope combined with an increased binding due to avidity effects resulting from the m36h1Fc bivalency. However, fusion proteins with even longer hinge regions (from camel antibodies, m36cFc, or from human IgG3, m36h3Fc) did not exhibit higher potency than m36h1Fc (FIG. 25) possibly due to compensation of the flexibility effect by an increase in the effective hydrodynamic size of the molecules leading to a decrease in the accessibility of the m36 epitope.

The neutralizing activity of the m36 fusion proteins was dramatically increased for viruses sensitized (pre-triggered) by sCD4 (soluble CD4) to expose the m36 epitope (FIG. 33). These data not only provide evidence for the restricted nature of the m36 epitope during entry but also suggest the possibility to develop novel m36-based potential therapeutics, e.g. fusion proteins of m36 with sCD4 or small molecule mimics of CD4. These molecules could neutralize the virus before it binds to cell surface-associated CD4 while m36 is likely to exert its major neutralizing activity after the virus binds to the cell surface-associated CD4 which triggers the conformational changes in gp120 leading to exposure of its epitope.

To our knowledge m36 is the first identified and characterized HIV-1 neutralizing human dAb. It could have potential as a therapeutic adding a new target to the growing family of entry inhibitors. Although its half-life in vivo is likely to be very short our findings that a fusion protein with an SAbp (serum albumin-binding peptide) retains about the same neutralizing activity as m36 indicates the possibility to improve its pharmacokinetics. We found that the m36SAbp binds to serum albumins from human (HSA), bovine (BSA) and mouse (MSA) (data not shown) indicating that such possibility is realistic. The epitope of m36 is sterically restricted and may not be directly used to develop potential vaccine immunogens. However, it is highly conserved and therefore could be also useful as a tool to explore mechanisms of entry and to understand how HIV-1 guards its conserved structures and evade neutralizing immune responses.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES

The following references are incorporated herein by reference and are cited in the above specification.

Abergel C, Claverie J M. A strong propensity toward loop formation characterizes the expressed reading frames of the D segments at the Ig H and T cell receptor loci Eur J Immunol. 1991 December; 21(12):3021-5.

Bond C J, Marsters J C, Sidhu S S Contributions of CDR3 to V H H domain stability and the design of monobody scaffolds for naïve antibody libraries J Mol Biol. 2003 Sep. 19; 332(3):643-55.

Bradbury et al. Antibodies from phage antibody libraries Journal of Immunological Methods 290 (2004) 29-49.

Brown N L. (1999) Imaging gene expression using antibody probes. Methods Mol Biol. 122:75-91.

Chan D C, Fass D, Berger J M, Kim P S (1997) Core structure of gp41 from the HIV envelope glycoprotein. Cell 89:263-273.

Chen W et al. (2008) Construction of a large phage-displayed human antibody domain library with a scaffold based on a newly identified highly soluble, stable heavy chain variable domain, J. Mol. Biol. 382:779-789.

Chingwei V. Lee, Wei-Ching Liang, Mark S. Dennis, Charles Eigenbrot Sachdev S. Sidhu and Germaine Fuh. High-affinity Human Antibodies from Phage-displayed Synthetic Fab Libraries with a Single Framework Scaffold. J. Mol. Biol. (2004) 340, 1073-1093.

Decker J M et al. (2005) Antigenic conservation and immunogenicity of the HIV coreceptor binding site. J Exp Med 201:1407-1419.

de Haard H J, van Neer N, Reurs A, Hufton S E, Roovers R C, Henderikx P, de BruYne A P, Arends J W, Hoogenboom H R. A large non-immunized human Fab fragment phage library that permits rapid isolation and kinetic analysis of high affinity antibodies. J Biol Chem. 1999, 274(26): 18218-30.

Dimitrov D S, Fusin: a place for HIV-1 and T4 cells to meet, 1996, Nat. Med., 2:640-641.

Dimitrov D S, Virus entry: molecular mechanisms and biomedical applications, Nat. Rev. Microbiol., 2004, February; 2(2): 109-22.

Ewert, S., Cambillau, C., Conrath, K. & Plückthun, A. (2002). Biophysical properties of camelid VHH domains compared to those of human VH3 domains. Biochemistry, 41, 3628-3636.

Fauci A S (2008) 25 years of HIV. Nature 453:289-290.

Fellouse F A, Wiesmann C, Sidhu S S. Synthetic antibodies from a four-amino-acid code: a dominant role for tyrosine in antigen recognition Proc Natl Acad Sci USA. 2004 Aug. 24; 101(34):12467-72. Epub 2004 Aug. 11.

Fouts T R et al. (2000) Expression and characterization of a single-chain polypeptide analogue of the human immunodeficiency virus type 1 gp120-CD4 receptor complex. J Virol 74:11427-11436.

Holt, L. J., Herring, C., Jespers, L. S., Woolven, B. P., and Tomlinson, I. M. (2003) Domain antibodies: proteins for therapy. Trends Biotechnol. 21, 484-490.

Hoogenboom H R, Chames P Natural and designer binding sites made by phage display technology Immunol Today. 2000 August; 21(8):371-8.

Huang C C et al. (2005) Structure of a V3-containing HIV-1 gp120 core. Science 310:1025-1028.

Huang C C et al. (2004) Structural basis of tyrosine sulfation and VH-gene usage in antibodies that recognize the HIV type 1 coreceptor-binding site on gp120. Proc Natl Acad Sci USA 101:2706-2711.

Jain, R. K. and Baxter, L. T. (1988) Mechanisms of heterogeneous distribution of monoclonal antibodies and other macromolecules in tumors: significance of elevated interstitial pressure. Cancer Res. 48, 7022-7032.

Jirholt P, Ohlin M, Borrebaeck C A, Söderlind E. Exploiting sequence space: shuffling in vivo formed complementarity determining regions into a master framework. Gene. 1998 Jul. 30; 215(2):471-6.

Jones et al., Conformational changes in cell surface HIV-1 envelope glycoproteins are triggered by cooperation between cell surface CD4 and co-receptors, 1998, J. Biol. Chem., 273:404-409.

Kabat, E. A., Wu, T. T., Perry, H. M., Gottesmann, K. S. & Foeller, C., Sequences of proteins of immunological interest, NIH publication 91-3242 (1991).

Kohler, G. and Milstein, C. (1975) Continuous cultures of fused cells secreting antibody of predefined specificity. Nature 256, 495-497.

Kortt, A. A., Guthrie, R. E., Hinds, M. G., Power, B. E., Ivancic, N., Caldwell, J. B. et al. (1995). Solution properties of Escherichia coli-expressed VH domain of anti-neuraminidase antibody NC41. J. Protein Chem. 14, 167-178.

Kozlowski S, Swann P. Current and future issues in the manufacturing and development of monoclonal antibodies. Adv Drug Deliv Rev. 2006 Aug. 7; 58(5-6):707-22. Epub 2006 May 22.

Kwong et al., HIV-1 evades antibody-mediated neutralization through conformational masking of receptor-binding sites, Nature, 2002, 420:678-682.

Kwong P D et al. (1998) Structure of an HIV gp120 envelope glycoprotein in complex with the CD4 receptor and a neutralizing human antibody. Nature 393:648-659.

Labrijn et al., Access of antibody molecules to the conserved coreceptor binding site on glycoprotein gp120 is sterically restricted on primary human immunodeficiency virus type 1, Journal of Virology, October 2003, 77: 10557-10565.

Liu S et al. (2005) Different from the HIV fusion inhibitor C34, the anti-HIV drug Fuzeon (T-20) inhibits HIV-1 entry by targeting multiple sites in gp41 and gp120. J Biol Chem 280:11259-11273.

McCafferty, J., Griffiths, A D, Winter, G. and Chiswell, D J, Nature, 348 (1990) 552-554.

Moulard et al., Broadly cross-reactive HIV-1-neutralizing human monoclonal Fab selected for binding to gp120-CD4-CCR5 complexes, Proc. Natl. Acad. Sci., 2002, 99:6913-6918.

Muyldermans, Christian Cambillau and Lode Wyns. Recognition of antigens by single domain antibody fragments: the superfluous luxury of paired domains TRENDS in Biochemical Sciences Vol. 26 No. 4, 230-235 April 2001.

Myszka et al., 2000, Energetics of the HIV gp120-CD4 binding reaction, Proc. Natl. Acad. Sci. USA, 97:9026-9031.

Nicaise, et al., Protein Science, 2004, 13:1882-1891.

Parren et al., The neutralizing antibody response to HIV-1: viral evasion and escape from humoral immunity, AIDS, 1999, 13:S137-S162.

Perno C F et al. (2008) Overcoming resistance to existing therapies in HIV-infected patients: the role of new antiretroviral drugs. J Med Virol 80:565-576.

Poignard et al., gp120: biologic aspects of structural features, 2001, Annu. Rev. Immunol., 2001, 19:253-274).

Potter K N, Li Y, Capra J D. Staphylococcal protein A simultaneously interacts with framework region 1, complementarity-determining region 2, and framework region 3 on human VH3-encoded Igs. J Immunol. 1996 Oct. 1; 157(7):2982-8.

Prabakaran P, Dimitrov A S, Fouts T R, Dimitrov D S (2007) Structure and Function of the HIV Envelope Glycoprotein as Entry Mediator, Vaccine Immunogen, and Target for Inhibitors. Adv Pharmacol 55:33-97.

Quinnan G V, Zhang P F, Fu D W, Dong M, Alter H J (1999) Expression and characterization of HIV type 1 envelope protein associated with a broadly reactive neutralizing antibody response. AIDS Res Hum Retroviruses 15:561-570.

Randen I, Potter K N, Li Y, Thompson K M, Pascual V, Førre O, Natvig J B, Capra J D Complementarity-determining region 2 is implicated in the binding of staphylococcal protein A to human immunoglobulin VHIII variable regions Eur J Immunol. 1993 October; 23(10):2682-6.

Ray N, Doms R W (2006) HIV-1 coreceptors and their inhibitors. Curr Top Microbiol Immunol 303:97-120.

Sattentau et al., Conformational changes induced in the human immunodeficiency virus envelope glycoprotein by soluble CD4 binding, 1991, J. Exp. Med., 174:407-415.

Sattentau et al., Conformational changes induced in the envelope glycoproteins of the human and simian immunodeficiency viruses by soluble receptor binding, 1993, J. Virol., 67:7383-7393.

Schellekens, H. (2002) Immunogenicity of therapeutic proteins: clinical implications and future prospects. Clin. Ther. 24, 1720-1740.

Scott et al., 2001. Phage-display vectors, p. 2.1-2.19. In Carlos F. Barbas III, Dennis R. Burton, Jamie K. Scott, and Gregg J. Silverman (ed.), Phage display: A laboratory manual, 1st ed. Cold Spring Harbor Laboratory Press, Cold Spring Harbor, N.Y.

Sheets M D, Amersdorfer P, Finnern R, Sargent P, Lindquist E, Schier R, Hemingsen G, Wong C, Gerhart J C, Marks J D. (1998) Efficient construction of a large nonimmune phage antibody library: the production of high-affinity human single-chain antibodies to protein antigens. Proc Natl Acad Sci USA. 1998 May 26; 95(11):6157-62.

Söderlind, E., Strandberg, L., Jirholt, P., Kobayashi, N., Alexeival, V., Åberg, A. M., et al. (2000) Recombining germline-derived CDR sequences for creating diverse single framework antibody libraries. Nature Biotechnol. 18, 852-856.

Ward, E. S., Güssow, D., Griffiths, A. D., Jones, P. T., and Winter, G. (1989) Binding activities of a repertoire of single immunoglobulin variable domains secreted from *Escherichia coli*. Nature 341, 544-546.

Wu T T, Johnson G, Kabat E A Length distribution of CDRH3 in antibodies Proteins. 1993 May; 16(1): 1-7.

Wyatt et al., The HIV-1 envelope glycoproteins: fusogens, antigens and immunogens, Science, 1995, 69:5723-5733.

Zhang, M. Y., Y. Shu, S. K. Phogat, X. Xiao, F. Cham, A. Choudhary, Y. R. Feng, I. Sanz, S. Rybak, C. C. Broder, G. V. Quinnan, Jr., T. Evans, and D. S. Dimitrov. 2003. Broadly cross-reactive HIV neutralizing human monoclonal antibody Fab selected by sequential antigen panning of a phage display library. J. Immunol. Methods 283:17-25.

Zhang M Y et al. (2004) Improved breadth and potency of an HIV-1-neutralizing human single-chain antibody by random mutagenesis and sequential antigen panning. J Mol Biol 335:209-219.

Zhang, Q., Chen, G., Liu, X., and Qian, Q. (2007) Monoclonal antibodies as therapeutic agents in oncology and antibody gene therapy. Cell Res. 17, 89-99.

Zhu Z, Dimitrov A S, Bossart K N, Crameri G, Bishop K A, Choudhry V, Mungall B A, Feng Y R, Choudhary A, Zhang M Y, Feng Y, Wang L F, Xiao X, Eaton B T, Broder C C, Dimitrov D S Potent neutralization of Hendra and Nipah viruses by human monoclonal antibodies J Virol. 2006 January; 80(2):891-9.

What is claimed is:

1. A fusion protein comprising:
   a domain antibody that binds a CD4-induced (CD4i) epitope on Env and comprises CDR1, CDR2, and CDR3 of m36 (SEQ ID NO: 96), and a framework having an amino acid sequence with (1) at least 90% sequence identity with SEQ ID NO: 96 (m36) or (2) at least 90% sequence identity with SEQ ID NO: 94 (m0), and
   a fusion partner polypeptide selected from the group consisting of (i) serum albumin-binding protein or peptide, (ii) CD4 or a fragment thereof, (iii) a human immunoglobulin Fc domain, and (iv) human immunoglobulin CH3 domain.

2. The fusion protein of claim 1, wherein the fusion protein is immunoconjugated to one or more cytotoxic agents, chemotherapeutic agents, natural or synthetic toxins, radioactive isotopes, or antiviral agents.

3. The fusion protein of claim 2, wherein the antiviral agent is at least one of zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, adefovir, clevadine, entecavir, or pleconaril.

4. The fusion protein of claim 2, wherein the fusion partner polypeptide is fused to the domain antibody via a linker.

5. The fusion protein of claim 4, wherein the linker is an immunoglobulin hinge region.

6. The fusion protein of claim 1, wherein the amino acid sequence of the domain antibody
   has the amino acid sequence of SEQ ID NO: 96 (m36).

7. The fusion protein of claim 1, wherein the fusion partner polypeptide is the human immunoglobulin Fc domain that is fused to the domain antibody via a linker comprising an immunoglobulin hinge region.

8. A pharmaceutical composition comprising a therapeutically effective amount of the fusion protein of claim 1, and a pharmaceutically acceptable carrier.

9. The pharmaceutical composition of claim 8, further comprising a therapeutically effective amount of soluble CD4 or functional fragment thereof.

* * * * *

```
                        SEQUENCE LISTING

<160> NUMBER OF SEQ ID NOS: 152

<210> SEQ ID NO 1
<211> LENGTH: 20
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 1

Gln Arg His Pro Glu Asp Ile Cys Leu Pro Arg Trp Gly Cys Leu Trp
1               5                   10                  15

Gly Asp Asp Asp
            20

<210> SEQ ID NO 2
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 2

Asp Lys Thr His Thr Cys Pro Pro Cys Pro
1               5                   10

<210> SEQ ID NO 3
<211> LENGTH: 35
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 3

Glu Pro Lys Ile Pro Gln Pro Gln Pro Lys Pro Gln Pro Gln Pro Gln
1               5                   10                  15

Pro Gln Pro Lys Pro Gln Pro Lys Pro Glu Pro Glu Cys Thr Cys Pro
            20                  25                  30

Lys Cys Pro
        35

<210> SEQ ID NO 4
<211> LENGTH: 32
<212> TYPE: PRT
<213> ORGANISM: Artificial Sequence
```

```
<220> FEATURE:
<221> NAME/KEY: source
<223> OTHER INFORMATION: Synthetic polypeptide

<400> SEQUENCE: 4

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

<210> SEQ ID NO 5
<211> LENGTH: 57
<212> TYPE: DNA
<213> ORGANISM: Artificial Sequence
<220> FEATURE:
<221> NAME/KEY: source
<223> OTHER INFORMATION: Synthetic primer

<400> SEQUENCE: 5
gcggacccag ctcatttcat aakmakmgaa akmgaaakma gaggctgcac aggagag        57

<210> SEQ ID NO 6
<211> LENGTH: 51
<212> TYPE: DNA
<213> ORGANISM: Artificial Sequence
<220> FEATURE:
<221> NAME/KEY: source
<223> OTHER INFORMATION: Synthetic primer

<400> SEQUENCE: 6
gaggaggagg aggaggaggc ggggcccagg cggcccaggt gcagctggtg c              51

<210> SEQ ID NO 7
<211> LENGTH: 45
<212> TYPE: DNA
<213> ORGANISM: Artificial Sequence
<220> FEATURE:
<221> NAME/KEY: source
<223> OTHER INFORMATION: Synthetic primer

<400> SEQUENCE: 7
gaaatgagct gggtccgcca ggctccagga caasgscttg agtgg                     45

<210> SEQ ID NO 8
<211> LENGTH: 45
<212> TYPE: DNA
<213> ORGANISM: Artificial Sequence
<220> FEATURE:
<221> NAME/KEY: source
<223> OTHER INFORMATION: Synthetic primer

<400> SEQUENCE: 8
gaaatgagct gggtccgcca ggctccaggg aaggccctgg agtgg                     45

<210> SEQ ID NO 9
<211> LENGTH: 45
<212> TYPE: DNA
<213> ORGANISM: Artificial Sequence
<220> FEATURE:
<221> NAME/KEY: source
<223> OTHER INFORMATION: Synthetic primer
<220> FEATURE:
<221> NAME/KEY: modified_base
<222> LOCATION: (36)..(36)
<223> OTHER INFORMATION: a, c, g, t, unknown or other

<400> SEQUENCE: 9
```
gaaatgagct gggtccgcca ggctccaggg aagggnctrg agtgg                45

<210> SEQ ID NO 10
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 10
attgtctctg gagatggtga ccctkycctg raacty           36

<210> SEQ ID NO 11
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (34)..(34)
<223> OTHER INFORMATION: a, c, g, t, unknown or other

<400> SEQUENCE: 11
attgtctctg gagatggtga atcggccctt cacnga           36

<210> SEQ ID NO 12
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 12
attgtctctg gagatggtga ctmgactctt gaggga           36

<210> SEQ ID NO 13
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 13
attgtctctg gagatggtga cstggccttg gaagga           36

<210> SEQ ID NO 14
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 14
attgtctctg gagatggtaa accgtcctgt gaagcc           36

<210> SEQ ID NO 15
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 15
accctgagag ccgaggacac rgcyttrtat tactgt        36

<210> SEQ ID NO 16
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 16
accctgagag ccgaggacac agccayrtat tactgt        36

<210> SEQ ID NO 17
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 17
accctgagag ccgaggacac rgcygtrtat tactgt        36

<210> SEQ ID NO 18
<211> LENGTH: 34
<212> TYPE: DNA
<213> ORGANISM: Artificial Sequence
<220> FEATURE:
<221> NAME/KEY: source
<223> OTHER INFORMATION: Synthetic primer

<400> SEQUENCE: 18
gtggccggcc tggccacttg aggagacggt gacc        34

<210> SEQ ID NO 19
<211> LENGTH: 21
<212> TYPE: DNA
<213> ORGANISM: Artificial Sequence
<220> FEATURE:
<221> NAME/KEY: source
<223> OTHER INFORMATION: Synthetic primer

<400> SEQUENCE: 19
accatctcca gagacaattc c        21

<210> SEQ ID NO 20
<211> LENGTH: 19
<212> TYPE: DNA
<213> ORGANISM: Artificial Sequence
<220> FEATURE:
<221> NAME/KEY: source
<223> OTHER INFORMATION: Synthetic primer

<400> SEQUENCE: 20
gtcctcggct ctcagggtg        19

<210> SEQ ID NO 21
<211> LENGTH: 43
<212> TYPE: DNA
<213> ORGANISM: Artificial Sequence
<220> FEATURE:
<221> NAME/KEY: source
<223> OTHER INFORMATION: Synthetic primer -continued

<400> SEQUENCE: 21
tggtttcgct accgtggccc aggcggccca ggtgcagctg gtg         43

<210> SEQ ID NO 22
<211> LENGTH: 41
<212> TYPE: DNA
<213> ORGANISM: Artificial Sequence
<220> FEATURE:
<221> NAME/KEY: source
<223> OTHER INFORMATION: Synthetic primer

<400> SEQUENCE: 22
gtcgccgtgg tggtggtggt ggtggccggc ctggccactt g           41

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 23

Ile Asn His Ser Gly Ile Thr
1               5

<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 24

Ile Asn His Ser Gly Ser Thr
1               5

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 25

Ile Asp Asn Ser Gly Ser Thr
1               5

<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 26

Ile Asn Thr Asp Gly Asp Ile Pro
1               5

<210> SEQ ID NO 27
<211> LENGTH: 7
<212> TYPE: PRT
<213> ORGANISM: Artificial Sequence

```
<220> FEATURE:
<221> NAME/KEY: source
<223> OTHER INFORMATION: Synthetic peptide

<400> SEQUENCE: 27

Ile Tyr His Arg Gly Asn Thr
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 28

Ile Asn His Thr Gly Ser Thr
1               5

<210> SEQ ID NO 29
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 29

Ile Thr Gly Ser Gly Asp Thr Thr
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 30

Ile Asn Asp Ser Gly Asn Thr
1               5

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 31

Val Gly Gly Ser Gly Glu Arg Thr
1               5

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 32

Ile Asn Ser Asn Gly Ser Val Thr
1               5
```

```
<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 33

Ile Ser Tyr Asp Gly Ser Ile Lys
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 34

Ile Tyr His Ser Gly Ser Thr
1               5

<210> SEQ ID NO 35
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 35

Ile Asn Ser Ser Ser Ser Tyr Ile
1               5

<210> SEQ ID NO 36
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 36

Ile Ser Gly Asp Gly Gly Ala Thr
1               5

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 37

Ile Tyr Tyr Ser Gly Ser Thr
1               5

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
```

```
<400> SEQUENCE: 38

Ile Lys Gln Asp Gly Ser Val Val
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 39

Ile Ser Tyr Asp Gly Ser Asn Lys
1               5

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 40

Ile Tyr Ser Gly Gly Thr Thr
1               5

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 41

Ile Ser Asn Ser Gly Gly Thr Ile
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 42

Ile Tyr Ser Gly Gly Ser Thr
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 43

Ile Arg Tyr Asp Gly Ser Asn Lys
1               5

<210> SEQ ID NO 44
<211> LENGTH: 11
<212> TYPE: PRT
```

```
<213> ORGANISM: Artificial Sequence
<220> FEATURE:
<221> NAME/KEY: source
<223> OTHER INFORMATION: Synthetic peptide

<400> SEQUENCE: 44

Ala Ile Val Asp Thr Ala Met Val Trp Asp Tyr
1               5                   10

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 45

Ala Ala Ser Gly Ser Tyr Ser Asp Tyr
1               5

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 46

Ala Thr His Asp Tyr Gly Asp Ser Phe Glu Ser
1               5                   10

<210> SEQ ID NO 47
<211> LENGTH: 14
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 47

Ala Arg Ile Gly Asp Gly Phe Phe Ser Asp Ala Phe Glu Ile
1               5                   10

<210> SEQ ID NO 48
<211> LENGTH: 12
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 48

Ala Gly Asp Tyr Gly Ser Gly Ser Glu Phe Glu Asn
1               5                   10

<210> SEQ ID NO 49
<211> LENGTH: 14
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 49

Ala Lys Tyr Thr Trp Asn Ser Asp Ser Gly Trp Gly Glu Leu
1               5                   10
```

```
<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 50

Val Gly Tyr Gly Ala Asp Gln Asp Asp Cys
1               5                   10

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 51

Ala Thr His Asp Tyr Gly Asp Ser Phe Glu Ser
1               5                   10

<210> SEQ ID NO 52
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 52

Ala Ala Asp Thr Gly Asn Ala Phe Asp Ile
1               5                   10

<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 53

Ala Gly Ser Ser Gly Trp Leu His Glu Tyr
1               5                   10

<210> SEQ ID NO 54
<211> LENGTH: 9
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 54

Ala Thr Asp Gln Ala Gly Ile Glu His
1               5

<210> SEQ ID NO 55
<211> LENGTH: 9
<212> TYPE: PRT
<213> ORGANISM: Artificial Sequence
<220> FEATURE:
<221> NAME/KEY: source
<223> OTHER INFORMATION: Synthetic peptide
```

<400> SEQUENCE: 55

Ala Thr Ser Val Gly Tyr Glu Glu Leu
1               5

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 56

Ala Met Ser Asp Gly Tyr Ser Ala Thr Asp Val
1               5                   10

<210> SEQ ID NO 57
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 57

Ala Leu Thr Asp Ser Ser Ser Tyr Asp Tyr
1               5                   10

<210> SEQ ID NO 58
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 58

Ala Phe Tyr Met Arg Gly Ala Ile Leu Glu Tyr
1               5                   10

<210> SEQ ID NO 59
<211> LENGTH: 13
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 59

Ala Ala Tyr Asp Phe Trp Ser Gly Ser Tyr Pro Glu Tyr
1               5                   10

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 60

Ala Ile Tyr Gly Gly Asn Ser Gly Gly Glu Tyr
1               5                   10

<210> SEQ ID NO 61
<211> LENGTH: 10

<212> TYPE: PRT
<213> ORGANISM: Artificial Sequence
<220> FEATURE:
<221> NAME/KEY: source
<223> OTHER INFORMATION: Synthetic peptide

<400> SEQUENCE: 61

Ala Arg Ile Asp Arg Asp Gly Asp Glu His
1               5                   10

<210> SEQ ID NO 62
<211> LENGTH: 9
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 62

Ala Gly Ser Gly Ser Tyr Ser Asp Tyr
1               5

<210> SEQ ID NO 63
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 63

Ala Arg Asp Trp Gly Tyr Ser Pro Glu Asp
1               5                   10

<210> SEQ ID NO 64
<211> LENGTH: 17
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 64

Ala Arg Thr Pro Pro Arg Ile Ala Ala Ala Gly Met Arg Tyr Phe Asp
1               5                   10                  15

Leu

<210> SEQ ID NO 65
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 65

Ala Arg Asp Trp Gly Tyr Ser Pro Glu Asp
1               5                   10

<210> SEQ ID NO 66
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 66

Ala Arg Ala Asp Tyr Arg Ser Thr Asp His
1               5                   10

<210> SEQ ID NO 67
<211> LENGTH: 8
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 67

Ala Arg Gln Val Ala Ala Pro Val
1               5

<210> SEQ ID NO 68
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 68

Ala Arg Asp Trp Gly Tyr Ser Pro Glu Asp
1               5                   10

<210> SEQ ID NO 69
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 69

Val Arg Asp Trp Gly Tyr Asn Pro Glu Asp
1               5                   10

<210> SEQ ID NO 70
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 70

Val Arg Asp Trp Gly Tyr Asn Pro Glu Asp
1               5                   10

<210> SEQ ID NO 71
<211> LENGTH: 20
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 71

Ala Arg Gly Thr Gly Leu His Asp Tyr Gly Asp Tyr Trp Ala His Thr
1               5                   10                  15

Glu Phe Asp Tyr
            20

<210> SEQ ID NO 72

```
<211> LENGTH: 10
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 72

Ala Arg Asp Trp Gly Tyr Ser Pro Glu Asp
1               5                   10

<210> SEQ ID NO 73
<211> LENGTH: 15
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 73

Ala Arg Gly Val Asp Tyr Gly Asp Tyr Gly Gly Tyr Phe Asp Tyr
1               5                   10                  15

<210> SEQ ID NO 74
<211> LENGTH: 43
<212> TYPE: DNA
<213> ORGANISM: Artificial Sequence
<220> FEATURE:
<221> NAME/KEY: source
<223> OTHER INFORMATION: Synthetic primer

<400> SEQUENCE: 74
tggtttcgct accgtggccc agccggccca ggtgcagctg gtg            43

<210> SEQ ID NO 75
<211> LENGTH: 43
<212> TYPE: DNA
<213> ORGANISM: Artificial Sequence
<220> FEATURE:
<221> NAME/KEY: source
<223> OTHER INFORMATION: Synthetic primer

<400> SEQUENCE: 75
tggtttcgct accgtggccc aggcggccca ggtgcagctg gtg            43

<210> SEQ ID NO 76
<211> LENGTH: 33
<212> TYPE: DNA
<213> ORGANISM: Artificial Sequence
<220> FEATURE:
<221> NAME/KEY: source
<223> OTHER INFORMATION: Synthetic primer

<400> SEQUENCE: 76
gtgagttttg tcgggccctg aggagacggt gac            33

<210> SEQ ID NO 77
<211> LENGTH: 42
<212> TYPE: DNA
<213> ORGANISM: Artificial Sequence
<220> FEATURE:
<221> NAME/KEY: source
<223> OTHER INFORMATION: Synthetic primer

<400> SEQUENCE: 77
tggttgtggt tggggtatct tgggttctga ggagacggtg ac            42
```

<210> SEQ ID NO 78
<211> LENGTH: 39
<212> TYPE: DNA
<213> ORGANISM: Artificial Sequence
<220> FEATURE:
<221> NAME/KEY: source
<223> OTHER INFORMATION: Synthetic primer

<400> SEQUENCE: 78
gtcaccaagt ggggttttga gctctgagga gacggtgac                      39

<210> SEQ ID NO 79
<211> LENGTH: 30
<212> TYPE: DNA
<213> ORGANISM: Artificial Sequence
<220> FEATURE:
<221> NAME/KEY: source
<223> OTHER INFORMATION: Synthetic primer

<400> SEQUENCE: 79
ttctcggggc tgccctgagg agacggtgac                                30

<210> SEQ ID NO 80
<211> LENGTH: 30
<212> TYPE: DNA
<213> ORGANISM: Artificial Sequence
<220> FEATURE:
<221> NAME/KEY: source
<223> OTHER INFORMATION: Synthetic primer

<400> SEQUENCE: 80
caggagttca ggtgctgagg agacggtgac                                30

<210> SEQ ID NO 81
<211> LENGTH: 18
<212> TYPE: DNA
<213> ORGANISM: Artificial Sequence
<220> FEATURE:
<221> NAME/KEY: source
<223> OTHER INFORMATION: Synthetic primer

<400> SEQUENCE: 81
gggcagcccc gagaacca                                             18

<210> SEQ ID NO 82
<211> LENGTH: 42
<212> TYPE: DNA
<213> ORGANISM: Artificial Sequence
<220> FEATURE:
<221> NAME/KEY: source
<223> OTHER INFORMATION: Synthetic primer

<400> SEQUENCE: 82
gtggtggtgg tggtggccgg cctggccttt acccggagac ag                  42

<210> SEQ ID NO 83
<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 83
acgtgtccca aatgtccagc acctgaactc ctgggg                         36

<210> SEQ ID NO 84

<211> LENGTH: 36
<212> TYPE: DNA
<213> ORGANISM: Artificial Sequence
<220> FEATURE:
<221> NAME/KEY: source
<223> OTHER INFORMATION: Synthetic primer

<400> SEQUENCE: 84
ccgtgcccac ggtgcccagc acctgaactc ctgggg                    36

<210> SEQ ID NO 85
<211> LENGTH: 18
<212> TYPE: DNA
<213> ORGANISM: Artificial Sequence
<220> FEATURE:
<221> NAME/KEY: source
<223> OTHER INFORMATION: Synthetic primer

<400> SEQUENCE: 85
gcacctgaac tcctgggg                                        18

<210> SEQ ID NO 86
<211> LENGTH: 18
<212> TYPE: DNA
<213> ORGANISM: Artificial Sequence
<220> FEATURE:
<221> NAME/KEY: source
<223> OTHER INFORMATION: Synthetic primer

<400> SEQUENCE: 86
gtcgaggctg atcagcgg                                        18

<210> SEQ ID NO 87
<211> LENGTH: 30
<212> TYPE: DNA
<213> ORGANISM: Artificial Sequence
<220> FEATURE:
<221> NAME/KEY: source
<223> OTHER INFORMATION: Synthetic primer

<400> SEQUENCE: 87
ctcctatgcg gccgctttac ccggagacag                           30

<210> SEQ ID NO 88
<211> LENGTH: 52
<212> TYPE: DNA
<213> ORGANISM: Artificial Sequence
<220> FEATURE:
<221> NAME/KEY: source
<223> OTHER INFORMATION: Synthetic primer

<400> SEQUENCE: 88
ccccaaccac aaccaaaacc acaaccacaa ccacaaccac aaccaaaacc ac  52

<210> SEQ ID NO 89
<211> LENGTH: 57
<212> TYPE: DNA
<213> ORGANISM: Artificial Sequence
<220> FEATURE:
<221> NAME/KEY: source
<223> OTHER INFORMATION: Synthetic primer

<400> SEQUENCE: 89
tggacatttg ggacacgtgc attctggttc aggttttggt tgtggttttg gttgtgg  57

<210> SEQ ID NO 90
<211> LENGTH: 51

-continued

<212> TYPE: DNA
<213> ORGANISM: Artificial Sequence
<220> FEATURE:
<221> NAME/KEY: source
<223> OTHER INFORMATION: Synthetic primer

<400> SEQUENCE: 90
accccacttg gtgacacaac tcacacatgc ccacggtgcc cagagcccaa a        51

<210> SEQ ID NO 91
<211> LENGTH: 51
<212> TYPE: DNA
<213> ORGANISM: Artificial Sequence
<220> FEATURE:
<221> NAME/KEY: source
<223> OTHER INFORMATION: Synthetic primer

<400> SEQUENCE: 91
tgggcaccgt gggcacgggg gaggtgtgtc acaagatttg ggctctgggc a        51

<210> SEQ ID NO 92
<211> LENGTH: 51
<212> TYPE: DNA
<213> ORGANISM: Artificial Sequence
<220> FEATURE:
<221> NAME/KEY: source
<223> OTHER INFORMATION: Synthetic primer

<400> SEQUENCE: 92
ctcctatgcg gccgcatcat cgtcgcccca caaacacccc cagcgtggca a        51

<210> SEQ ID NO 93
<211> LENGTH: 54
<212> TYPE: DNA
<213> ORGANISM: Artificial Sequence
<220> FEATURE:
<221> NAME/KEY: source
<223> OTHER INFORMATION: Synthetic primer

<400> SEQUENCE: 93
cccccagcgt ggcaaacata tatcttctgg gtggcgctgg cccttatcgt catc     54

<210> SEQ ID NO 94
<211> LENGTH: 125
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 94

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Ser Phe Ser Thr Tyr
            20                  25                  30

Glu Met Ser Trp Val Arg Gln Ala Pro Gly Lys Gly Leu Glu Trp Val
        35                  40                  45

Ser Pro Ile Ser Gly Ser Gly Gly Asn Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Val Tyr Tyr Cys
                85                  90                  95

Ala Lys Gly Pro Pro Val Trp Ser Gly Tyr Tyr Phe Ala Asp Gly Phe 100                 105                 110
Asp Ile Trp Gly Gln Gly Thr Met Val Thr Val Ser Ser
        115                 120                 125

<210> SEQ ID NO 95
<211> LENGTH: 375
<212> TYPE: DNA
<213> ORGANISM: Artificial Sequence
<220> FEATURE:
<221> NAME/KEY: source
<223> OTHER INFORMATION: Synthetic polynucleotide
<220> FEATURE:
<221> NAME/KEY: CDS
<222> LOCATION: (1)..(375)

<400> SEQUENCE: 95 cag gtg cag ctg gtg cag tct ggg gga ggc ttg gta cag cct gga ggg    48
Gln Val Gln Leu Val Gln Ser Gly Gly Gly Leu Val Gln Pro Gly Gly
1               5                   10                  15 tcc ctg aga ctc tcc tgt gca gcc tct gga ttc agc ttc agt act tat    96
Ser Leu Arg Leu Ser Cys Ala Ala Ser Gly Phe Ser Phe Ser Thr Tyr
            20                  25                  30 gaa atg agc tgg gtc cgc cag gct cca ggg aag ggg ctg gag tgg gtc   144
Glu Met Ser Trp Val Arg Gln Ala Pro Gly Lys Gly Leu Glu Trp Val
        35                  40                  45 tca cct att agt ggt agt ggt ggt aac tca tac tac gca gac tcc gtg   192
Ser Pro Ile Ser Gly Ser Gly Gly Asn Ser Tyr Tyr Ala Asp Ser Val
    50                  55                  60 aag ggc cgg ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac acc ctg aga gcc gag gac acg gcc gta tat tac tgt   288
Leu Gln Met Asn Thr Leu Arg Ala Glu Asp Thr Ala Val Tyr Tyr Cys
                85                  90                  95 gcg aaa ggc ccc ccg gtt tgg agt ggt tat tat ttc gct gat ggt ttt   336
Ala Lys Gly Pro Pro Val Trp Ser Gly Tyr Tyr Phe Ala Asp Gly Phe
            100                 105                 110 gat atc tgg ggc caa ggg aca atg gtc acc gtc tct tca               375
Asp Ile Trp Gly Gln Gly Thr Met Val Thr Val Ser Ser
        115                 120                 125

<210> SEQ ID NO 96
<211> LENGTH: 117
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 96

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

```
Ile Tyr Gly Gly Asn Ser Gly Gly Glu Tyr Trp Gly Gln Gly Thr Leu
            100                 105                 110

Val Thr Val Ser Ser
        115

<210> SEQ ID NO 97
<211> LENGTH: 351
<212> TYPE: DNA
<213> ORGANISM: Artificial Sequence
<220> FEATURE:
<221> NAME/KEY: source
<223> OTHER INFORMATION: Synthetic polynucleotide
<220> FEATURE:
<221> NAME/KEY: CDS
<222> LOCATION: (1)..(351)

<400> SEQUENCE: 97 cag gtg cag ctg gtg cag tct ggg gga ggc ttg gta cag cct gga ggg      48
Gln Val Gln Leu Val Gln Ser Gly Gly Gly Leu Val Gln Pro Gly Gly
1               5                   10                  15 tcc ctg aga ctc tcc tgt gca gcc tct gct ttc gat ttc tct gat tat      96
Ser Leu Arg Leu Ser Cys Ala Ala Ser Ala Phe Asp Phe Ser Asp Tyr
            20                  25                  30 gaa atg agc tgg gtc cgc cag gct cca ggg aag ggg ctg gag tgg att     144
Glu Met Ser Trp Val Arg Gln Ala Pro Gly Lys Gly Leu Glu Trp Ile
        35                  40                  45 ggg gaa atc aat gat agt gga aac acc att tac aat ccg tcc ctc aag     192
Gly Glu Ile Asn Asp Ser Gly Asn Thr Ile Tyr Asn Pro Ser Leu Lys
    50                  55                  60 agt cga gtc acc atc tcc aga gac aat tcc aag aac acg ctg tat ctg     240
Ser Arg Val Thr Ile Ser Arg Asp Asn Ser Lys Asn Thr Leu Tyr Leu
65                  70                  75                  80 caa atg aac acc ctg aga gcc gag gac aca gcc ata tat tac tgt gcg     288
Gln Met Asn Thr Leu Arg Ala Glu Asp Thr Ala Ile Tyr Tyr Cys Ala
                85                  90                  95 ata tat ggt ggt aac tcc ggg gga gag tac tgg ggc cag ggc acc ctg     336
Ile Tyr Gly Gly Asn Ser Gly Gly Glu Tyr Trp Gly Gln Gly Thr Leu
            100                 105                 110 gtc acc gtc tcc tca                                                  351
Val Thr Val Ser Ser
        115

<210> SEQ ID NO 98
<211> LENGTH: 81
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: CDS
<222> LOCATION: (16)..(81)

<400> SEQUENCE: 98
caggaggaat ttaaaatgaa aaagacagct atcgcgattg cagtggcact ggctggtttc      60
gctaccgtgg cccaggcggc c                                                81

<210> SEQ ID NO 99
<211> LENGTH: 22
<212> TYPE: PRT
<213> ORGANISM: Artificial Sequence
<220> FEATURE:
<221> NAME/KEY: source
<223> OTHER INFORMATION: Synthetic peptide
```

<400> SEQUENCE: 99

Met Lys Lys Thr Ala Ile Ala Ile Ala Val Ala Leu Ala Gly Phe Ala
1               5                   10                  15

Thr Val Ala Gln Ala Ala
            20

<210> SEQ ID NO 100
<211> LENGTH: 117
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 100

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
            115

<210> SEQ ID NO 101
<211> LENGTH: 119
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 101

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Phe
            20                  25                  30

Tyr Met Tyr Trp Val Arg Gln Ala Pro Gly Lys Gly Leu Glu Trp Met
        35                  40                  45

Gly Leu Ile Asp Pro Glu Asp Ala Asp Thr Met Tyr Ala Glu Lys Phe
    50                  55                  60

Arg Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asp Pro Trp Glu Leu Asn Ala Phe Asn Val Trp Gly Gln Gly
            100                 105                 110

Thr Leu Val Ser Val Ser Ser
            115

```
<210> SEQ ID NO 102
<211> LENGTH: 120
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ser Leu Ser Ala Phe
            20                  25                  30

Thr Met His Trp Val Arg Gln Ala Pro Gly Lys Gly Leu Glu Trp Met
        35                  40                  45

Gly Gly Phe Asp Pro Glu Asp Gly Glu Thr Leu Tyr Ala Gln Lys Phe
    50                  55                  60

Gln Gly Arg Val Ser Met Thr Glu Asp Thr Ser Ser Asp Thr Ala Tyr
65                  70                  75                  80

Met Glu Leu Ser Ser Leu Arg Ser Asp Asp Thr Ala Val Tyr Tyr Cys
                85                  90                  95

Ala Ser Gly Glu Gly Ile Val Ala Ala Pro Phe Asp Tyr Trp Gly Gln
            100                 105                 110

Gly Thr Leu Val Thr Val Ser Ser
        115                 120

<210> SEQ ID NO 103
<211> LENGTH: 123
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 103

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Pro Phe Gly Asp Tyr
            20                  25                  30

Tyr Leu His Trp Val Gln Gln Ala Pro Gly Lys Gly Leu Glu Trp Met
        35                  40                  45

Gly Leu Val Tyr Pro Glu Asp Gly Glu Thr Ile Leu Ala Glu Arg Phe
    50                  55                  60

Gln Gly Arg Val Thr Ile Thr Ala Asp Ser Ser Thr Asp Thr Ala Tyr
65                  70                  75                  80

Met Glu Leu Asn Gly Leu Arg Tyr Ala Asp Thr Ala Val Tyr Tyr Cys
                85                  90                  95

Ala Thr Glu Pro Ile Pro Leu Ser Gly Asn Arg Gly Tyr Phe Asp Tyr
            100                 105                 110

Trp Gly Gln Gly Thr Leu Val Thr Val Ser Ser
        115                 120

<210> SEQ ID NO 104
<211> LENGTH: 128
<212> TYPE: PRT
<213> ORGANISM: Artificial Sequence
<220> FEATURE:
<221> NAME/KEY: source
<223> OTHER INFORMATION: Synthetic polypeptide
```

<400> SEQUENCE: 104

Glu Val Gln Leu Val Glu Ser Gly Ala Glu Val Lys Lys Pro Gly Ser
1               5                   10                  15

Ser Val Lys Val Ser Cys Lys Ala Ser Gly Asp Thr Phe Ile Arg Tyr
            20                  25                  30

Ser Phe Thr Trp Val Arg Gln Ala Pro Gly Gln Gly Leu Glu Trp Met
        35                  40                  45

Gly Arg Ile Ile Thr Ile Leu Asp Val Ala His Tyr Ala Pro His Leu
50                  55                  60

Gln Gly Arg Val Thr Ile Thr Ala Asp Lys Ser Thr Ser Thr Val Tyr
65                  70                  75                  80

Leu Glu Leu Arg Asn Leu Arg Ser Asp Asp Thr Ala Val Tyr Phe Cys
                85                  90                  95

Ala Gly Val Tyr Glu Gly Glu Ala Asp Glu Gly Glu Tyr Asp Asn Asn
            100                 105                 110

Gly Phe Leu Lys His Trp Gly Gln Gly Thr Leu Val Thr Val Ser Ser
        115                 120                 125

<210> SEQ ID NO 105
<211> LENGTH: 128
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 105

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asp
            20                  25                  30

Ala Ile Tyr Trp Val Arg Gln Ala Pro Gly Gln Gly Leu Glu Trp Met
        35                  40                  45

Gly Gly Val Ile Pro Ile Phe Gln Thr Ser Lys Tyr Ala Pro Lys Phe
50                  55                  60

Gln Gly Arg Val Thr Val Thr Ala Asp Lys Ser Thr Ser Thr Ala Tyr
65                  70                  75                  80

Leu Gln Leu Ser Ser Leu Arg Ser Glu Asp Thr Ala Val Tyr Tyr Cys
                85                  90                  95

Ala Arg Gly Gly Pro Val Leu Gln Ser Asp Asp Phe Trp Asn Gly Tyr
            100                 105                 110

Pro Pro Met Asp Val Trp Gly Gln Gly Thr Thr Val Thr Val Ser Ser
        115                 120                 125

<210> SEQ ID NO 106
<211> LENGTH: 129
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 106

Gln Val Gln Leu Leu Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met

```
                35                  40                  45
Gly Gly Ile Ile Pro Val Phe Gly Ser Ala Asn Tyr Ala Gln Lys Phe
    50                  55                  60
Gln Gly Arg Val Thr Ile Thr Ala Asp Glu Ala Thr Ser Thr Thr Tyr
65                  70                  75                  80
Met Glu Leu Ser Ser Leu Arg Ser Glu Asp Thr Ala Val Tyr Phe Cys
                85                  90                  95
Ala Lys Gly Gly Glu Asp Gly Asp Tyr Leu Ser Asp Pro Phe Tyr Tyr
            100                 105                 110
Asn His Gly Met Asp Val Trp Gly Gln Gly Thr Thr Val Thr Val Ala
        115                 120                 125
Ser

<210> SEQ ID NO 107
<211> LENGTH: 130
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 107

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Asn Tyr
            20                  25                  30
Ala Ile Asn Trp Val Arg Gln Ala Pro Gly Gln Gly Leu Glu Trp Met
        35                  40                  45
Gly Gly Ile Ile Pro Ile Phe Asn Ile Ala His Tyr Ala Gln Arg Phe
    50                  55                  60
Gln Gly Arg Val Ser Ile Thr Ala Asp Glu Ser Thr Ser Thr Ala Tyr
65                  70                  75                  80
Met Glu Leu Ser Ser Leu Arg Ser Glu Asp Thr Ala Val Phe Tyr Cys
                85                  90                  95
Ala Ser Pro Tyr Pro Asn Asp Tyr Asn Asp Tyr Ala Pro Glu Glu Gly
            100                 105                 110
Met Ser Trp Tyr Phe Asp Leu Trp Gly Arg Gly Thr Leu Val Thr Val
        115                 120                 125
Ser Pro
    130

<210> SEQ ID NO 108
<211> LENGTH: 130
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 108

Glu Val Gln Leu Leu Glu Ser Gly Ala Glu Val Lys Arg Pro Gly Ser
1               5                   10                  15
Ser Val Arg Val Ser Cys Gln Val Ser Gly Gly Ser Phe Ser Asn Tyr
            20                  25                  30
Ala Val Ser Trp Val Arg Gln Thr Pro Gly His Gly Leu Glu Trp Met
        35                  40                  45
Gly Gly Ile Ile Pro Met Phe Asn Ala Pro Asn Tyr Ala Gln Lys Phe
    50                  55                  60
```

His Gly Arg Val Thr Phe Ile Ala Asp Glu Ser Thr Arg Thr Val His
65                  70                  75                  80

Met Glu Leu Arg Ser Leu Arg Ser Glu Asp Thr Ala Val Tyr Phe Cys
                85                  90                  95

Ala Thr Ala Ser Glu Ala Thr Glu Asn Asp Tyr Tyr Gln Ser Pro Thr
            100                 105                 110

His Tyr Tyr Ala Met Asp Val Trp Gly Gln Gly Thr Ala Val Thr Val
        115                 120                 125

Phe Ser
    130

<210> SEQ ID NO 109
<211> LENGTH: 131
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 109

Gln Val Gln Leu Val Gln Ser Gly Ala Glu Val Lys Lys Pro Gly Ser
1               5                   10                  15

Ser Val Lys Val Ser Cys Gln Ala Ser Arg Gly Thr Phe Asp Thr Tyr
            20                  25                  30

Gly Ile Asn Trp Val Arg Gln Ala Pro Gly Gln Gly Leu Glu Trp Met
        35                  40                  45

Gly Gly Ile Val Pro Ile Phe Asp Thr Thr Asn Tyr Ala Gln Lys Phe
    50                  55                  60

Gln Gly Arg Val Ser Ile Thr Ala Asp Glu Ser Met Ser Thr Ala Tyr
65                  70                  75                  80

Met Glu Leu Ser Ser Leu Thr Ser Glu Asp Thr Ala Val Tyr Tyr Cys
                85                  90                  95

Ala Thr Arg Asn Pro Asn Glu Tyr Tyr Asp Glu Asn Ala Asp Tyr Ser
            100                 105                 110

Thr Val Tyr His Tyr Met Asp Val Trp Gly Lys Gly Thr Thr Val Thr
        115                 120                 125

Val Ser Ser
    130

<210> SEQ ID NO 110
<211> LENGTH: 131
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 110

Gln Val Leu Leu Glu Gln Ser Gly Ala Glu Val Lys Lys Pro Gly Ser
1               5                   10                  15

Ser Val Lys Val Ser Cys Arg Ala Ser Gly Gly Thr Phe Thr Ile Tyr
            20                  25                  30

Gly Ile Asn Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
    50                  55                  60

Gln Gly Arg Val Thr Phe Thr Val Asp Glu Ser Thr Ser Thr Ala Tyr
65                  70                  75                  80

```
Met Glu Leu Ser Ser Leu Thr Ser Asp Asp Thr Ala Val Tyr Phe Cys
                85                  90                  95

Ala Arg Asp Val Gly Pro Asp Trp Asp Asn Asp Tyr Tyr Asp Arg
            100                 105                 110

Ser Gly Arg Gly Val Phe Asp Tyr Trp Gly Gln Gly Thr Leu Val Thr
        115                 120                 125

Val Ser Ser
    130

<210> SEQ ID NO 111
<211> LENGTH: 131
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 111

Gln Val Leu Leu Glu Gln Ser Gly Ala Glu Val Lys Lys Pro Gly Ser
1               5                   10                  15

Ser Val Gln Val Ser Cys Lys Ala Ser Gly Gly Thr Phe Ser Met Tyr
            20                  25                  30

Gly Phe Asn Trp Val Arg Gln Ala Pro Gly His Gly Leu Glu Trp Met
        35                  40                  45

Gly Gly Ile Ile Pro Ile Phe Gly Thr Ser Asn Tyr Ala Gln Lys Phe
    50                  55                  60

Arg Gly Arg Val Thr Phe Thr Ala Asp Gln Ala Thr Ser Thr Ala Tyr
65                  70                  75                  80

Met Glu Leu Thr Asn Leu Arg Ser Asp Asp Thr Ala Val Tyr Tyr Cys
                85                  90                  95

Ala Arg Asp Phe Gly Pro Asp Trp Glu Asp Gly Asp Ser Tyr Asp Gly
            100                 105                 110

Ser Gly Arg Gly Phe Phe Asp Phe Trp Gly Gln Gly Thr Leu Val Thr
        115                 120                 125

Val Ser Ser
    130

<210> SEQ ID NO 112
<211> LENGTH: 134
<212> TYPE: PRT
<213> ORGANISM: Artificial Sequence
<220> FEATURE:
<221> NAME/KEY: source
<223> OTHER INFORMATION: Synthetic polypeptide

<400> SEQUENCE: 112

Gln Val Gln Leu Val Gln Ser Gly Ala Glu Val Asn Lys Pro Gly Ser
1               5                   10                  15

Ser Val Lys Val Ser Cys Gln Ala Ser Gly Ala Thr Leu Asn Ser His
            20                  25                  30

Ala Phe Ser Trp Val Arg Gln Ala Pro Gly Gln Gly Leu Glu Trp Met
        35                  40                  45

Ala Gly Ile Ile Pro Ile Phe Gly Ser Ser His Tyr Ala Gln Lys Phe
    50                  55                  60

Gln Gly Arg Val Thr Ile Thr Ala Asp Glu Ser Thr Arg Thr Val Tyr
65                  70                  75                  80

Leu His Leu Arg Gly Leu Arg Ser Asp Asp Thr Ala Val Tyr Tyr Cys
                85                  90                  95
```

-continued

Ala Ser Asn Ser Ile Ala Gly Val Ala Ala Gly Asp Tyr Ala Asp
            100                 105                 110

Tyr Asp Gly Gly Tyr Tyr Asp Met Asp Val Trp Gly Gln Gly Thr
        115                 120                 125

Thr Val Thr Val Ser Ser
        130

<210> SEQ ID NO 113
<211> LENGTH: 6
<212> TYPE: PRT
<213> ORGANISM: Artificial Sequence
<220> FEATURE:
<221> NAME/KEY: source
<223> OTHER INFORMATION: Synthetic 6xHis tag

<400> SEQUENCE: 113

His His His His His His
1               5

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: Synthetic primer

<400> SEQUENCE: 114
tttttttttt tttttttttt                                              20

<210> SEQ ID NO 115
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 115

Asp Xaa His Xaa His Ser Xaa Xaa
1               5

<210> SEQ ID NO 116
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

```
<220> FEATURE:
<221> NAME/KEY: MOD_RES
<222> LOCATION: (7)..(8)
<223> OTHER INFORMATION: Any amino acid

<400> SEQUENCE: 116

Ser Xaa Ala Xaa Ser Asp Xaa Xaa
1               5

<210> SEQ ID NO 117
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 117

Ala Xaa Asp Xaa Ser Tyr Xaa Xaa
1               5

<210> SEQ ID NO 118
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 118

Asp Xaa Ser Xaa Tyr Ser Xaa Xaa
1               5

<210> SEQ ID NO 119
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
```

```
<221> NAME/KEY: MOD_RES
<222> LOCATION: (7)..(8)
<223> OTHER INFORMATION: Any amino acid

<400> SEQUENCE: 119

Asp Xaa Tyr Xaa Asp Tyr Xaa Xaa
1               5

<210> SEQ ID NO 120
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 120

Asp Xaa Asp Xaa Tyr Asp Xaa Xaa
1               5

<210> SEQ ID NO 121
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 121

Tyr Xaa Asp Xaa Tyr Asp Xaa Xaa
1               5

<210> SEQ ID NO 122
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
```

<222> LOCATION: (7)..(8)
<223> OTHER INFORMATION: Any amino acid

<400> SEQUENCE: 122

Asp Xaa Ala Xaa Asp Asp Xaa Xaa
1               5

<210> SEQ ID NO 123
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 123

Asp Xaa Asp Xaa Asp Tyr Xaa Xaa
1               5

<210> SEQ ID NO 124
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 124

Tyr Xaa Asp Xaa Asp Asp Xaa Xaa
1               5

<210> SEQ ID NO 125
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)

```
<223> OTHER INFORMATION: Any amino acid

<400> SEQUENCE: 125

Asp Xaa Asp Xaa Ala Ser Xaa Xaa
1               5

<210> SEQ ID NO 126
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 126

Ser Xaa Ser Xaa Ala Asp Xaa Xaa
1               5

<210> SEQ ID NO 127
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 127

Ala Xaa Ser Xaa Asp Tyr Xaa Xaa
1               5

<210> SEQ ID NO 128
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid
```

<400> SEQUENCE: 128

Ala Xaa Ala Xaa Asp Asp Xaa Xaa
1               5

<210> SEQ ID NO 129
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 129

Asp Xaa Asp Xaa Ser Asp Xaa Xaa
1               5

<210> SEQ ID NO 130
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 130

Tyr Xaa Asp Xaa Ser Ser Xaa Xaa
1               5

<210> SEQ ID NO 131
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 131

Ala Xaa Asp Xaa Ser Asp Xaa Xaa
1               5

<210> SEQ ID NO 132
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 132

Asp Xaa Ser Xaa Asp Tyr Xaa Xaa
1               5

<210> SEQ ID NO 133
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 133

Ser Xaa Asp Xaa Asp Tyr Xaa Xaa
1               5

<210> SEQ ID NO 134
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 134

```
Asp Xaa Ala Xaa Asp Tyr Xaa Xaa
1               5
```

```
<210> SEQ ID NO 135
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 135

Tyr Xaa Asp Xaa Tyr Asp Xaa Xaa
1               5
```

```
<210> SEQ ID NO 136
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 136

Ser Xaa Tyr Xaa Asp Tyr Xaa Xaa
1               5
```

```
<210> SEQ ID NO 137
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 137
```

```
Ser Xaa Asp Xaa Ala Asp Xaa Xaa
1               5
```

<210> SEQ ID NO 138
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 138

```
Asp Xaa Asp Xaa Tyr Ser Xaa Xaa
1               5
```

<210> SEQ ID NO 139
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 139

```
Asp Ser Xaa Tyr Asp Xaa Xaa
1               5
```

<210> SEQ ID NO 140
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 140

```
Asp Xaa Ser Xaa Tyr Tyr Xaa Xaa
```

<210> SEQ ID NO 141
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 141

Tyr Xaa Asp Xaa Tyr Ala Xaa Xaa
1               5

<210> SEQ ID NO 142
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 142

Tyr Xaa Asp Xaa Ser Ser Xaa Xaa
1               5

<210> SEQ ID NO 143
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 143

Tyr Xaa Tyr Xaa Asp Tyr Xaa Xaa
1               5

```
<210> SEQ ID NO 144
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 144

Asp Xaa Ala Xaa Ala Asp Xaa Xaa
1               5

<210> SEQ ID NO 145
<211> LENGTH: 8
<212> TYPE: PRT
<213> ORGANISM: Artificial Sequence
<220> FEATURE:
<221> NAME/KEY: source
<223> OTHER INFORMATION: Synthetic peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid

<400> SEQUENCE: 145

Asp Xaa Asp Xaa Tyr Asp Xaa Xaa
1               5

<210> SEQ ID NO 146
<211> LENGTH: 296
<212> TYPE: DNA
<213> ORGANISM: Homo sapiens
<220> FEATURE:
<221> NAME/KEY: CDS
<222> LOCATION: (1)..(294)

<400> SEQUENCE: 146 gag gtg cag ctg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttt agc agc tat      96
Ser Leu Arg Leu Ser Cys Ala Ala Ser Gly Phe Thr Phe Ser Ser Tyr
            20                  25                  30 gcc atg agc tgg gtc cgc cag gct cca ggg aag ggg ctg gag tgg gtc     144
Ala Met Ser Trp Val Arg Gln Ala Pro Gly Lys Gly Leu Glu Trp Val
        35                  40                  45 tca gct att agt ggt agt ggt ggt agc aca tac tac gca gac tcc gtg     192
Ser Ala Ile Ser Gly Ser Gly Gly Ser Thr Tyr Tyr Ala Asp Ser Val
    50                  55                  60
```

```
aag ggc cgg ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gcc gta tat tac tgt      288
Leu Gln Met Asn Ser Leu Arg Ala Glu Asp Thr Ala Val Tyr Tyr Cys
                 85                  90                  95 gcg aaa ga                                                            296
Ala Lys <210> SEQ ID NO 147
<211> LENGTH: 98
<212> TYPE: PRT
<213> ORGANISM: Homo sapiens

<400> SEQUENCE: 147

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 148
<211> LENGTH: 294
<212> TYPE: DNA
<213> ORGANISM: Homo sapiens
<220> FEATURE:
<221> NAME/KEY: CDS
<222> LOCATION: (1)..(294)

<400> SEQUENCE: 148 gag gtg cag ctg gtg gag tct ggg gga ggc ttg gta cag cct gga ggg      48
Glu Val Gln Leu Val Glu Ser Gly Gly Gly Leu Val Gln Pro Gly Gly
 1               5                  10                  15 tcc ctg aga ctc tcc tgt gca gcc tct gga ttc acc ttc agt agt tat      96
Ser Leu Arg Leu Ser Cys Ala Ala Ser Gly Phe Thr Phe Ser Ser Tyr
                 20                  25                  30 gaa atg aac tgg gtc cgc cag gct cca ggg aag ggg ctg gag tgg gtt     144
Glu Met Asn Trp Val Arg Gln Ala Pro Gly Lys Gly Leu Glu Trp Val
             35                  40                  45 tca tac att agt agt agt ggt agt acc ata tac tac gca gac tct gtg     192
Ser Tyr Ile Ser Ser Ser Gly Ser Thr Ile Tyr Tyr Ala Asp Ser Val
         50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
 65                  70                  75                  80 ctg caa atg aac agc ctg aga gcc gag gac acg gct gtt tat tac tgt     288
Leu Gln Met Asn Ser Leu Arg Ala Glu Asp Thr Ala Val Tyr Tyr Cys
                 85                  90                  95 gcg aga                                                              294
Ala Arg
```

-continued

<210> SEQ ID NO 149
<211> LENGTH: 98
<212> TYPE: PRT
<213> ORGANISM: Homo sapiens

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 150
<211> LENGTH: 92
<212> TYPE: DNA
<213> ORGANISM: Artificial Sequence
<220> FEATURE:
<221> NAME/KEY: source
<223> OTHER INFORMATION: Synthetic oligonucleotide
<220> FEATURE:
<221> NAME/KEY: CDS
<222> LOCATION: (1)..(90)

<400> SEQUENCE: 150 ggc cag gcc ggc cag cac cat cac cat cac cat ggc gca tac ccg tac        48
Gly Gln Ala Gly Gln His His His His His His Gly Ala Tyr Pro Tyr
1               5                   10                  15 gac gtt ccg gac tac gct tct tag gag ggt ggt ggc tct gag gg              92
Asp Val Pro Asp Tyr Ala Ser     Glu Gly Gly Gly Ser Glu
            20                      25

<210> SEQ ID NO 151
<211> LENGTH: 23
<212> TYPE: PRT
<213> ORGANISM: Artificial Sequence
<220> FEATURE:
<221> NAME/KEY: source
<223> OTHER INFORMATION: Synthetic peptide

<400> SEQUENCE: 151

Gly Gln Ala Gly Gln His His His His His His Gly Ala Tyr Pro Tyr
1               5                   10                  15

Asp Val Pro Asp Tyr Ala Ser
            20

<210> SEQ ID NO 152
<211> LENGTH: 6
<212> TYPE: PRT
<213> ORGANISM: Artificial Sequence
<220> FEATURE:
<221> NAME/KEY: source
<223> OTHER INFORMATION: Synthetic peptide

```
<400> SEQUENCE: 152

Glu Gly Gly Gly Ser Glu
1               5
```